(12) United States Patent
Brennan et al.

(10) Patent No.: US 9,157,109 B2
(45) Date of Patent: Oct. 13, 2015

(54) BIOSENSORS UTILIZING INK JET-PRINTED BIOMOLECULE COMPATIBLE SOL GEL INKS AND USES THEREOF

(75) Inventors: John D. Brennan, Dundas (CA); Carlos Filipe, Ancaster (CA); Zakir Hossain, Hamilton (CA); Roger Luckham, Hamilton (CA); Anne Marie Smith, Ancaster (CA); Julie Marie Lebert, London (CA); Robert Pelton, Ancaster (CA)

(73) Assignee: McMaster University, Hamilton, Ontario (CA)

( * ) Notice: Subject to any disclaimer, the term of this patent is extended or adjusted under 35 U.S.C. 154(b) by 484 days.

(21) Appl. No.: 13/322,951

(22) PCT Filed: May 31, 2010

(86) PCT No.: PCT/CA2010/000802
§ 371 (c)(1),
(2), (4) Date: Feb. 13, 2012

(87) PCT Pub. No.: WO2010/135834
PCT Pub. Date: Dec. 2, 2010

(65) Prior Publication Data
US 2012/0135437 A1 May 31, 2012

Related U.S. Application Data

(60) Provisional application No. 61/182,389, filed on May 29, 2009.

(51) Int. Cl.
*C12Q 1/00* (2006.01)
*C12Q 1/46* (2006.01)
*G01N 33/543* (2006.01)
*G01N 33/548* (2006.01)
*G01N 33/552* (2006.01)

(52) U.S. Cl.
CPC *C12Q 1/001* (2013.01); *C12Q 1/46* (2013.01); *G01N 33/548* (2013.01); *G01N 33/5436* (2013.01); *G01N 33/552* (2013.01)

(58) Field of Classification Search
None
See application file for complete search history.

(56) References Cited

U.S. PATENT DOCUMENTS 4,810,636 A * 3/1989 Corey ............................ 435/14
6,016,689 A * 1/2000 Bright et al. ................. 73/31.05
2009/0011945 A1 1/2009 Bright et al.

FOREIGN PATENT DOCUMENTS

| WO | 03095515 A1 | 11/2003 |
|----|----|----|
| WO | 2004048603 A2 | 6/2004 |
| WO | 2008/003831 A1 | 1/2008 |

OTHER PUBLICATIONS

Bruzewicz et al., "Low-Cost Printing of Poly(dimethylsiloxane) barriers to define microchannels in paper)", Anal. Chem. 2008, 80: 3387-3392.*
International Search Report and Written Opinion for PCT/CA2010/000802 dated Sep. 17, 2010.
Narang, Upvan, et al., "Glucose Biosensor Based on a Sol-Gel Derived Platform", Anal. Chem., vol. 66, No. 19, Oct. 1, 1994, pp. 3139-3144.
Jordan, Jeffrey D., et al., "Aerosol-generated sol-gel-derived thin films as biosensing platforms", Analy. Chimica Acta 332 (1996), pp. 83-91.
European Search Report for European Application No. 10779977.7 dated Mar. 19, 2013.
Luckham, Roger Elliot, "Development of Sol-Gel-Based Bioactive Paper Sensing Platforms Toward Neurotoxin Detection" Master Thesis, Open Access dissertations and Theses Paper, 4235, Jul. 1, 2009.
Hossain S.M. Zakir et al. "Reagentless Bidirectional Lateral Flow Bioactive Paper Sensors for Detection of Pesticides in Beverage and Food Samples", Anal. Chemistry, vol. 81(21), Nov. 1, 2009, pp. 9055-9064.
Hossain, S.M. Zakir, et al. "Development of a Bioactive paper Sensor for Detection of Neurotoxins Using Piezoelectric Inkjet Printing of Sol-Gel Derived Bioinks", Anal. Chemistry, vol. 81(13), Jul. 1, 2009, pp. 5474-5483.

* cited by examiner

*Primary Examiner* — Anand Desai
(74) *Attorney, Agent, or Firm* — Bereskin & Parr LLP/S.E.N.C.R.L., s.r.l.; Patricia Folkins

(57) ABSTRACT

Novel solid-phase biosensors that utilize ink jet printing of biocompatible sol-gel based inks to create sensor strips are reported herein. Biomolecules and other reagents useful in bioassays to detect, for example, pathogenic microorganisms or toxic substances, are immobilized on a substrate, which can be paper based, by layering these substances between two layers of biomolecule compatible sol gel. The sol gel precursor solutions and solutions of the assay reagents are printed from separate nozzles in a layered approach which avoids clogging of the nozzles by the pre-mature gelling of the sol gel precursor solution. In certain embodiments of the application, a capture agent is used to concentrate a compound to be detected in specific areas on the substrate to facilitate detection.

22 Claims, 17 Drawing Sheets

BIOSENSORS UTILIZING INK JET-PRINTED BIOMOLECULE COMPATIBLE SOL GEL INKS AND USES THEREOF

RELATED APPLICATIONS

This application is a national phase entry of PCT/CA2010/000802, filed May 31, 2010, which claims priority from U.S. Provisional patent application Ser. No. 61/182,389 filed May 29, 2009, each of these applications being incorporated herein by reference in their entirety.

FIELD OF THE APPLICATION

The present application is in the field of biosensors, in particular biosensors comprising reaction zones in which recognition molecules or other assay components are immobilized using biomolecule compatible sol gels and the sol gels, recognition molecules and other assay components are printed on a substrate using ink-jet printing.

BACKGROUND OF THE APPLICATION

Recently, paper-based patterned solid-phase sensors (which are simple, portable, disposable and inexpensive) have been developed to run multiple bioassays and controls simultaneously.[17] These portable biosensing papers are extremely useful in remote settings as well as less industrialized countries where simple bioassays are essential in the first stages of detecting disease, and for monitoring environmental and food based toxins.

Several conventional deposition techniques such as dip coating,[8] spin coating,[9] aerosol spraying,[10] and electrophoretic deposition[11] have previously been used to deposit bioactive sol-gel derived materials. Among these, dip and spin coating are not practical for large-scale production. In addition, they are time consuming and are wasteful when dealing with expensive bioreagents. Aerosol spraying can be used for deposition of biomaterials, but is not easily adaptable to formation of millimeter scale patterns or for precise control of sol gel deposits. Electrophoretic deposition is normally used for fabrication of electrodes and the process requires an electrically conductive surface.[12]

It has been shown that entrapment of biomolecules within sol-gel derived materials allows proteins to retain their bioactivity for prolonged periods of time.[13,14] Furthermore, sol-gel based materials have previously been shown to be amenable to ink jet deposition (although not with proteins)[15] or screen printing with entrapped enzymes.[16]

Ink jet printing has been used to dispense, deposit or pattern, in either 2D or 3D arrangements cells/tissue,[17,18] DNA,[19] antibodies,[10] and enzymes.[2,15,18]

SUMMARY OF THE APPLICATION

Novel solid-phase biosensors that utilize ink jet printing of biocompatible sol-gel based inks to create sensor strips have been developed. In particular, two assays, utilizing two different colorimetric detection methods to monitor the activity of the enzyme, acetylcholinesterase (AChE) have been developed, along with an assay to detect the presence of microorganisms such as E. coli and total coliform bacteria. The assays all utilize biomolecule compatible sol gel matrixes that have been printed in specific configurations onto substrates, in particular substrates that support lateral flow of solutions. The sol gel matrixes are used to immobilize certain recognition elements that are appropriate for the assay to be performed, for example enzymes, functional nucleic acids or other functional biomolecules, substrates for these biomolecules and/or compounds used for detection. Advantageously, the recognition elements are printed in between two layers of the biomolecule compatible sol gel matrix. In certain embodiments, for example, when a compound is generated during the assay that is used for detection purposes, the "sol-gel/recognition element/sol-gel" configuration further includes a capture means which is used to restrict movement of the compounds to be detected, improving assay sensitivity. In the assays reported herein, colorimetric detection was utilized (although a person skilled in the art would appreciate that other detection means could also be used) and was achieved either by eye, using a digital camera and image analysis software, or using an office scanner, avoiding the need for expensive and sophisticated instrumentation. The biosensors developed herein could be used either as a dipstick or a lateral flow sensor, although lateral flow sensors are a particularly advantageous embodiment. The use of sol gel based entrapment produced sensors that retained activity and gave reproducible results after storage at 4° C. for at least 60 days, making these systems suitable for storage and use in the field.

Accordingly, the present application includes a biosensor comprising:
(a) a substrate;
(b) at least one reaction zone immobilized on the substrate, the reaction zone comprising, in order, beginning adjacent to the substrate: (i) a first biomolecule compatible sol gel layer; (ii) a recognition element layer; and (iii) a second biomolecule compatible sol gel layer; and
(c) a detection means,
wherein the first and second biomolecule compatible sol gel layers and the recognition element layer are immobilized on the substrate using ink jet printing.

The present application also includes a biosensor comprising:
(a) a substrate having a first and second end;
(b) at least one reaction zone immobilized on the substrate, the reaction zone comprising, in order, beginning adjacent to the substrate: (i) a first biomolecule compatible sol gel layer; (ii) a recognition element layer; and (iii) a second biomolecule compatible sol gel layer, wherein the first and second biomolecule compatible sol gel layers and the recognition element layer are immobilized on the substrate using ink jet printing; and
(c) a detection means,
wherein immersion of the first end of the substrate in a solution comprising or suspected of comprising an analyte results in lateral flow of the solution from the first end of the substrate to the second end by capillary action and flow through the at least one reaction zone results in reaction of the analyte with the recognition element, the reaction being detected by the detection means.

In an embodiment of the application, certain reaction zones further include an additional layer comprising a capture agent. The reaction zones that benefit from the presence of a capture agent are those that produce a product to be detected, this product being comprised in the detection means. The capture agent serves to restrict movement of the product, thereby concentrating the product in the reaction zone to facilitate detection. When the capture agent is a chemical compound, it is an embodiment of the application that the capture agent is printed as a layer under the first sol gel layer (i.e. adjacent to the substrate). The capture agent, in alternate embodiments, is a physical barrier printed on the substrate around the reaction zones that produce a product to be detected.

The present application also includes a biosensor for the detection of microorganisms having an intrinsic or recombinant β-glucuronidase or β-galactosidase enzyme comprising:
  (a) a substrate having a first and second end;
  (b) a first reaction zone immobilized on the substrate comprising in order, beginning adjacent to the substrate: (i) a first biomolecule compatible sol gel layer; (ii) an oxidizing agent; and (iii) a second biomolecule compatible sol gel layer;
  (c) a second reaction zone immobilized on the substrate comprising in order, beginning adjacent to the substrate: (i) a first biomolecule compatible sol gel layer; (ii) a chromogenic substrate for the enzyme and (iii) a second biomolecule compatible sol gel layer;
wherein immersion of the first end of the substrate in a solution comprising or suspected of comprising the microorganisms and that has been treated to lyse the microorganisms, results in lateral flow of the solution from the first end of the substrate to the second end by capillary action, the flow passing through the first reaction zone prior to passing through the second reaction zone.

In an embodiment, the first and second biomolecule compatible sol gel layers, the oxidizing agent and the chromogenic substrate for the substrate are immobilized on the substrate using ink jet printing of solutions comprising these substances, or in the case of the sol gels, precursors for these substances.

The chromogenic substrate for the enzymes is one that, when reacted with the enzyme produces a product that is oxidized by the oxidizing agent to a colored product that is detected. In an embodiment, the chromogenic substrate for β-glucuronidase is 5-bromo-4-chloro-3-indolyl-β-D-glucuronide (X-GLUC) and the chromogenic substrate for β-galactosidase is bromo-chloro-indolyl-galactopyranoside (X-GAL).

The present application also includes a biosensor for the determining AChE activity or for assaying for AChE modulators comprising:
  (a) a substrate having a first and second end; and
  (b) a first reaction zone immobilized on the substrate comprising in order, beginning adjacent to the substrate: (i) a cationic polymer; (ii) a first biomolecule compatible sol gel layer; (iii) AChE and DTNB; and (iv) a second biomolecule compatible sol gel layer.

The present application includes an alternate biosensor for the determining AChE activity or for assaying for AChE modulators comprising:
  (a) a substrate having a first and second end;
  (b) a first reaction zone immobilized on the substrate comprising in order, beginning adjacent to the substrate: (i) a first biomolecule compatible sol gel layer; (ii) IPA; and (iii) a second biomolecule compatible sol gel layer; and
  (c) a second reaction zone immobilized on the substrate comprising in order, beginning adjacent to the substrate: (i) a first biomolecule compatible sol gel layer; (ii) AChE; and (iii) a second biomolecule compatible sol gel layer;
wherein the first and second reaction zones are arranged so that during lateral flow of a solution from the first end of the substrate to the second end by capillary action, the solution passes through the first reaction zone prior to passing through the second reaction zone.

In an embodiment, the first and second biomolecule compatible sol gel layers, the cationic polymer, the AChE, the DTNB and the IPA are immobilized on the substrate using ink jet printing of solutions comprising these substances, or in the case of the sol gels, precursors for these substances.

The present application also includes assay methods that utilize the biosensor of the present application. In an embodiment, the assay is a method of detecting one or more analytes in a sample, wherein the sample comprises or is suspected of comprising the one or more analytes, the method comprising contacting the sample with the biosensor of the application and monitoring the detection means for a positive or negative result, wherein a positive result indicates the presence of the one or more analytes in the sample. In an embodiment of the application, the detection means is a colormetric method and the positive result is a presence of a color change on the biosensor.

In another embodiment, the present application also includes a method for determining if one or more analytes are modulators of a functional biomolecule comprising:
  (a) contacting a solution comprising the one or more analytes with a reaction zone on a biosensor of the application, wherein the reaction zone comprises the functional biomolecule;
  (b) contacting the reaction zone with a substrate for the functional biomolecule;
  (c) monitoring the detection means for a positive or negative result; and
  (d) comparing the positive or negative result in (c) with a control biosensor, wherein a positive or negative result in (c) that is different from the control indicates that the one or more analytes are modulators of the functional biomolecule.

In an embodiment of the application, the detection means is a colormetric method and the presence of a color change on the biosensor that is different from that on the control biosensor indicates that the one or more analytes are modulators of the functional biomolecule.

The present application further includes kits comprising the biosensors of the application. In an embodiment, the kit includes the biosensor and any further reagents for performing an assay using the biosensor. In a further embodiment, the kit includes instructions for using the biosensor in the assay and any controls needed to perform the assay. The controls may be on the biosensor itself, or alternatively, on a separate substrate. In a further embodiment the kit includes all of the components required to perform any of the assay methods of the present application.

The present application also includes a method for preparing a biosensor of the application comprising:
  (a) depositing a first biomolecule compatible sol gel precursor solution in a first reaction zone on a substrate using ink jet printing and allowing the first sol gel precursor solution to dry;
  (b) depositing a solution comprising the recognition element on top of the first biomolecule compatible sol gel precursor using ink jet printing and allowing the solution comprising the recognition element to dry;
  (c) depositing a second biomolecule compatible sol gel precursor solution on top of the recognition element using an ink jet printer and allowing the second sol gel precursor solution to dry.

In an embodiment, the method comprises depositing a solution comprising a capture agent in the first reaction zone onto the substrate using ink jet printing prior to depositing the first biomolecule compatible sol gel precursor solution or it further comprises depositing a physical barrier around the first reaction zone.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

BRIEF DESCRIPTION OF THE DRAWINGS

The application will now be described in greater detail with reference to the drawings in which.

Figure 14:
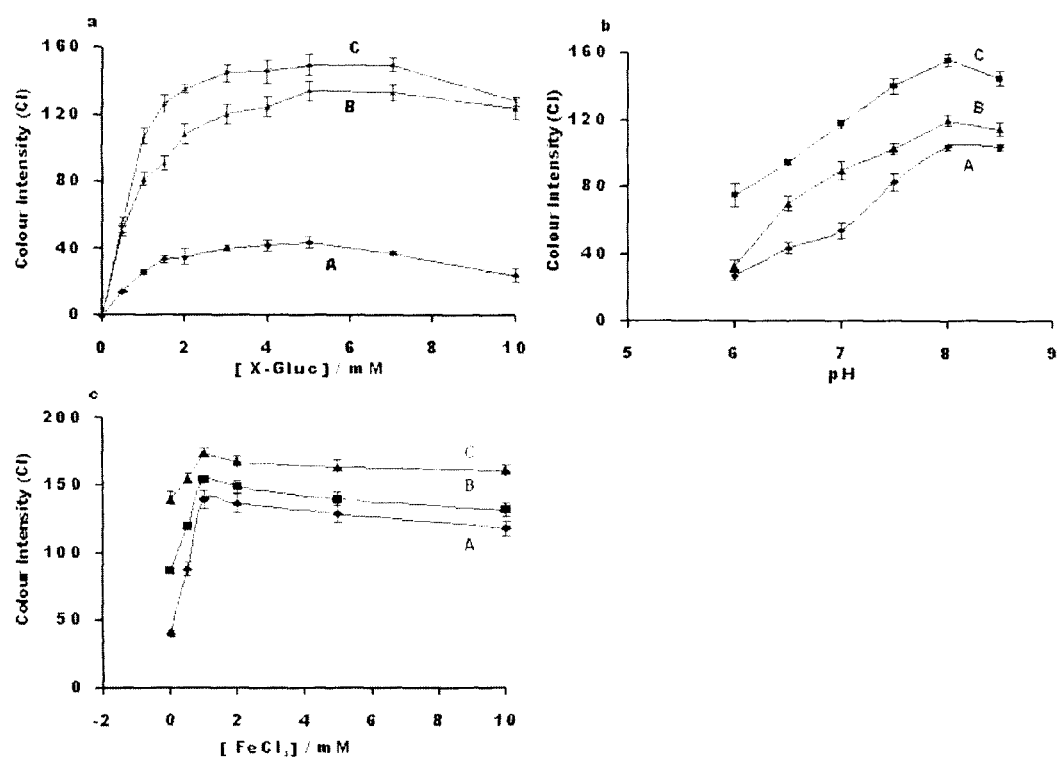

FIG. 14 shows the effects of X-Gluc, pH, oxidizing agent (e.g., $FeCl_3$), and drying time for the development of the paper-based lateral flow *E. coli* sensor. Color intensity at different (a) [X-Gluc], (b) pH, and (c) [$FeCl_3$] in the presence of GUS (final concentration 1 U/mL) on paper. Curve A, drying time 5 min; curve B, drying time 30 min; and curve C, drying time 60 min. All points are means±s.d. of four independent experiments for each concentration/level and all paper assays used 0.5 wt % PVAm as a capture agent.

Figure 15:
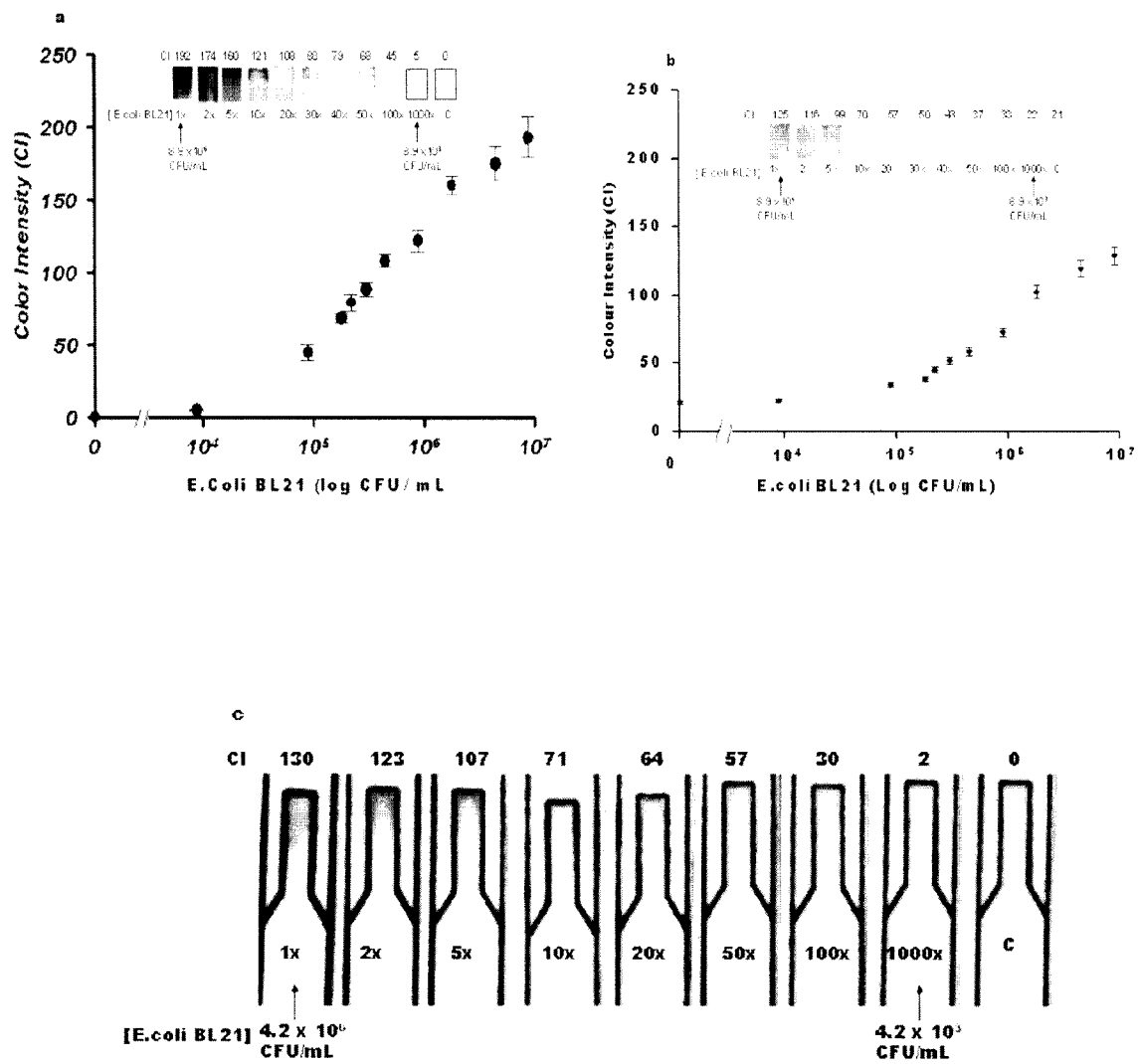

FIG. 15 shows detection of *E. coli* BL21 using both non-patterned and patterned paper strips. (a), (b) Color intensity with varying *E. coli* concentrations using non-patterned test trips. Insets are the color intensity (CI) generated at each cell concentration and the images were taken using office scanner (a), and the camera (b) for the same experiment. (c) Different concentrations of *E. coli* were detected using patterned paper sensor. All points are means±s.d. of four independent experiments for each concentration.

Figure 16:
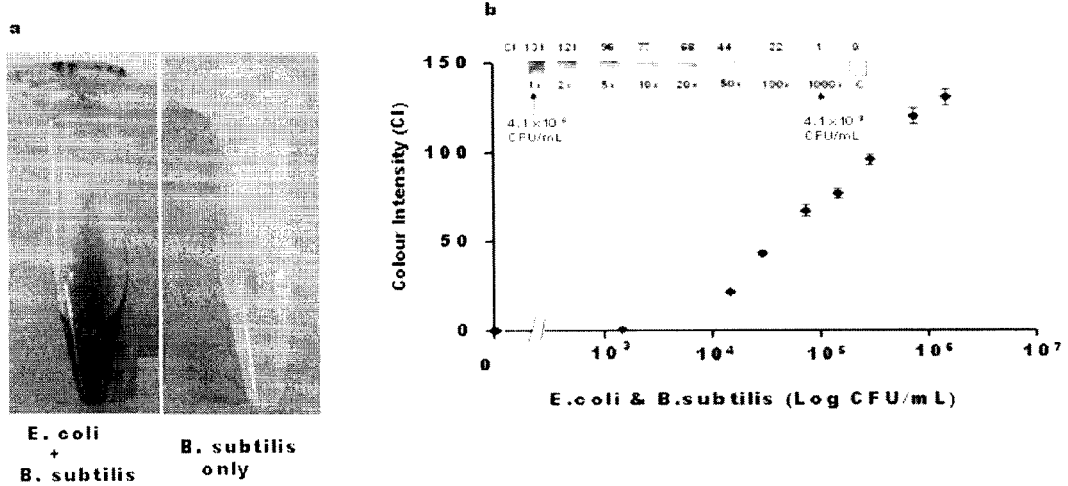

FIG. 16 shows detection of *E. coli* from coculture. *B. subtiliss* (~4.1×10⁶ CFU/mL) and *E. coli* BL21 (~4.1×10⁶ CFU/mL) are mixed together, lyzed (by using B-PER Direct lysing reagent) and tested both in solution assay (a) and by using the paper strips (b). In the case of *bacillus* alone-no color was observed in solution while in the case of co-culture, color was observed in both the assay systems.

Figure 17:
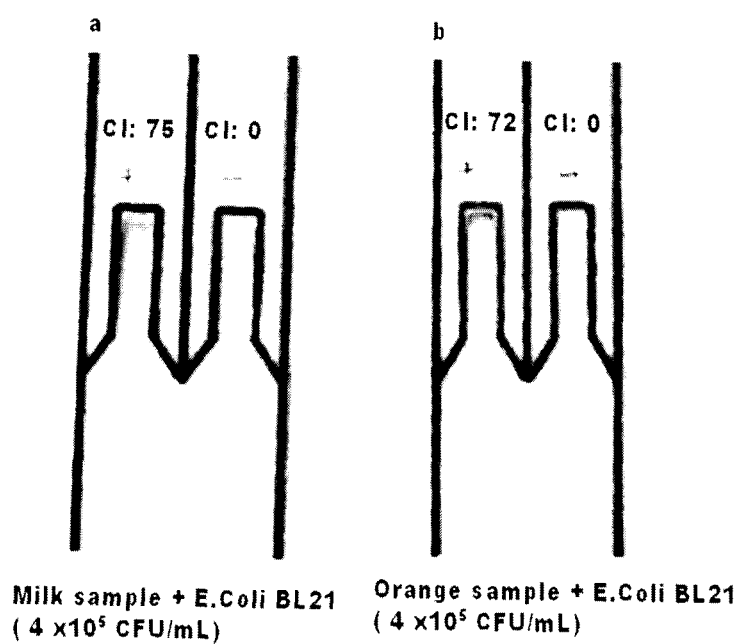

FIG. 17 shows detection of cell in the food samples, in which both 1% milk (a) and orange juice (b) were artificially contaminated with *E. coli* BL21 (4.1×10⁵ CFU/mL), respectively. The contaminated samples were then treated with B-PER Direct lysing reagent and tested using the bioactive paper sensor. In the negative control experiments, substrate (X-Gluc) was absent.

DETAILED DESCRIPTION OF THE APPLICATION

Definitions

The following definitions, unless otherwise stated, apply to all aspects and embodiments of the present application, including each independent embodiment described under separate headings hereinbelow.

By "biomolecule-compatible" it is meant that the silica sol gel either stabilizes proteins, and/or other biomolecules against denaturation or does not facilitate denaturation.

The term "biomolecule" as used herein means any of a wide variety of proteins, enzymes, organic and inorganic chemicals, other sensitive biopolymers including DNA and RNA, and complex systems including whole or portions of plants, animals, microorganisms and cells.

The term "substrate" as used herein refers to any solid support to which biomolecule compatible sol gel matrixes or other chemical entities can be adhered. In an embodiment of the application, the substrate comprises a substantially planar surface, and is made of any material that supports lateral flow of a solution. When the solution is aqueous based, the substrate is hydrophilic in nature. Conversely, when the solution is non-aqueous, the substrate is hydrophobic in nature. For aqueous solutions, therefore, the substrate may be made from, for example, a paper based material. For non-aqueous solutions, the substrate may be made from materials that are naturally hydrophobic, or that have been treated, for example by derivatization with hydrophobic groups, to make them hydrophobic. In further embodiments, the substrate is made from paper, glass, plastic, polymers, metals, ceramics, alloys or composites. In another embodiment, the substrate is made from paper or a paper-based material. In still other embodiments, the substrate is in the shape of a rectangular test strip, with the first and second ends being opposed to each other.

The term "paper" or "paper-based material" as used herein refers to a commodity of thin material produced by the amalgamation of fibers, typically plant fibers composed of cellulose, which are subsequently held together by hydrogen bonding. While the fibers used are usually natural in origin, a wide variety of synthetic fibers, such as polypropylene and polyethylene, may be incorporated into paper as a way of imparting desirable physical properties. The most common source of these kinds of fibers is wood pulp from pulpwood trees. Other plant fiber materials, including those of cotton, hemp, linen and rice, may also be used. The paper may be hydrophilic or hydrophobic, may have a surface coating, may incorporate fillers that provide desirable physical properties and may be previously modified prior to coating with the ink jet deposited sol-gel materials, by, for example, precoating with a hydrophilic, hydrophobic or charged polymer layer of organic or inorganic origin.

As used herein, the term "immobilized" of "entrapped" or synonyms thereof, means that movement of the referenced component of the biosensor, is restricted. Immobilization can be accomplished by physical means such as barriers, electrostatic interactions, hydrogen-bonding, bioaffinity, covalent interactions or combinations thereof.

The term "recognition element" refers to a chemical agent or a combination of chemical agents that specifically reacts with, interacts with or binds to the analyte and is immobilized on the biosensor, between two layers of biomolecule compatible sol gel. In an embodiment, the recognition element comprises a functional biomolecule that acts on a substrate that is the analyte or, conversely, the recognition element comprises a substrate for a functional biomolecule that is present in the analyte.

The term "functional biomolecule" refers to molecules, typically found in biological systems, that act or interact with substrates to modify the substrate in some detectable way. Examples of functional biomolecules include enzymes, DNA aptamers, RNA aptamers, PNA aptamers, DNA enzymes, RNA enzymes, DNA aptazymes and RNA aptazymes, and combinations thereof.

The term "capture agent" as used herein refers to a means for immobilizing or restricting the movement of a component of the biosensor. In particular, the capture agent restricts the movement of a compound to be detected, for example by colorimetric detection. By restricting the movement of a compound to be detected, this compound is more concentrated in a localized area which facilitates detection. In an embodiment, the capture agent is (bio)chemical agent that has affinity for the compound to be detected. For example, if the compound to be detected is an ionically charged compound, the capture agent is a chemical agent having an ionic charge that is opposite to the compound. Selection of suitable chemical capture agents would be within the abilities of a person skilled in the art based on the identity of the compound to be detected. In an embodiment, the compound to be detected is comprised in the detection means. In another embodiment, the chemical capture agents are comprised as a layer located below the first sol gel layer in a reaction zone where the compound to be detected is generated by reaction of the analyte with the recognition element. In another embodiment, the chemical capture agent is an ionic polymer that is printed onto the substrate below the first sol gel layer or, alternatively, is associated with the sol gel matrix. For example, when the compound to be detected is a cationic compound, such as, thionitrobenzoate (TNB) or indophenoxide anion, or a compound that possesses a certain anionic charge, such as ClBr-Indigo dye, a suitable chemical capture agent is a cationic polymer such as polyvinylamine (PVAm). In other embodiments of the application, the capture agent is selected from any of a wide variety of small molecules, proteins, peptides, enzymes and other sensitive (bio)polymers including DNA and RNA, and complex systems including whole plants, animals, microorganisms and cells, or portions thereof. Suitable capture agents, including antibodies, other proteins, DNA, DNA aptamers, RNA, RNA aptamers, complexing agents such as EDTA, charged polymers such as polyvinylamine, or molecularly imprinted polymers etc., are well known to those skilled in the art. Particular examples of capture agents are, but not limited to, charged polymers: poly(vinylamine), poly(allylamine), poly(ethyleneimine), polylysine, polyarginine, poly(acrylic acid), and poly(glutamic acid). The capture agents may also be heteropolymers, block co-polymers, or other macromolecules and may be further modified, for example with biotin, so that they can interact effectively with streptavidin.

In yet another embodiment of the application, the capture agent is a physical barrier that is printed onto the substrate either before or after the printing of the one or more reaction zones. For example, the barrier can be a wax ink that is printed on the substrate in an area that will result in entrapment of the compound to be detected in a specified area around the reaction zone.

The term "analyte" as used herein means any agent, including, but not limited to, small inorganic and organic molecules, biopolymers such as carbohydrates, lipids, DNA, RNA, peptides proteins, cells and micorganisms, for which one would like to sense or detect using a biosensor of the present application. The analyte may be isolated from a natural source or be synthetic. The term analyte also includes mixtures of compounds or agents such as, but not limited to, combinatorial libraries and samples from an organism or a natural environment.

The term "sample(s)" as used herein means refers to any material that one wishes to assay using the biosensor of the application. The sample may be from any source, for example, any biological (for example human or animal medical samples), environmental (for example water or soil) or natural (for example plants) source, or from any manufactured or synthetic source (for example foods and drinks). It is most convenient for the sample to be a liquid or dissolved in a suitable solvent to make a solution. For quantitative assays, the amount of sample in the solution should be known. The sample is one that comprises or is suspected of comprising one or more analytes.

The term "detection means" as used herein refers to a means to detect the presence of an analyte. Detection can be performed using any available method, including, for example, colorimetric, electrochemical and/or spectroscopic methods. Conveniently, detection is performed using colorimetric methods including both visual and analytical, using digital imagery. The detection means can simply be detection of the direct product formed, for example, by reaction or interaction of a functional biomolecule with a substrate (with either the functional biomolecule or the substrate being the analyte), if the product being formed possesses a color (or any signal) that is intense enough to be detected and that is distinct from the color (or signal) of any of the starting reagents. In this embodiment, the detection means is not a separate component of the biosensor, but is instead formed during the assay and therefore is an inherent part of the biosensor. In a further embodiment the detection means comprises the compound to be detected. In a further embodiment, the detection means comprises a separate entity that reacts or interacts with the direct product formed by reaction of, for example, a functional biomolecule with a substrate (with either the functional biomolecule or the substrate being the analyte), the reaction with the separate entity resulting in a distinct detectable signal. When the detection means comprises a separate entity, it can be located in its own reaction zone or combined with the recognition element.

The term "organic polyol" as used herein refers to an organic compound having more than one hydroxy or "OH" group. In an embodiment of the present application, the organic polyol is selected from sugar alcohols, sugar acids, saccharides, oligosaccharides and polysaccharides. Simple saccharides are also known as carbohydrates or sugars. Carbohydrates may be defined as polyhydroxy aldehydes or ketones or substances that hydrolyse to yield such compounds. The polyol may be a monosaccharide, the simplest of the sugars or a carbohydrate. The monosaccharide may be any aldo- or keto-triose, pentose, hexose or heptose, in either the open-chained or cyclic form. Examples of monosaccharides that may be used in the present application include, but are not limited to allose, altrose, glucose, mannose, gulose, idose, galactose, talose, ribose, arabinose, xylose, lyxose, threose, erythrose, glyceraldehydes, sorbose, fructose, dextrose, levulose and sorbitol. The polyol may also be a disaccharide, for example, but not limited to sucrose, maltose, trehalose, cellobiose or lactose. Polyols also include polysaccharides, for example, but not limited to dextran, (500-50,000 MW), amylose and pectin and the like. Other organic polyols that may be used include, but are not limited to glycerol, propylene glycol and trimethylene glycol.

The term "aryloxy" as used herein means phenoxy or naphthyloxy wherein, the phenyl and naphthyl groups may be optionally substituted with 1-5 groups, specifically 1-3 groups, independently selected from the group consisting of halo (fluoro, bromo, chloro or iodo), $C_{1-6}$alkyl, $C_{1-6}$alkoxy, OH, $NH_2$, $N(C_{1-6}alkyl)_2$, $NHC_{1-6}$alkyl. $C(O)C_{1-6}$alkyl. $C(O)NH_2$, $C(O)NHC_{1-6}$alkyl, $OC(O)C_{1-6}$alkyl, $OC(O)OC_{1-6}$alkyl, $NHC(O)NHC_{1-6}$alkyl, phenyl and the like.

The term "arylalkyleneoxy" as used herein means aryl-$(C_{1-4})$-oxy wherein aryl has the same meaning as in "aryloxy". Specifically, "arylalkyleneoxy" is a benzyl or naphthylmethyl group (i.e. aryl-$CH_2$—O).

By "normal sol-gel conditions" it is meant the conditions used herein to effect hydrolysis and condensation of the sol gel precursors, such as organic polyol derived silanes. This includes, in aqueous solution, at a pH in the range of 4-11.5, specifically in the range 5-10, and temperatures in the range of 0-80° C., and specifically in the range 0-40° C., and optionally with sonication and/or in the presence of catalysts known to those skilled in the art, including acids, amines, dialkyltin esters, titanates, etc.

As used in this specification and the appended claims, the singular forms "a", "an" and "the" include plural references unless the content clearly dictates otherwise. Thus for example, a composition containing "a chimeric peptide" includes one such peptide or a mixture of two or more peptides.

The term "suitable" as used herein means that the selection of the particular conditions would depend on the specific method to be performed, but the selection would be well within the skill of a person trained in the art. All method or process steps described herein are to be conducted under conditions sufficient to provide the desired result. Unless otherwise indicated, a person skilled in the art would understand that all method conditions, including, for example, solvent, time, temperature, pressure, reactant ratio and whether or not the method should be performed under an anhydrous or inert atmosphere, can be varied to optimize the desired result and it is within their skill to do so.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Biosensors of the Application

The automated deposition and permanent immobilization of biorecognition molecules on solid surfaces is a step in the development of bioactive paper-based sensors. To achieve this goal it is desirable to develop immobilization methods that are compatible with automated coating and/or printing and with biomolecules and which retain the reactive agents at the surface of the substrate. In the present application, the use of biocompatible sol-gel derived materials with ink jet printing methods has been explored for this purpose.

To evaluate the potential of ink jet deposition for fabrication of bioactive sensors, the detection of organophosphates via inhibition of immobilized acetylcholinesterase (AChE) was used herein as one model system. Organophosphates (e.g., paraoxon) and mycotoxins (e.g., aflatoxin B1) are classified as extremely hazardous compounds due to their potent toxicity to the human nervous system.[20,21] Organophosphate compounds are widely used as agricultural pesticides, insecticides and chemical warfare agents. These compounds are very stable and can rapidly diffuse into ground water reservoirs and thus exhibit a threat of contamination. Mycotoxins, particularly aflatoxin B1 (AfB1), are carcinogenic contaminants of food and animal feeds and as such are used as biochemical markers for food spoilage. In one model system reported in the present application, a signal generation method, utilizing the Ellman[22] colorimetric assay (FIG. 1) was developed. Advantageously, to allow permanent capture of the highly colored 5-thio-2-nitrobenzoate (TNB$^-$) anion, a cationic capture region was incorporated onto paper substrates via ink jet printing of polyvinylamine (PVAm). The binding of toxins (e.g., paraoxon, AfB1) to acetylcholinesterase (AChE) reduces AChE activity, and the residual activity is monitored based on the yellow color intensity that was produced. Following this simple and reliable assay mechanism, it was shown that it is possible to detect AChE inhibitors in a rapid and cost effective manner using either a dipstick or lateral flow biosensing format. This report on the utilization of ink jet printing in the development of sol-gel based paper biosensors provides a new platform for fabrication of bioactive paper strips for detection of drugs or environmental pollutants that affect both animals and humans. A second model system was based on an indophenyl acetate (IPA)-based colorimetric assay. AChE hydrolyzes the red-yellow colored substrate, IPA, to the blue-purple indophenoxide anion (IDO$^-$) which is then trapped over a finite region by the cationic polymer, polyvinyl amine (PVAm). The absence or decrease in blue-purple color, over this region, is indicative of the presence of AChE inhibitors. This paper-based sensor does not require any further reagents for proper functioning, as all reagents are deposited onto the paper surface with good long-term stability. A third model biosensor was developed for the detection of any microorganism having a β-glucuronidase (GUS) enzyme, including, for example, E. coli. In this biosensor, the chromogenic substrate 5-bromo-4-chloro-3-indolyl-β-D-glucuronide (X-GLUC) was immobilized in one reaction zone and an oxidizing reagent (FeCl$_3$) was immobilized in a separate reaction zone. In this assay, a solution comprising, or suspected of comprising, a microorganism having GUS, was treated to lyse the microorganism and a lateral flow-based biosensor was placed into the solution to allow lateral flow of the solution up the sensor by capillary action. The flow of the solution passes through the oxidizing agent zone first and the X-GLUC zone second. When the microorganism passes into the X-GLUC zone, the GUS enzyme, if present, will hydrolyse the X-GLUC to form a halogenated indoxyl intermediate which then dimerizes (via oxidation) to form a dark blue indigo dye. The use of the oxidizing agent in this assay is unique and advantageously provided faster response times. If the microorganism was present in the solution, a dark blue color from the indigo dye was detected in the X-GLUC reaction zone. To prevent leaching the color, either the capture agent, PVAm, was incorporated into the X-GLUC reaction zone, or hydrophobic barriers were pre-printed on to the biosensor in an area around the reaction zone.

All biosensors reported herein can be prepared by printing of biomolecule compatible sol gels onto the substrates. Conveniently, ink jet printing methods were used, in particular piezoelectric ink jet printing, to print layers of biomolecule compatible sol gels onto specific reaction zones on the substrates. The location of the reaction zones depended on the specific arrangements required for the assay in question. Advantageously, the assays were based on lateral flow of a solution up the substrate by capillary action, passing through the one or more reaction zones, wherein the solution comprised, or was suspected of comprising, an analyte to be detected. The biosensors were also amenable to dip-stick type assay formats.

Due to the rapid gelation of the sol gel precursor solutions when combined with many of the biomolecule or other reagent solutions, it was found to be most convenient to immobilize the reagents on the substrate using a layered approach to avoid clogging of the printing nozzles. Therefore, a first sol gel layer was printed on a reaction zone, followed by printing of a recognition element layer on top of the first sol gel layer and a second sol gel layer printed on top of the recognition element layer. Such an arrangement prevented reaction, and possible deactivation, of the recognition element by the support (or any other entity located under the first sol gel layer), prevented absorption of the recognition element into the support and prevent leaching of the recognition element from the sensor.

In reaction zones where a product is generated and is to be detected, it was advantageous to include a capture means to concentrate the detectable product in a distinct area. The capture means included a chemical agent having an affinity for the product and/or a physical barrier around the reaction zone. When the capture means was a chemical agent, it was convenient to print the agent onto the substrate below the first sol gel layer.

Therefore the present application includes a biosensor comprising:
(a) a substrate;
(b) at least one reaction zone immobilized on the substrate, the reaction zone comprising, in order, beginning adjacent to the substrate: (i) a first biomolecule compatible sol gel layer; (ii) a recognition element layer; and (iii) a second biomolecule compatible sol gel layer; and
(c) a detection means,
wherein the first and second biomolecule compatible sol gel layers and the recognition element layer are immobilized on the substrate using ink jet printing.

The present application also includes a biosensor comprising:
(a) a substrate having a first and second end;
(b) at least one reaction zone immobilized on the substrate, the reaction zone comprising, in order, beginning adjacent to the substrate: (i) a first biomolecule compatible sol gel layer; (ii) a recognition element layer; and (iii) a second biomolecule compatible sol gel layer, wherein the first and second biomolecule compatible sol gel layers and the recognition element layer are immobilized on the substrate using ink jet printing; and
(c) a detection means,
wherein immersion of the first end of the substrate in a solution comprising or suspected of comprising an analyte results in lateral flow of the solution from the first end of the substrate to the second end by capillary action and flow through the at least one reaction zone results in reaction of the analyte with the recognition element, the reaction being detected by the detection means.

The ink jet printing technique is simple, rapid, scalable, compatible with paper substrates and amenable to precise pattern formation. One factor to consider for ink jet printing is the formulation of the bioink and its rheological properties, in particular the viscosity and surface tension. Several additives can be introduced in the ink formulations to optimize the physical properties and to make them stable and ejectable. There are specific challenges associated with the formulation of biomolecule containing bioinks for reliable ink jet printing. Printing of biocompatible sol-gel derived inks is an even larger challenge since short gelation times of silica sols can cause gelation and clogging of the ink jet nozzles. At physiological pH, where most enzymes thrive, gelation of most biocompatible sol-gel precursors occurs within a minute to a few hours depending on buffer strength and type or additives being used.[23] For this reason, a multi-stage ink jet deposition method is reported here, wherein the silica sol and the buffered reagents are deposited from separate ink jet cartridges and thus do not interact prior to deposition on the paper surface, avoiding gelation in the in jet nozzle.

In an embodiment of the application, certain reaction zones further include an additional layer comprising a capture agent. The reaction zones that benefit from the presence of a capture agent are those that produce a product to be detected. The capture agent serves to restrict movement of the product, thereby concentrating the product in the reaction zone to facilitate detection. When the capture agent is a chemical compound, it is an embodiment of the application that the capture agent is printed as a layer under the first sol gel layer (i.e. adjacent to the substrate).

In an embodiment of the application, the biomolecule compatible silica sols and recognition elements are immobilized on the substrate by printing aqueous solutions of these entities that optionally include one or more additives. In an embodiment, the additives are used to optimize the rheological properties to allow reproducible jetting onto the substrates. Physico-chemical properties such as surface tension and viscosity are examples of parameters that can be optimized to make the solutions (also referred to as "inks") stable and ejectable. Such additives include surfactants and viscosity modifiers.

In an embodiment of the application, additives, such as surfactants, are included to adjust the surface tension of the inks to a printable range (for example, about, 30-40 $mN \cdot m^{-1}$) if adjustment is required. In an embodiment, the surfactant is a mild detergent such as Triton X-100. In a further embodiment the detergent is used in an amount of about 0.05 wt % to about 1 wt %, or about 0.1 wt %.

In an embodiment of the application additives are included to adjust the ink viscosity to a desired value (for example, about 2-10 cP) if adjustment is required. In an embodiment, the viscosity-modifying additive is glycerol. In a further embodiment, glycerol is used in an amount of about 20% (v/v) to about 50% (v/v), or about 30% (v/v)

In the present application, the biomolecule-compatible sol gels are is prepared using biomolecule-compatible techniques, i.e. the preparation involves biomolecule-compatible silica precursors and reaction conditions that are biomolecule-compatible. In an embodiment of the application, the biomolecule-compatible sol gel is prepared from a sodium silicate precursor solution. The preparation of sodium silicate solutions for use as a sol-gel precursor is known in the art.[38] In still further embodiments, the sol gel is prepared from organic polyol silane precursors. Examples of the preparation of biomolecule-compatible sol gels from organic polyol silane precursors are described in inventor Brennan's patent applications entitled "Polyol-Modified Silanes as Precursors for Silica", U.S. patent application publication no. US2004/0034203 filed on Jun. 2, 2003; and "Methods and Compounds for Controlling the Morphology and Shrinkage of Silica Derived from Polyol-Modified Silanes", U.S. CIP patent application publication no. US2004/0249082 filed on Apr. 1, 2004, the contents of which are incorporated herein by reference. In specific embodiments of the application, the organic polyol silane precursor is prepared by reacting an alkoxysilane, for example tetraethoxysilane (TEOS) or tetramethoxysilane (TMOS), with an organic polyol under conditions that avoids hydrolysis and condensation of the resulting precursor silane. Such conditions include reacting the alkoxy silane with the organic polyol under anhydrous conditions. Accordingly, the organic polyol silane precursor is desirably non-oligomeric so that optimal control over phase separation and gelation times is provided to permit greater control over the morphology of the resulting sol gel materials.

In embodiments of the present application, the organic polyol is selected from glycerol, sorbitol, maltose and dextran. Some representative examples of the resulting polyol silane precursors suitable for use in the methods of the application include one or more of diglycerylsilane (DGS), monosorbitylsilane (MSS), monomaltosylsilane (MMS), dimaltosylsilane (DMS) or dextran-based silane (DS). In embodiments, the polyol silane precursor is selected from one or more of DGS and MSS.

In a particular embodiment of the application, the sol-gel precursors are combined with an additive which causes spinodal decomposition (phase transition) before gelation, to provide macroporous silica matrixes. Macroporous silica can be used to entrap reagents with large molecular weights, i.e. those molecules that are large enough to not leach from the sol gel. Methods of forming macroporous silica, in particular, from polyol-modified silane precursors are described in inventor Brennan's patent application entitled "Methods and Compounds for Controlling the Morphology and Shrinkage of Silica Derived from Polyol-Modified Silanes", U.S. CIP patent application publication no. US2004/0249082 filed on Apr. 1, 2004, the contents of which are incorporated herein by reference. In particular, the sol-gel precursor is combined with one or more water soluble polymers which causes spinodal decomposition (phase transition) before gelation. The water soluble polymer may be selected from any such compound and includes, but is not limited to, for example, polyethylene oxide (PEO); polyethylene glycol (PEG); amino-terminated polyethylene glycol (PEG-NH$_2$); amino-terminated polyethylene oxide (PEO-NH$_2$); polypropylene glycol (PPG); polypropylene oxide (PPO); polypropylene glycol bis(2-amino-propyl ether) (PPG-NH$_2$); polyalcohols, for example, polyvinyl alcohol; polysaccharides; poly(vinyl pyridine); polyacids, for example, poly(acrylic acid); polyacrylamides e.g. poly(N-isopropylacrylamide) (polyNIPAM); or polyallylamine (PAM), or mixtures thereof. In embodiment of the application the water soluble polymer is selected from PEO, PEO-NH$_2$, PEG, PPG-NH$_2$, polyNIPAM and PAM, and mixtures thereof. In further embodiments of the application, the water soluble polymer is selected from PEO, PEO-NH$_2$ and polyNIPAM, and mixtures thereof. In still further embodiments, the water soluble polymer is PEO, for example PEO having a molecular weight between about 2000-100000 Da, suitably between about 5000 and 50000 Da, more suitably between about 8000 and 15000 Da. By "water soluble" it is meant that the polymer is capable of being formed into an aqueous solution having a concentration effective to result in phase separation occurring before gelation. It should be noted that the terms "oxide" (as in polyethylene oxide) and "glycol" (as in polyethylene glycol) may be used interchangeably and the use of one term over the other is not meant to be limiting in any way.

Sol gels may also be obtained by combining the sol-gel precursors, in particular organic polyol silane precursors, with one or more compounds of Formula I:

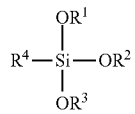

I wherein R$^1$, R$^2$ and R$^3$ are the same or different and represent a group that is hydrolyzed under normal sol-gel conditions to provide Si—OH groups; and R$^4$ is group selected from polyol-(linker)-, polymer-(linker)$_n$- and

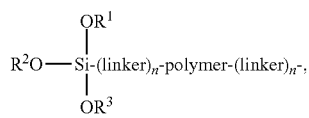

where n is 0 or 1. Such compounds are also described in detail in inventor Brennan's patent application entitled "Methods and Compounds for Controlling the Morphology and Shrinkage of Silica Derived from Polyol-Modified Silanes", U.S. CIP patent application publication no. US2004/0249082 filed on Apr. 1, 2004, the contents of which are incorporated herein by reference. In embodiments of the application, OR$^1$, OR$^2$ and/or OR$^3$ are the same or different and are derived from organic mono-, di-, or polyols. In embodiments of the present application, the group OR$^1$, OR$^2$ and/or OR$^3$ are derived from a polyol selected from glycerol, sorbitol, maltose, trehalose, glucose, sucrose, amylose, pectin, lactose, fructose, dextrose and dextran and the like. In further embodiments of the present application, the organic polyol is selected from glycerol, sorbitol, maltose and dextran. In other embodiments of the application, OR$^1$, OR$^2$ and OR$^3$ are the same and are selected from C$_{1-4}$alkoxy, for example, methoxy or ethoxy, aryloxy and arylalkyleneoxy. In further embodiments of the application, OR$^1$, OR$^2$ and OR$^3$ are all ethoxy. It will be apparent to those skilled in the art that other leaving groups such as chloride or silazane may also be used for the formation of silica according to the methods described in the application.

It should be noted that the groups OR$^1$, OR$^2$ and OR$^3$ are capable of participating directly in the hydrolysis/polycondensation reaction. In particular, these functional groups are alkoxy groups attached to the silicon atom at oxygen, i.e., "Si—OR", which may be hydrolyzed to provide "Si—O—H", which can condense with other "Si—O—H" or "Si—OR" groups to provide "Si—O—Si" linkages and eventually a three-dimensional network within a gel. Trifunctional silanes form silsesquioxanes upon hydrolysis and there is a lower degree of crosslinking in systems derived therefrom, in particular when compared with systems derived from tetrafunctional silanes. The remaining group attached to the silicon atom (R$^4$) is a group that generally does not participate directly in the hydrolysis/polycondensation reaction.

R$^4$ is a group that is not hydrolyzed under normal sol-gel conditions and preferably is stabilizing to biological substances, in particular proteins. In specific embodiments, R$^4$ is selected from one of the following groups:

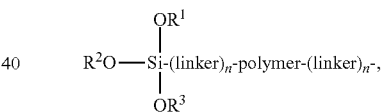

wherein n is 0-1 and OR$^1$, OR$^2$ and OR$^3$ are as defined above. The term "polyol" in R$^4$ has the same definition as described above for the groups OR$^1$, OR$^2$ and OR$^3$. In an embodiment of the invention, the polyol is derived from glucose or maltose. The term "polymer" in R$^4$ refers to any water soluble polymer, such as, but not limited to: polyethers, for example, polyethylene oxide (PEO); amino-terminated polyethylene oxide (PEO-NH$_2$); polyethylene glycol (PEG); polyethylene glycol bis(2-amino-propyl ether) (PEG-NH$_2$); polypropylene glycol (PPG); polypropylene oxide (PPO); polypropylene glycol bis(2-amino-propyl ether) (PPG-NH$_2$); polyalcohols, for example, polyvinyl alcohol; polysaccharides; poly(vinyl pyridine); polyacids, for example, poly(acrylic acid); polyacrylamides e.g. poly(N-isopropylacrylamide) (polyNIPAM); or polyallylamine (PAM). A linker group is required (i.e. n=1) when a direct bond between the silicon atom and the polymer would be hydrolyzed under normal sol-gel conditions. In embodiments of the invention, the polymer is a water soluble polyether such as PEO.

The sugar and polymer residues may be attached to the silicon atom through any number of linkers. Such linkers may be based on, for example, alkylene groups (i.e. —(CH$_2$)$_m$—, m=1-20, specifically 1-10, more specifically 1-4), alkenylene groups (i.e. —(CH=CH)$_m$—, m=1-20, specifically 1-10, more specifically 1-4), organic ethers, thioethers, amines, esters, amides, urethanes, carbonates or ureas. A person skilled in the art would appreciate that they are numerable linkers that could be used to connect the group, $R^4$, to the silicon atom.

Illustrative of compounds of Formula I of the present application, are two classes of the trifunctional silanes based on saccharides which are prepared as described in inventor Brennan's patent application entitled "Methods and Compounds for Controlling the Morphology and Shrinkage of Silica Derived from Polyol-Modified Silanes", PCT patent application WO 04/018360, filed Aug. 25, 2003 and corresponding U.S. CIP patent application publication no. US2004/0249082 filed on Apr. 1, 2004, the contents of which are incorporated herein by reference: monosaccharide- (compound 1) and disaccharide- (compounds 2 and 3) based trifunctional silanes are shown in Schemes 1 and 2. Hydrolysis and condensation of these species along with organic modified silanes (for example diglycerylsilane) allows the incorporation of these species into sol gel derived siliceous materials resulting in materials that have non-hydrolyzable sugar moieties covalently bound into the silica network. Such materials permanently incorporate protein stabilizing agents into the silica and retain water in the silica matrix, avoiding denaturation of the entrapped protein. Also prepared were polymeric bis(trifunctional silanes) 5 (see Scheme 3).

Although in both of the saccharide examples shown in Schemes 1 and 2, many different opportunities for modification with silanes exist, this scheme shows the modification of the anomeric hemiacetal centre at the terminus of the saccharidic chains. Oxidation of any of the sugars converts the anomeric hemiacetal into the lactone (Scheme 1). This is then opened by an amino-modified alkoxysilane to produce a sugar-modified coupling agent.[24] The key functional group tethering the two groups in this case is an alkylamide. Examples of specific sugar modified silanes are shown in Scheme 2.

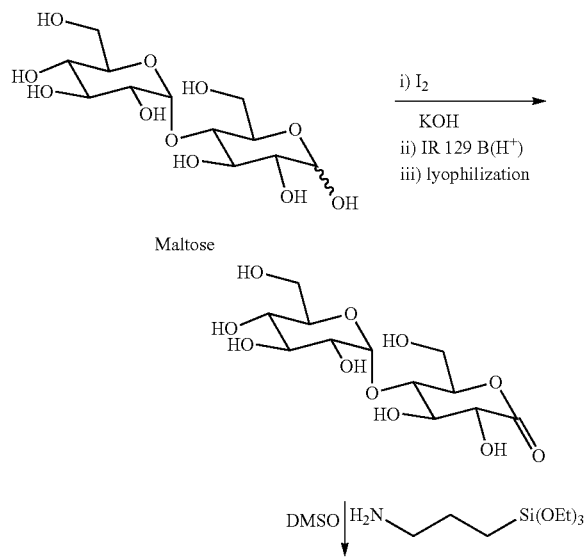

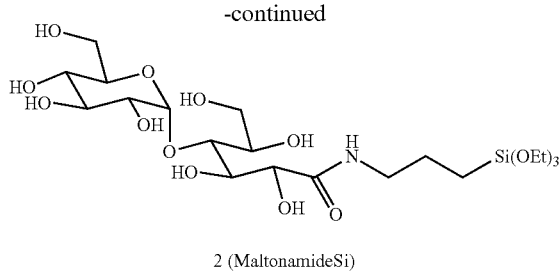

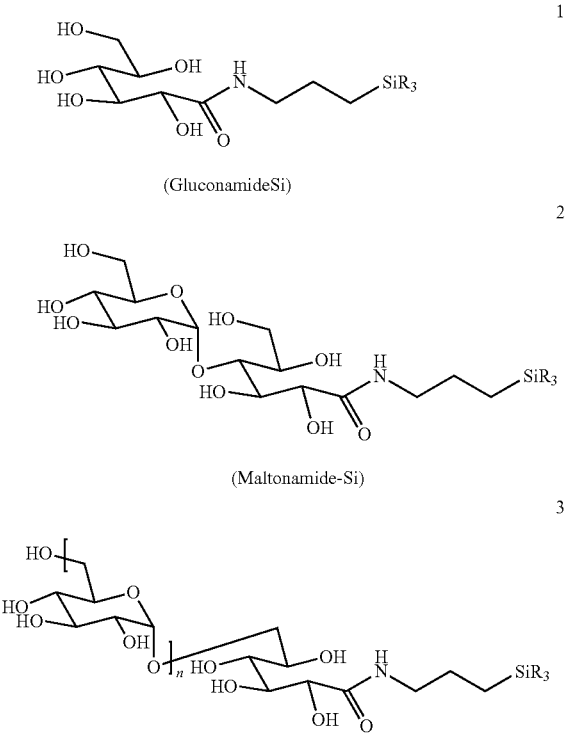

$SiR_3 = Si(OEt)_3$
MW(Dextran) = 10000-510000

Illustrative of compounds of Formula I wherein $R^4$ is

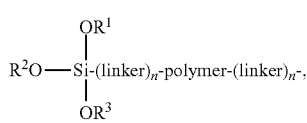

wherein $OR^1$, $OR^2$ and $OR^3$ are as defined above, are compounds 5 shown in Scheme 3. Compounds 5 can be prepared, for example, by reacting poly(ethylene oxide), first with allyl bromide (or any other suitable allylating reagent), followed by reaction with a trialkoxy-, triarylalkyleneoxy- or triaryloxysilane, in the presence of a catalyst, such as a platinum-derived catalyst, as shown in Scheme 3. When modified PEO polymers are used, for example the compound of Formula 5, it is an embodiment of the application that the starting PEO have a MW of greater than about 2000 g/mol. In this example the linker is an alkylene group, with m=3. Note some allyl-terminated PEO polymers 4 are commercially available. It would be apparent to one skilled in the art that other levels of functionality can also be used to bind these species to the siliceous matrix, such as: $R_{3-k}J_k$Si-linker-polymer-linker-SiJ$_k$R$_{3-k}$ and polymer-linker-SiJ$_k$R$_{3-k}$ where k=1-3 and J is a group that can participate in hydrolysis and condensation with the silica network.

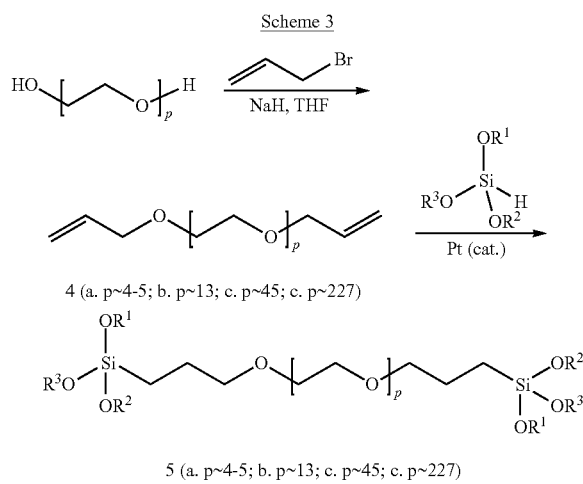

Scheme 3

4 (a. p~4-5; b. p~13; c. p~45; c. p~227)

5 (a. p~4-5; b. p~13; c. p~45; c. p~227)

In further embodiments of the application, the biomolecule-compatible sol gel precursor is selected from one or more of functionalized or non-functionalized alkoxysilanes, polyolsilanes or sugarsilanes; functionalized or non-functionalized bis-silanes of the structure (RO)$_3$Si—R'—Si(OR)$_3$, where R may be ethoxy, methoxy or other alkoxy, polyol or sugar groups and R' is a functional group containing at least one carbon (examples may include hydrocarbons, polyethers, amino acids or any other non-hydrolyzable group that can form a covalent bond to silicon); functionalized or non-functionalized chlorosilanes; and sugar, polymer, polyol or amino acid substituted silicates.

In yet another embodiment of the present application, the biomolecule compatible sol gel precursor solution comprises an effective amount of one or more other additives. In embodiments of the application the other additives are present in an amount to enhance the mechanical, chemical and/or thermal stability of the matrix and/or assay components. In an embodiment, the mechanical, chemical and/or thermal stability is imparted by a combination of precursors and/or additives, and by choice of aging and drying methods. Such techniques are known to those skilled in the art. In further embodiments of the application, the additives are selected from one or more of humectants and other protein stabilizing agents (for e.g. osmolytes). Such additives include, for example, one or more of organic polyols, hydrophilic, hydrophobic, neutral or charged organic polymers, block or random co-polymers, polyelectrolytes, sugars (natural or synthetic), and amino acids (natural and synthetic). In embodiments of the application, the one or more additives are selected from one or more of glycerol, sorbitol, sarcosine and polyethylene glycol (PEG). In further embodiments, the additive is glycerol.

In a particular embodiment of the application the biocompatible sol gel is a silica based glass prepared from a polyol modified silane, for example, diglyceryl silane, or sodium silicate precursor solution.

The precursor solution is prepared according to methods available in the art, for example about 1 g to about 5 g, suitably about 3.0 g, of sodium silicate is dissolved in about 10 mL of doubly distilled water (DDH$_2$O) followed by addition of about 5 g of Dowex cation exchange resin to replace the sodium ions with protons and stirring until a pH of approximately 4 is reached. The resulting sol is then filtered to remove any fine particulates that could interfere with ink jetting. Suitably, the organic polyol silane precursor solution is prepared by dissolving about 0.1 g to about 2.0 g, suitably about 1.0 g, of polyol silane, such as DGS, in about 10 mL of ddH$_2$O, followed by sonication. Again, the resulting sol is then filtered to remove any fine particulates that could interfere with ink jetting. A person skilled in the art would appreciate that if larger scale preparations are required, then the amounts of precursor and water may increase proportionally to provide precursor solutions of approximately the same concentration.

It is an embodiment of the application that the biomolecule-compatible sol gel layers were printed using a solution, or an ink, comprising about 30% (v/v) glycerol and about 0.1 wt % Triton-X100 and sodium silicate.

Depositing or printing of the solutions (reagents, capture agents or sol gel precursors) on the substrate was performed using ink jet printing. In an embodiment the ink jet printing is performed using a piezoelectric ink jet printer equipped with means to control the location of the inks being printed. Each different solution is printed using a separate printing cartridge.

The assays that may be performed using the biosensors of the present application include any assay based on an interaction between a functional biomolecule and its corresponding substrate that is amenable to detection. In an embodiment, the functional biomolecule is an enzyme. Non-limiting and some of their known substrates and detection systems are as follows:
  (ii) acetylcholinesterase—acetylthiocholine/dithiobisnitrobenzoate (DTNB);
  (iii) acetylcholinesterase—indophenyl acetate;
  (iv) urokinase plasminogin activator (uPA)—S-2244;
  (v) adenosine triphosphatases (ATPases)/kinases—ATP-βS/DTNB;
  (vi) β-glucuronidase—5-bromo-4-chloro-3-indolyl-β-D-glucuronide (X-GLUC)/FeCl$_3$/indigo dye;
  (vii) β-galactosidase—bromo-chloro-indolyl-galactopyranoside (X-GAL)/indigo dye
  (viii) DNA/RNA/PNA aptamers, DNA/RNA enzymes or a DNA or RNA aptamzyme/signaling method;
  (ix) functional nucleic acid/Φ29 DNA polymerase, circular template and dNTPs/gold nanoparticle labeled linear DNA of the same sequence as the circular template (or a portion thereof).

Biosensor for Microorganisms

Herein, a self-contained portable bioactive lab-on-paper sensor for sensitive visual detection of microorganisms based on the activity of an enzyme that is unique to the microorganism activity has been prepared. For example, the enzyme β-glucuronidase is endogenous to *E. coli* BL21 and K12, as well as *salmonella*, and β-galactosidase is endogenous to *E. coli* H7:O157 and these enzymes can be used as detection means for these microorganisms. In one example, the assay system was composed of a test strip, in which a chromogenic substrate for the β-glucuronidase, X-GLUC, and an oxidizing agent, such as FeCl$_3$, were entrapped using sol-gel derived silica inks in two different zones. Detection was achieved by eye, using a digital camera, or by an office scanner and image analysis software, avoiding the need for instrumentation or trained personnel. The assay provided good detection limits (~4×10³ CFU/mL) and rapid response times (~5 min) and remained stable and reproducible after storage in room temperature for at least 60 days, making the system suitable for storage and use in the field. Patterned paper sensors showed a higher sensitivity (LOD>2 fold) than that of non-patterned sensors. The assay system showed a negligible matrix effect with artificially E. coli contaminated milk and orange juice samples, provided that pH was adjusted to a suitable range close to pH 8.0. Based on the data, it is concluded that this novel paper strip biosensor provides a fast and convenient method for the visual detection of microorganisms comprising a β-glucuronidase, such as E. coli, which could be employed for first level screening of a variety of environmental and food samples, thus it could be a component of a simple and inexpensive field kit. Similar test strips could be prepared for other microorganisms.

The present application therefore includes a biosensor for the detection of microorganisms having an intrinsic or recombinant β-glucuronidase or β-galactosidase enzyme comprising:
(a) a substrate having a first and second end;
(b) a first reaction zone immobilized on the substrate comprising in order, beginning adjacent to the substrate: (i) a first biomolecule compatible sol gel layer; (ii) an oxidizing agent; and (iii) a second biomolecule compatible sol gel layer;
(c) a second reaction zone immobilized on the substrate comprising in order, beginning adjacent to the substrate: (i) a first biomolecule compatible sol gel layer; (ii) a chromogenic substrate for the enzyme and (iii) a second biomolecule compatible sol gel layer;
wherein immersion of the first end of the substrate in a solution comprising or suspected of comprising the microorganisms, and that has been treated to lyse the microorganisms, results in lateral flow of the solution from the first end of the substrate to the second end of the substrate by capillary action, the flow passing through the first reaction zone prior to passing through the second reaction zone.

In an embodiment, the first and second biomolecule compatible sol gel layers, the oxidizing agent and the a chromogenic substrate for the substrate are immobilized on the substrate using ink jet printing of solutions comprising these substances, or in the case of the sol gels, precursors for these substances.

The chromogenic substrate for the enzymes is one that, when reacted with the enzyme produces a product that is oxidized by the oxidizing agent to a colored product that is detected. In an embodiment, the chromogenic substrate for β-glucuronidase is 5-bromo-4-chloro-3-indolyl-β-D-glucuronide (X-GLUC) and the chromogenic substrate for β-galactosidase is bromo-chloro-indolyl-galactopyranoside (X-GAL). Other chromogenic substrates include, for example, 5-bromo-3-indolyl β-D-galactopyranoside (Bluo-Gla), 5-bromo-6-chloro-3-indolyl β-D-galactopryaniside (Magenta-Gal), 6-chloro-3-indolyl β-D-galactopyranoside (Salmon-Gal), 2-nitrophenyl β-D-galactopyranoside (ONPG) and 4-nitro β-D-galactopyranoside (PNPG).

It is well known to those skilled in the art that magnetic immunobeads or other known methods can be used to selectively pre-concentrate analytes present in complex mixtures prior to a range of different assays. Therefore the solution comprising the microorganism may be a sample taken directly from, for example the environment, a patient or food, or the sample can be pre-treated to concentrate the microorganism or to remove undesired materials.

Examples of lytic reagents include, for example, lytic bacteriophage, lysozyme or detergents. Contacting the resulting lysed solution with the biosensor will result in reaction of the functional biomolecule with the immobilized substrate, the reaction being detected by the detection means if the microorganism is present in the sample.

In an alternate embodiment, the lytic reagent is immobilized in a reaction zone on the biosensor, which is deposited by ink-jet printing at a location such that the solution passes through this zone prior passing through the substrate zone by lateral flow. Therefore the present application further includes a biosensor for the detection of microorganisms having an intrinsic or recombinant β-glucuronidase or β-galactosidase enzyme comprising:
(a) a substrate having a first and second end;
(b) a first reaction zone immobilized on the substrate comprising in order, beginning adjacent to the substrate: (i) a first biomolecule compatible sol gel layer; (ii) a lytic reagent; and (iii) a second biomolecule compatible sol gel layer;
(c) a second reaction zone immobilized on the substrate comprising in order, beginning adjacent to the substrate: (i) a first biomolecule compatible sol gel layer; (ii) an oxidizing agent; and (iii) a second biomolecule compatible sol gel layer;
(d) a third reaction zone immobilized on the substrate comprising in order, beginning adjacent to the substrate: (i) a first biomolecule compatible sol gel layer; (ii) a chromogenic substrate for the enzyme and (iii) a second biomolecule compatible sol gel layer;
wherein immersion of the first end of the substrate in a solution comprising or suspected of comprising the microorganisms, results in lateral flow of the solution from the first end of the substrate to the second end of the substrate by capillary action, the flow passing through the first reaction zone prior to passing through the second reaction zone prior to passing through the third reaction zone.

In an embodiment, the first and second biomolecule compatible sol gel layers, the oxidizing agent, the chromogenic substrate for the substrate and the lytic reagent are immobilized on the substrate using ink jet printing of solutions comprising these substances, or in the case of the sol gels, precursors for these substances.

AChE Biosensors

The present application includes a biosensor for the determining AChE activity or for assaying for AChE modulators comprising:
(a) a substrate having a first and second end; and
(b) a first reaction zone immobilized on the substrate comprising in order, beginning adjacent to the substrate: (i) a cationic polymer; (ii) a first biomolecule compatible sol gel layer; (iii) AChE and DTNB; and (iv) a second biomolecule compatible sol gel layer.

The present application includes an alternate biosensor for the determining AChE activity or for assaying for AChE modulators comprising:
(a) a substrate having a first and second end;
(b) a first reaction zone immobilized on the substrate comprising in order, beginning adjacent to the substrate: (i) a first biomolecule compatible sol gel layer; (ii) IPA; and (iii) a second biomolecule compatible sol gel layer; and
(c) a second reaction zone immobilized on the substrate comprising in order, beginning adjacent to the substrate: (i) a first biomolecule compatible sol gel layer; (ii) AChE; and (iii) a second biomolecule compatible sol gel layer;

wherein the first and second reaction zones are arranged so that during lateral flow of a solution from the first end of the substrate to the second end by capillary action, the solution passes through the first reaction zone prior to passing through the second reaction zone.

In an embodiment, the first and second biomolecule compatible sol gel layers, the cationic polymer, the AChE, the DTNB and the IPA are immobilized on the substrate using ink jet printing of solutions comprising these substances, or in the case of the sol gels, precursors for these substances.

Assays of the Application

The present application also includes assay methods that utilize the biosensor of the present application. In an embodiment, the assay is a method of detecting one or more analytes in a sample, wherein the sample comprises or is suspected of comprising the one or more analytes, the method comprising contacting the sample with the biosensor of the application and monitoring the detection means for a positive or negative result, wherein a positive result indicates the presence of the one or more analytes in the sample. In an embodiment of the application, the detection means is a colormetric method and the positive result is a presence of a color change on the biosensor.

A non-limiting example of such an assay is the testing of a sample, such as a food or environmental sample (such as water) for the presence of one or more pathogenic microorganisms. In this example, the biosensor will have immobilized in one of the reaction zones, a substrate for a functional biomolecule, such as an enzyme, that is representative of the microorganism. The microorganism is optionally preconcentrated by methods known to those skilled in the art (e.g., magnetic bead based preconcentration or filter based preconcentration). A solution is prepared containing the sample and the solution is treated with lytic reagents that will break apart the microorganism, releasing its internal contents which include the functional biomolecule. Examples of lytic reagents include, for example, lytic bacteriophage, lysozyme or detergents. Contacting the resulting lysed solution with the biosensor will result in reaction of the functional biomolecule with the immobilized substrate, the reaction being detected by the detection means if the microorganism is present in the sample. In a specific embodiment the application, the functional biomolecule is the enzyme β-glucuronidase or β-galactosidase, which are found only $E.\ coli$ and coliform bacteria. In an alternate embodiment, the lytic reagent is immobilized in a reaction zone on the biosensor, which is deposited by ink-jet printing and the sample solution passes through this zone prior passing through the substrate zone by lateral flow.

Further non-limiting examples, include biosensors comprising reagents that allow for detection of specific enzymes that may be biomarkers associated with disease. Such enzymes may be present in any biological sample, including tissue, blood, urine, tears, saliva or sweat or within microorganisms. In a specific embodiment, the enzyme is acetylcholinesterase (AChE), a protease such as urokinase plasminogen activator (UPa), which is upregulated in metastatic breast cancer, or kinases such as adenosine triphosphatase (ATPase), protein kinase A (PKA) or glycogen synthase kinase-3 (GSK-3), which are upregulated in certain disease states. In this embodiment a substrate for the enzyme and a suitable reporter molecule (detection means) are printed onto a substrate within a suitable matrix using ink-jet methods as described above. Suitable substrates and reporters include IPA for AChE, S-2244 for uPA, ATP-βS/DTNB for ATPases and kinases, and X-GLUC and X-GAL for β-glucuronidase or β-galactosidase, though other colorimetric reagents suitable for assaying such enzymes are known to those skilled in the art and are included within the scope of the application. The biosensor is contacted with the sample or a solution prepared from the sample and the analytes in the sample solution are allowed to move up the biosensor by lateral flow or the biosensor is simply dipped into the sample or the sample solution. Enzymes that are present within the sample will contact the reaction zone(s) containing the substrate and detection means and will produce a change, such as a color change that can be correlated to the presence and concentration of the enzyme.

In another embodiment, lysis of a microorganism can also release ATP. As an example, of a biosensor for ATP, a reaction zone may contain ATPase and malachite green. Alternatively, the reaction zone may contain adenylate kinase to convert AMP+ATP to two molecules of ADP, while another zone contains polyphosphate kinase to convert ADP back to ATP (ATP amplification) while a further zone contains a colorimetric reagent for ATP detection. Another alternative is to use a colorimetric assay based on oxidation of Fe(II) to Fe(III), which forms a colored complex with xylenol orange (XO). In this case, a reaction zone contains adenylate kinase (AK) and pyruvate kinase (PK) to amplify the amount of ATP and produce pyruvate. The same zone or another zone can contain pyruvate oxidase to generate $H_2O_2$ which oxidizes entrapped Fe(II) to Fe(III). The Fe(III) can form a complex with xylenol-orange (XO) so the colour of the dye changes from yellow to purple. Other colorimetric assays for ATP can also be employed and are within the scope of the application.

Alternative arrangements of reaction zones are also possible, as would be apparent to one skilled in the art. The present disclosure therefore includes an assay method for the detection of potentially pathogenic organisms, for example, $E.\ coli$, in, for example blood, tissue, air, water and food samples. The development of low-cost, portable and technically straightforward assay technologies is beneficial in a number of areas, including rapid testing of food or water quality, point-of-care diagnostics (i.e. field or home setting), or the rapid detection of bioterror agents. Development of such bioassays could also be useful for performing routine analysis in underdeveloped countries, or as an alternative to more expensive technologies for rapid testing in emergency situations.[25]

In another embodiment, the present application also includes a method for determining if one or more analytes are modulators of a functional biomolecule comprising:
 (a) contacting a solution comprising the one or more analytes with a reaction zone on a biosensor of the application, wherein the reaction zone comprises the functional biomolecule;
 (b) contacting the reaction zone with a substrate for the functional biomolecule;
 (c) monitoring the detection means for a positive or negative result; and
 (d) comparing the positive or negative result in (c) with a control biosensor, wherein a positive or negative result in (c) that is different from the control indicates that the one or more analytes are modulators of the functional biomolecule.

In an embodiment of the application, the detection means is a colormetric method and the presence of a color change on the biosensor that is different from that on the control biosensor indicates that the one or more analytes are modulators of the functional biomolecule.

Control biosensors are typically identical biosensors treated in the same way as the biosensor contacted with the solution comprising the one or more analytes, except that it is not contacted with the solution. Other controls include biosensors without the functional biomolecule or substrate.

In the latter method, when the biosensor is contacted with a substrate for the functional biomolecule, a product is produced, the product reacting with a reporter molecule (detection means) to produce a change, such as a color change, that can be detected. As a representative, non-limiting example, the enzyme acetylcholinesterase (AChE) acts on its substrate, acetylthiocholine (ATCh) in a sample to produce thiocholine which reduces 5,5'-dithiobis-(2-nitrobenzoic acid) (DTNB) to thionitrobenzoate. In an embodiment, the yellow colored thionitrobenzoate can be captured on cationic zone, for example a poly(vinylamine) (PVA) coated zone, (capture means) of the test strip to concentrate the color into a defined area. Further, most kinases will cleave the terminal phosphate off the substrate ATPβS (ATP with a sulfur on the β phosphorous) to produce a product that will also reduce DTNB. Also, AChE acts on the red-yellow substrate indophenyl acetate (IPA) to produce the blue-purple product indophenoxide (IDO$^-$) anion. Again the IDO$^-$ can be captured and concentrated using a cationic zone. The present disclosure therefore provides methods for assaying the activity of functional biomolecules, such as, kinases and ATPases, using the biosensors of the application. However, in further embodiments, the biosensor is initially contacted, in the reaction zone comprising the functional biomolecular, with a solution comprising one or more analytes that modulate, or are suspected of modulating, the activity of the functional biomolecule prior to contacting the reaction zone or with the one or more analytes. In this embodiment, if there is a change, such as a change in color, after exposure to the substrate in the presence of analyte(s) compared to the change, such as change in color, in the absence of analytes, or compared to biosensor controls not containing the functional biomolecule, then the activity of the functional biomolecule has been modulated. For example, if the color is less intense in the presence of the one or more analytes compared to in the absence of the one or more analytes, then the one or more analytes are inhibitors of the functional biomolecule. Conversely, if the color is more intense in the presence of the one or more analytes compared to in the absence of the one or more analytes, then the one or more analytes are promoters or enhancers of the functional biomolecule (e.g. for AChE, species whose reactions are catalyzed by a reducing entity to produce products that can directly reduce the DTNB or co-factors of the enzyme). Contacting the reaction zone comprising the functional molecule with solutions of the one or more analytes can be accomplished by for example, over spotting this zone with the solution, dipping or placing the second end of the biosensor in the analyte solution and allowing the solution to travel by capillary flow just into the reaction zone. In this latter example the biosensor can be inverted and the first end placed into a substrate solution to allow the substrate to travel into the reaction zone by lateral flow.

In another embodiment reaction zones can be placed on a test strip to allow for detection of analytes using functional biomolecules including DNA/RNA/PNA aptamers, DNA/RNA enzymes or a DNA or RNA aptamzyme, coupled to a signalling method. In an embodiment, the reaction zones contain reagents to allow detection of an analyte using colorimetric detection of the products of a reaction involving rolling circle amplification (RCA) or a primer that is exposed upon interaction of an aptamer, DNA enzyme or aptazyme (collectively referred to as a functional nucleic acid) with a target analyte. In a specific embodiment, the reaction zones are placed in the following order: (i) functional nucleic acid; (ii) Φ29 DNA polymerase, circular template and dNTPs; (iii) gold nanoparticle labeled linear DNA of the same sequence as the circular template (or a portion thereof) each sandwiched between two layers of biomolecule compatible sol gel. In an embodiment of the application, the assay is performed by placing the end of a lateral flow-based biosensor into a test solution. Analytes in the test solution first reach the functional nucleic acid and cause a structure-switching event or catalysis of cleavage of a suitable substrate. This reaction results in the release of a segment of DNA that flows to the second reaction zone containing the polymerase, dNTPs and circular template. The segment released is complementary to a portion of the circular template and thus acts as a primer to initiate the RCA reaction in the second reaction zone. After a suitable reaction time, the RCA product is detected by either moving the RCA product to the gold nanoparticle zone, or inverting the lateral flow device and flowing the gold nanoparticles into the zone containing the RCA product. The AuNP-labelled complementary DNA will initially be in a de-aggregated state and thus will be red in color. Upon hybridizing with the RCA product the AuNPs will be in close contact and thus will form blue colored aggregates. Formation of the blue colored aggregates indicates the presence of the target analyte in the test solution. In embodiments of the application, the analytes may be any analyte of interest in the biomedical, environmental, bioterror or agricultural fields. The analyte may also be a biomarker associated with a specific disease state, a microorganism or a metabolite present in a microorganism, a gene or a gene product. The analyte may be present in any test solution, including tissue, blood, urine, tears, saliva or sweat, or in food, water, soil or other samples.

In an embodiment of the application, when the change is a color change it may be quantified, for example, using a digital camera with a macrofocus lens and using standard image analysis software.

As stated above, the analyte may be contacted with the biosensor using either lateral flow of the analyte solution up the substrate via capillary action, overspotting of analyte solution onto the biosensor (i.e., with a pipette) or dipping the biosensor into the analyte solution.

In other embodiments of the present disclosure, a series of reaction zones can be placed on a test strip to allow multi-step reactions to occur as a result of lateral flow of analyte along the biosensor.

In an embodiment of the present application, ink-jet printing is used to print different reaction zones onto a biosensor in a manner that allows movement of reactants from one area to another by capillary flow. As a representative, non-limiting, example, the chromogenic substrate IPA can be printed in one zone and AChE can be printed in a second zone, while PVAm is printed either in the same zone as AChE or in a separate region. In an embodiment of the present disclosure, the IPA, AChE and PVAm zones are printed such that lateral flow of liquid upon contacting an analyte test solution will result in liquid reaching the IPA zone first, transporting the IPA to the AChE zone to undergo reaction with the enzyme, and the product is then transported to the PVAm capture zone to allow detection of a color change. In another embodiment the IPA, AChE and PVAm zones are printed such that lateral flow of an analyte solution will cause analytes to first contact the AChE zone when one end of the biosensor is placed in contact with the analyte solution, allowing for incubation of analytes with the enzyme. The other end of test strip can then be placed in the analyte solution to allow lateral flow of liquid into a reaction zone containing IPA so that the IPA is transported into the AChE region. Any product that is produced can be captured by a PVAm layer that is directly below the AChE-containing sol-gel. In this manner, slow inhibitors of the enzyme can be detected by measuring the color change in the presence of the analyte solution and comparing it to the color of controls that have no analyte compounds present or no enzyme present.

EXAMPLES

The following non-limiting examples are illustrative of the present application:

Example 1

Development of Bioactive Paper Sensors Using Piezoelectric Ink Jet Printing of Sol Gel Derived Bioinks Chemicals:

Sodium silicate solution (~14% NaOH, ~27% $SiO_2$), tetraethylorthosilicate (TEOS, 98%), Dowex 50WX8-100 ion-exchange resin, acetylcholinesterase (AChE, from *electrophorus electricus*, EC 3.1.1.7), paraoxon, aflatoxin B1 (AfB1, from *aspergillus flavus*), 5,5'-dithiobis-(2-nitrobenzoic acid) (DTNB), carboxymethylcellulose sodium salt (CMC), and Triton X-100 were obtained from Sigma-Aldrich. Anhydrous glycerol and acetylthiocholine iodide (ATCh) were purchased from Fluka BioChemika Ultra (UK). Diglyceryl silane (DGS) was synthesized in our lab using by transesterification of TEOS with anhydrous glycerol as described in detail elsewhere.[26] Polyvinylamine (PVAm; 1.5 MDa) was obtained from BASF (Mississauga, Canada), as a gift. Mead brand cardboard paper substrate with a white hydrophobic clay coating (Manufactured by Hilroy, Toronto, Canada) was purchased from McMaster University Bookstore. Distilled deionized water ($ddH_2O$) was obtained from a Milli-Q Synthesis A10 water purification system. All other reagents were of analytical grade.

Preparation of Solutions:

Stock solutions of the ATCh, paraoxon and AfB1 were made up daily and were not used for more than 3 h after preparation to minimize the potential for hydrolysis. Tris buffer (100 mM, pH 8) was used for dilution of ATCh. A mixture of Tris buffer (50 mM, pH 6.8) and 5% cyclohexane (Sigma) was used for dilution of paraoxon, while a mixture of Tris buffer (50 mM, pH 6.8) and 5% methanol (Sigma) was used for dilution of AfB1. These solvents not only aid in dissolution of the AChE inhibitors, but also enhance the affinity of paraoxon[27] and aflatoxin[28] for binding to AChE. Furthermore, this level of organic solvent has been shown not to affect the stability of AChE in any way. Note that experiments conducted without organic solvent present produced significantly lower detection limits for paraoxon or AfB1. Therefore, for practical applications, it is recommended that low levels of organic solvents be used not only for dissolution purposes but also to enhance sensitivity. Distilled deionized water ($ddH_2O$) was used to dissolve PVAm. All other solutions were prepared using Tris buffer (100 mM, pH 8) if not otherwise stated. CAUTION: Both AfB1 and paraoxon are extremely toxic. These materials should be handled with gloves and used in a fumehood.

Preparation of Sol-Gel Materials:

Two biocompatible sol-gel precursors, diglyceryl silane (DGS) and sodium silicate (SS) were used to prepare sols for enzyme entrapment and printing onto paper. DGS sols were made up by mixing 10 mL of $ddH_2O$ with 1 g of finely ground DGS. The mixture was sonicated on ice bath for 20 min to dissolve the DGS and then filtered through a 0.22 µm membrane syringe filter to remove any particulates in the solution.

SS sols were prepared by mixing 10 mL of $ddH_2O$ with 2.9 g of sodium silicate solution (pH~13) followed by addition of 5 g of Dowex cation exchange resin to replace $Na^+$ with $H^+$. The mixture was stirred for 30 seconds to reach a final pH of ~4, and then vacuum filtered through a Büchner funnel. The filtrate was then further filtered through a 0.45 µm membrane syringe filter. These sols were used to formulate silica-containing inks as described below.

Figure 1:
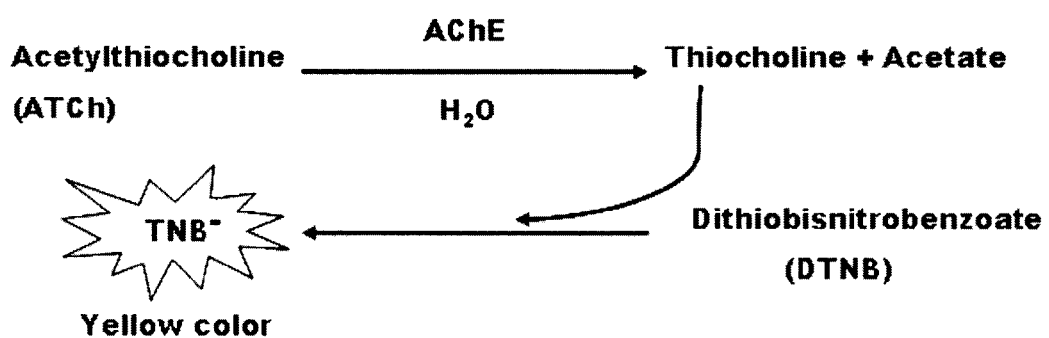
FIG. 1 is a schematic representation of the detection principle of the Ellman assay. Acetylcholinesterase (AChE) hydrolyzes the acetylthiocholine (ATCh) and forms thiocholine (TCh), which then reacts with dithiobisnitrobenzoate (DTNB) to generate 5-thio-2-nitrobenzoate (TNB, an anion), which is yellow in color.

Construction of Bioactive Paper-Based Solid-Phase Sensor:

The papers were coated with a total of three different materials in a specific sequence. In general, this involved: 1) printing of a PVAm underlayer directly onto the paper surface; 2) printing of a silica sol intermediate layer; 3) printing of a buffered enzyme solution containing AChE (final conc. 50 U/mL) and DTNB (final conc. 500 µM); and 4) printing of a silica sol overlayer, as shown in FIG. 1. Between printing of the different silica and bioinks, 15-20 min was allowed for air drying. The different printing solutions (PVAm, sol or enzyme) were modified by addition of glycerol to control viscosity and Triton X-100 to control surface tension so as to optimize the printing performance (ability to jet the inks) as well as the enzyme activity, as described below. As noted in Table 1, addition of glycerol to PVAm inks was not necessary as the viscosity of an aqueous solution of this polymer was on the order of 3 cP. This high viscosity of the 0.5 wt % solution is likely due to the high molecular weight (ca. 1.5 MDa) of the polymer. The solutions were deposited using a piezoelectric ink jet printer (DMP-2800) from Fujifilm Dimatix, Inc (Japan) using Drop Manager software (version 1.3.0.7). This system has a microelectromechanical system (MEMS)-based cartridge-style printhead that allows filling with desired bioinks (ca. 0.5-2 mL). Each cartridge has 16 nozzles linearly spaced at 254 microns with typical drop sizes of 1-10 pL. The instrument is equipped with a drop imaging system (Drop Watcher) that allows observation and capture of the events during drop formation on the printhead nozzles and the trajectory of the drops after ejection. Jetting conditions are described in Table 1. In all cases the bioactive inks were printed by applying 16 piezo firings with one printing cycle per ink in a stepwise fashion as a 0.25×0.25 cm square pattern onto Mead brand cardboard (paper substrate, 10×8 cm) using a separate cartridge for each of the PVAm, silica and enzyme "inks". For control experiments, a buffer that did not contain AChE was printed between the silica layers. Other controls involved printing of AChE+DTNB directly onto the PVAm underlayer without a silica coating, and printing of AChE+DTNB onto PVAm/silica without printing a silica overlayer.

Ink Viscosity and Surface Tension Measurements:

The dynamic viscosity of the bioink components was measured using a capillary viscometer (Cannon-Fenske viscometer, size 75, Vineland, N.J.) at room temperature. The viscometer was calibrated with MilliQ water (viscosity~1 cP) before measuring the viscosity of the bioinks. Surface tension values were measured using a Krüss pendant drop apparatus. The shape of the pendant drop was analyzed using DSA10 shape analysis software by applying the Laplace equation. Pendant drops were formed by a Krüss needle with an outer diameter of 1.5 mm, connected to a 1 mL Perfektum glass syringe from Popper & Sons Inc. MilliQ water with surface tension of 72.8 mN/m was used to calibrate the needle's inner diameter. All surface tension values of pendant drops were measured at 22° C. with temperature controlled by a NESLAB thermostat system.

Surface Topography:

Paper substrates were subjected to optical profilometry and SEM imaging prior to deposition of any materials, after ink jet deposition of PVAm and after deposition of both PVAm and the silica/enzyme/silica layers. Optical profilometry images were obtained using WYKO NT 1100 Optical Profiling System using the VSI measurement mode and a magnification of 20×. For SEM, samples were sputter-coated with platinum (layer thickness 15 Å) to avoid charging effects and were imaged using a JEOL Ltd. (Tokyo, Japan) JSM-7000F instrument operating at 5 kV and a probe distance of 5.8 mm. The hydrophilic or hydrophobic nature of surface was also estimated by measuring the contact angle of ddH$_2$O drop on paper using a Krüss pendant drop apparatus.

Monitoring AChE Activity on Paper:

Prior to monitoring AChE activity on paper, the activity of AChE as a function of enzyme concentration was optimized. Different concentrations of AChE (0~200 U/mL) were entrapped in SS+30% glycerol in a 96 well plate (total volume of 80 µL). A mixture (20 µL) of DTNB (500 µM) and ATCh (300 µM) was then added into each well and incubated for 5 min to allow color development. The absorbance at 412 nm was then measured using a TECAN Safire microwell plate reader.

The AChE activity on the bioactive paper strip was evaluated by measuring the color intensity produced by the enzymatic reaction using Ellman's method. The performance can be assessed in two ways: a) by direct addition of substrate solution to sensing area, and b) by immersion into the substrate solution. The performance of our sensor was essentially the same for both these cases. However, in the case of direct analyte addition, only small amounts of reagent are needed (5 µL) relative to dipstick sensors (~2 mL), reducing cost per assay. For optimization of AChE activity, small amounts (5 µL) of different concentrations of the substrate ATCh (0-500 µM) was added directly onto the sensing area of the paper strip and incubated for 5 min at room temperature to allow the yellow color to develop. The color intensity of the sensing areas was quantified by obtaining a digital image (Canon A630, 8.0 MegaPixel operated in automatic mode with no flash and with the macroimaging setting on) and using ImageJ™ software to analyze the jpeg images. ImageJ™ software uses a 256 bit color scale and for image processing the images were inverted so that areas that were originally white became black and corresponded to a color intensity of zero and while areas that were originally black became white and corresponded to 256. Based on this scale, increases in the amount of yellow color cause an increase in color intensity of the sensor strips. To account for variations in color intensity owing to differences in environmental illumination, a background subtraction (color intensity of the paper surface closest to the sensing area) was done for each data point.

The long-term stability of the enzyme printed on the paper strip was evaluated over a period of 60 days with the paper strip stored at 4° C. The assay conditions were the same as those described above.

Monitoring the Effect of PVAm:

In order to investigate the effect of the PVAm underlayer on the sensor performance, a lateral flow-based paper chromatographic system was developed. In this case, strips of Whatman No. 1 filter paper (Sigma-Aldrich) were used in place of the Mead cardboard as the Whatman paper is more hydrophilic and thus supports capillary flow of aqueous solutions. The Whatman paper strips (1×10 cm) were printed with aqueous inks containing various levels of PVAm (0-1 wt. %) and were allowed to air dry for 15 min. The PVAm treated strips were then immersed into a solution of 5-thio-2-nitrobenzoate (TNB$^-$, the colored product of the AChE catalyzed reaction), which was produced enzymatically from ATCh (final conc. 300 µM), DTNB (final conc. 500 µM), and AChE (final conc. 50 U/mL) with the sensing area above the liquid level. The retardation factor (Rf) was calculated based on the ratio of migration distance of the product (TNB$^-$) relative to the migration distance of solvent (Milli-Q water) from this lateral flow based platform.

Lateral flow and dipstick assay formats were also developed to monitor the capability of PVAm to capture and preserve the color produced from the AChE catalyzed reaction when performed on paper. In this case, Whatman (for lateral flow) or Mead cardboard dipsticks (1×10 cm) were prepared using ink jet deposited PVAm (0 or 0.5 wt %), silica (SS+30% glycerol) and AChE+DTNB (50 U/mL+500 µM in 30% glycerol, with 1 wt % Triton X-100 present in all solutions) as described above, followed by placing the sensor strip into a solution of substrate (300 µM ATCh) with the sensing area located above the liquid level (lateral flow) or within the solution (dipstick) and allowing the color to develop for 5 min. Following the assay the resulting color intensity remaining on the paper strip was monitored once a day for up to three weeks.

Measurement of AChE Inhibitors Using Bioactive Paper:

The inhibitory effects of paraoxon and AfB1 on the solid-phase biosensor were evaluated by measuring the decrease in the color intensity produced by the Ellman reaction. The PVAm/silica/AChE+DTNB/silica bioactive paper strip was first incubated with various concentrations of paraoxon solution (5 µL, 0-100 µM) or AfB1 solution (5 µL, 0-100 µM) [CAUTION: these assays should be performed in a fumehood using appropriate protective apparel], for 10 min after which 10 µL of a solution of 300 µM ATCh was deposited onto the paper strip and incubated for 5 min. The intensity was determined by analyzing a digital image with the ImageJ software as described above.

Results and Discussion

Bioink Formulation and Jetting:

Initial attempts at ink jet deposition of sol-gel based bioinks utilized silica sols to which buffered proteins had been added. While it was possible to produce protein-doped sols with relatively long gelation times, it was not possible to deposit such materials without gelation occurring in the nozzles of the ink jet cartridge. For this reason all further studies on sol-gel based inks utilized a multi-layer deposition method wherein the silica sol and buffered aqueous protein solutions were deposited from separate cartridges so as to avoid mixing prior to deposition on the paper substrate.

Both the silica and aqueous protein "inks" were optimized to allow reproducible jetting onto paper substrates. Physicochemical properties such as surface tension and viscosity are parameters that effect ink stability and ejectability. Several additives (e.g., surfactants, viscosity modifiers) are generally incorporated in the ink formulations to optimize these rheological properties. However, inappropriate additives may often negatively affect enzyme activity. Therefore, it is desirable to produce a suitable ink formulation in which the enzyme is active and at the same time produces stable and reproducible drops during jetting.

To adjust the ink surface tension (initially in the range of 60-78 mN·m$^{-1}$ without surfactant) to the printable range (30-40 mN·m$^{-1}$), Triton X-100, a mild detergent, was used as a surfactant. To determine the effect of Triton X-100 on AChE activity, a solution of AChE (50 U/mL) in Tris buffer containing 0.1 wt. % of Triton X-100 was prepared, and then the enzyme activity in solution was measured using the Ellman assay. No significant loss of AChE activity was observed in the presence of this low level of Triton X-100. Therefore, 0.1 wt. % Triton X-100 was included in all bioink formulations (e.g., AChE, sol-gel derived silica, PVAm) to get the optimum surface tension for printing (Table 1).

In order to adjust the ink viscosity (initially in the range of 1.01-1.33 cP without viscosity modifiers) to the desired value (2-10 cP), two well-known viscosity modifiers, carboxymethylcellulose sodium salt (CMC) and anhydrous glycerol, were investigated. PEG and PVA, though biocompatible, were not examined as these species have a tendency to promote macroscopic phase separation in sol-gel derived silica,[29, 30] which could result in significant protein leaching in this example.[31] These materials could be utilized when larger molecules are to be entrapped and there is less concern about leaching from the macroscopic silica matrix. CMC, a charged polymer, and glycerol were both chosen for evaluation.

Initial studies on the effects of CMC (0–0.5 wt. %) on AChE activity in solution showed that this additive led to a significant decrease in AChE activity at concentrations above 0.2 wt %. Therefore, CMC was not investigated further as a viscosity modifier. On the other hand, glycerol did not produce a decrease in AChE activity, even at levels of 30% v/v. Addition of this level of glycerol to either the SS derived silica sol or AChE-based inks also resulted in excellent drop formation and jettability, as shown in Table 1. However, all inks prepared from DGS derived silica sols using the conditions utilized herein, while jettable, resulted in poor adhesion and cracking after drying on the paper substrate. Therefore SS was used as the precursor of choice for further studies. The use of DGS may be possible be adjusting conditions using methods known in the art.

Based on the excellent ink jetting properties and the high quality of the resulting deposited materials, all inks were formulated with 30% (v/v) glycerol and 0.1 wt % Triton-X100 using sodium silicate as the silica precursor.

Figure 2:
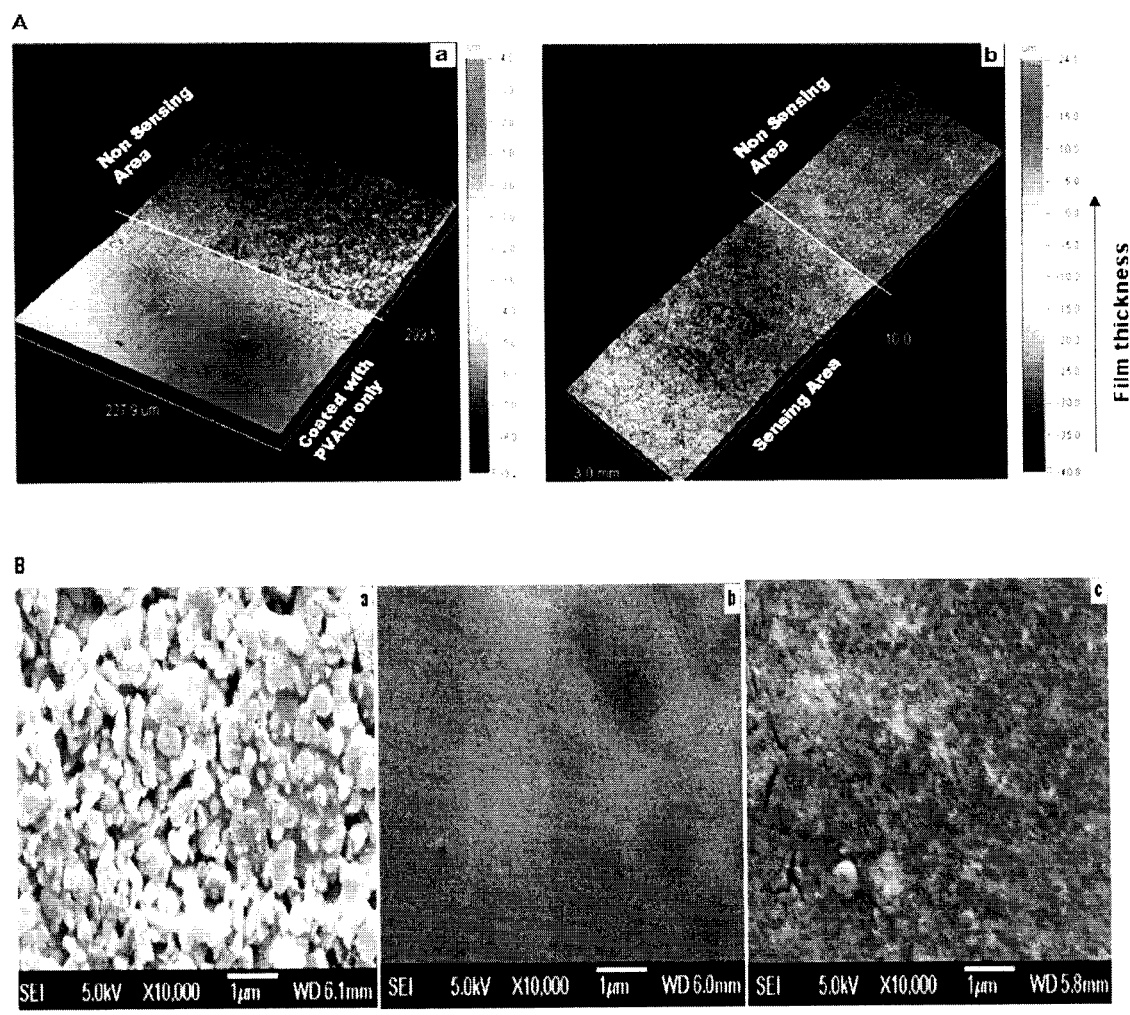
FIG. 2 shows the topography of ink jet sprayed PVAm, and AChE (50 U/mL) and DTNB (500 µM) doped sodium silicate (SS) thin films on paper. (A) Profilometry images of paper that is coated with or without PVAm only (a), and both PVAm and the silica/AChE+DTNB/silica layers (b). (B) SEM images of unmodified (a), modified with PVAm only (b), and modified with PVAm, and AChE and DTNB doped silica matrix on paper (c). Unmodified paper surface was rough, while the modified surfaces were relatively smooth.

Coating Properties:

To characterize the coatings on paper substrates, optical profilometry, contact angles and SEM images were obtained for both unmodified and modified paper substrates. FIG. 2A shows optical profilometry images of paper that is coated with PVAm only (FIG. 2A(a)), and with both PVAm and the silica/AChE+DTNB/silica layers (FIG. 2A(b)). No bioinks were printed on the non-sensing region. The profilometry results show that the PVAm layer is approximately 4 μm thick, while the sol-gel based coating had an average thickness of about 24 μm. Similar results were obtained for layers printed on glass slides, suggesting that the majority of the sensing layer was present on top of the paper rather than within the paper. This is further supported by the contact angles for PVAm coated and PVAm free Mead cardboard and Whatman paper substrates, which were approximately 112.2±1.1°, 50.1±0.3° and zero, respectively. The results indicate that the PVAm layer imparts high hydrophobicity to an already coated paper surface, and thus liquid penetration into the surface is improbable.

FIG. 2B shows SEM images of the unmodified paper (FIG. 2B(a)), PVAm coated paper (FIG. 2B(b)) and paper that was coated with both the PVAm and silica/AChE+DTNB/silica layers (FIG. 2B(c)). The unmodified paper surface is very rough (average roughness of ±972 nm) and heterogeneous, and clearly shows the presence of significant amounts of fillers (i.e., clay particles) at the surface of the paper and no evidence for paper fibers at the surface. This is consistent with the fact that the Mead paper used in this study had a protective coating. The deposition of PVAm resulted in a much smoother surface (±554 nm), and suggests that the cationic polymer likely provides a barrier coating above the filler layer onto which the silica layer is deposited, consistent with the data described above. Thus, in addition to acting as an anion capture agent, PVAm also produces a more uniform surface which may prevent enzyme leaching into the paper. Deposition of the silica/AChE+DTNB/silica layer resulted in a relatively homogeneous, crack-free layer (roughness of ±668 nm) which showed no evidence of large scale macropores (diameter>0.5 μm), consistent with the inability of glycerol to act as a porogen. Taken together, the profilometry and SEM images show that the sol-gel based ink layer is present on top of the paper, rather than penetrating through the paper. This is advantageous as it should help to retain the colorimetric signal within a thin layer rather than having it diffuse throughout the thickness of the paper, making visualization easier.

Monitoring AChE Activity and its Storage Stability:

Prior to developing the dipstick sensor, the activity of AChE was evaluated as a function of enzyme concentration (0-200 U/mL) via the Ellman assay when entrapped in sol-gel derived monolithic silica prepared from SS with 30% glycerol. The signal, measured 5 min after addition of 300 μM ATCh and 500 μM DTNB, increased linearly over the concentration range from 0-50 $U \cdot mL^{-1}$ after which the signal showed negative deviation and reached a plateau at ~100 $U \cdot mL^{-1}$. A value of 50 U/mL was chosen the best compromise between a low enzyme loading, a sufficiently high signal (>4-fold increase over background) and good long-term stability. The high activity of entrapped AChE is in agreement with previous reports showing that the enzyme is active and stable in sol-gel derived silica materials.[32]

Figure 3:
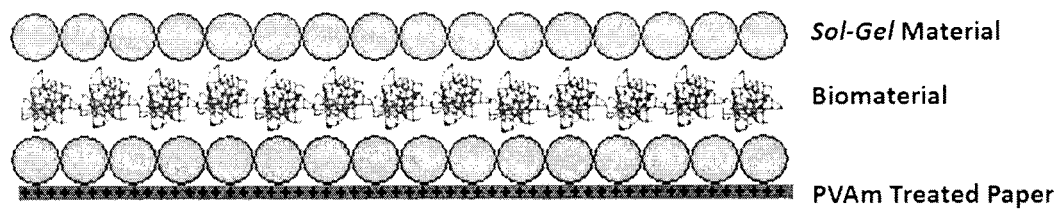
FIG. 3 shows an illustration of ink jet printing sequence of PVAm, sodium silicate (SS) based sol-gel derived silica matrix, and the tris buffer (100 mM, pH 8.0) containing enzyme acetylcholinesterase (AChE) and dithiobisnitrobenzoate (DTNB) layers on paper for development of a portable solid-phase biosensor.
Figure 4:
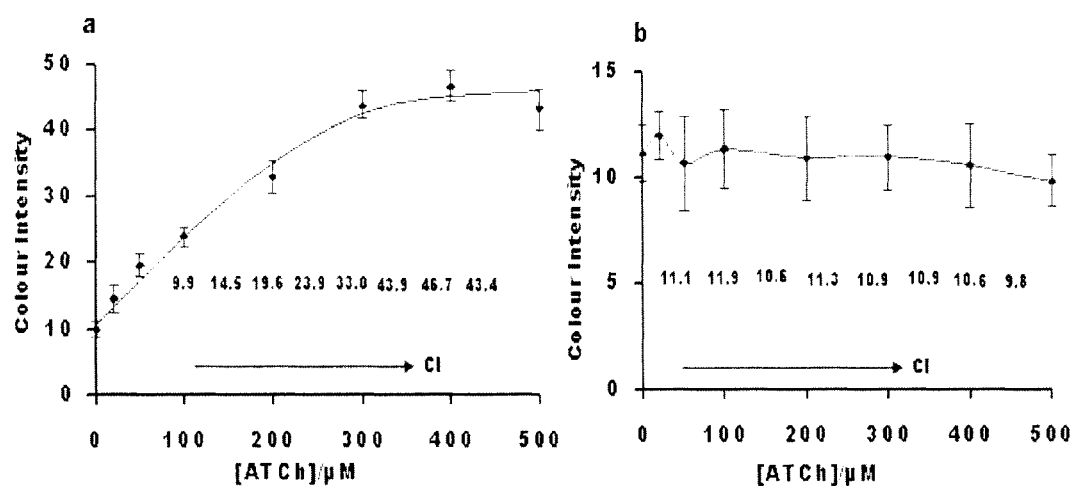
FIG. 4 shows the dose-dependent effects of acetylthiocholine (ATCh) in the presence (a) and absence (b) of AChE (50 U/mL) doped silica matrix on paper, in which PVAm (0.5 wt. %) was printed prior to printing of the silica and AChE layers. Inset is the color intensity (CI) generated at each ATCh concentration. All points are means±s.d. of five independent experiments for each concentration.

Based on the AChE activity data, a solid-phase bioactive paper based sensor was constructed by multilayer ink jet printing of several bioinks in the order: PVAm, silica, 50 U/mL AChE+500 μM DTNB, silica using the compositions listed in Table 1 with 30% glycerol added to all inks except PVAm. This resulted in a layered system as shown in FIG. 3. The effects of adding varying levels of ATCh over the bioactive paper sensor are shown in FIG. 4a (a separate paper sensor is used for each ATCh concentration). Here it is seen that as the concentration of ATCh increases so too does the color intensity, recorded 5 min after addition of the substrate over the sensing area. The color intensity saturated at a level of ~300 μM ATCh and suggested a $K_M$ of ca. 150 μM, which is in good agreement with previous literature reports.[33] The color intensity was about four-fold higher than that of a negative control (absence of ATCh but with AChE present).

To ascertain whether or not the supporting silica or PVAm materials degraded DTNB or ATCh, a similar experiment was conducted using the same inks as above but with AChE absent from the aqueous ink layer. As shown in FIG. 4b, the responses remained at the baseline signal upon addition of varying levels of ATCh and were similar to signals obtained from control experiments performed in the absence of substrate. Thus, these results confirm that the change in the color intensity is due to the AChE catalyzed hydrolysis of ATCh to TCh which then reduces DTNB to $TNB^-$. Furthermore, this result shows that the AChE is able to withstand the shear forces associated with ink jet deposition and remains active when deposited between silica layers on a paper substrate.

The long-term stability AChE within the layered coating on the paper substrate was also investigated. Results demonstrated that the enzyme retained >95% of its initial activity over a period of at least two months when stored at 4° C., indicating that both the enzyme and the DTNB reagent remained viable during storage. The observed stability of the enzyme when entrapped in silica shows that the bioactive paper sensor should have a sufficient shelf-life to allow storage and shipping.

To further assess the "sandwich architecture", two controls were done to assess the effects of both the PVAm and the silica layers on AChE activity and stability. In the first case, the enzyme was printed directly onto PVAm without silica. In this case, the enzyme showed activity on day 1, but no activity by day 2, likely owing to dehydration and/or strong electrostatic interactions between the enzyme and the cationic polymer which caused denaturation. In the second case, the enzyme+DTNB solution was printed onto the silica material that covered the PVAm layer, but the silica overlayer was not added. Such sensors showed activity that was comparable to the "sandwich architecture" device after 2 days, however, after prolonged storage the "non-sandwich" device produced significantly lower signal as a result of enzyme inactivation. Additionally, using this approach (i.e. no top silica layer), it was not possible to employ the sensor for dip-stick assays as the enzyme readily desorbed from the paper/silica surface.

Effects of PVAm on Biosensor Performance:

Two problems that were initially encountered when carrying out the Ellman assay using sol-gel entrapped AChE on the paper-based sensor were dispersion of the colored product over a large area, leading to lower color intensity, and loss of color intensity with time. The former issue is expected based on the ability of the small molecular weight colored product to readily move through the pores of the silica matrix and thus leach out of the sensing area. The latter issue appears to be related to a secondary chemical reaction of the $TNB^-$ with either the silica or some component in the paper, causing complete loss of color intensity over a period of a few days (see below). This makes storage of used sensors for future reference impossible. Therefore, trapping and preserving the color within a finite region was desirable to obtain the highest output signals and keep the signal stable over long periods of time. It was reasoned that the best method for capturing the anionic colored product was to introduce a cationic polymer, PVAm, onto the surface of the paper. This polymer has recently been shown to be useful for enhancing the wet strength of paper,[34] and thus should be compatible with the substrate, and binds strongly to silica,[35] which should promote adhesion of the silica overlayer and not interfere with this coating layer. However, introduction of PVAm directly to a silica sol causes very rapid gelation owing to base catalyzed condensation, and hence this polymer was printed on paper prior to printing of the silica sol to avoid this problem.

Figure 5:
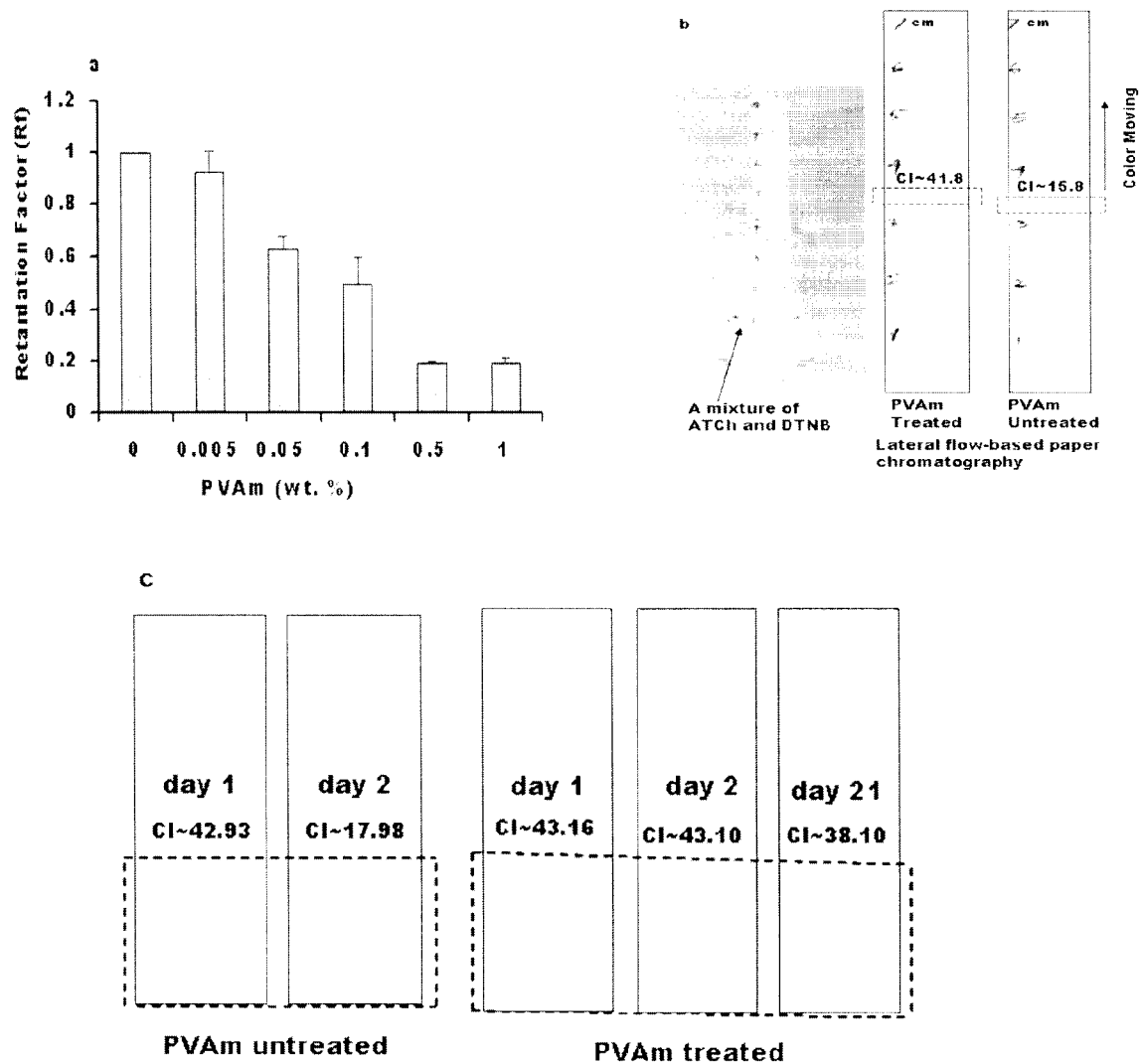
FIG. 5 shows the effects of cationic PVAm on entrapment as well as preservation the anionic TNB in lateral flow-based paper chromatographic system. (a) The values of retardation factor (Rf) for anionic TNB in Milli-Q water in the presence of indicated PVAm levels. (b) Colour intensity (CI) due to elution of ATCh (300 µM, final conc.) in the lateral flow based platform. The areas within the dashed boxes were printed without (control) and with PVAm (0.5 wt. %) followed by printing of AChE (50 U/mL). PVAm concentrates the reaction product, the yellow TNB anion, while in the control experiment, the yellow TNB anion is dispersed over a large area. (c) Cardboard dipstick with ink jet printed PVAm or control (no PVam) and silica/AChE/DTNB/Silica layers after being immersed in ATCh solution. Both materials show an initial color response, but only the PVAm (0.5 wt %)-treated paper retains the reaction product (a yellow TNB⁻) for a period of 3 weeks, while the PVAm untreated paper failed to retain the color.

To examine the effect of PVAm on sensor performance, a series of experiments were performed. Initial studies utilized a paper chromatographic set-up (lateral flow-based) to assess the ability of PVAm coatings containing varying levels of the polymer to retain the anionic product. For this purpose, hydrophilic Whatman 1 paper strips were printed with solutions containing 0-1 wt % of PVAm and a solution of $TNB^-$ (produced by mixing 300 µM ATCh, 500 µM DTNB and 50 U/mL of AChE in Milli-Q water) was allowed to travel up the paper via capillary action. FIG. 5a shows the values of retardation factor (Rf), a measure of the relative mobility of $TNB^-$, as a function of PVAm concentration and demonstrates that the Rf values decreased with increasing levels of PVAm up to a level of 0.5 wt % of PVAm. Thus, 0.5 wt % PVAm was utilized in further studies to trap the negatively charged analyte.

FIG. 5b shows the colour intensity due to elution of Ellman's solution using the lateral-flow based paper chromatographic system. The areas within the dashed boxes were either treated or not treated (control) with 0.5 wt % PVAm, deposited via ink jet spraying onto Whatman 1 paper, followed by printing of the silica/AChE+DTNB/silica layers over the same area. It was found that PVAm was able to trap and concentrate the $TNB^-$ reaction product without diminishing the color intensity, while the unmodified paper (control) failed to trap the yellow color. As a result, the intensity of the yellow color was much higher when PVAm was present (0.25×1 cm), which should produce a better detection limit when using the paper to sense AChE substrate or inhibitors.

The capability of PVAm to preserve the $TNB^-$ product for an extended period of time was also investigated. For this, Mead cardboard dipsticks were coated with the PVAm ink followed by silica/AChE+DTNB/silica ink layers and the dipsticks were immersed into a solution of 300 µM ATCh for 1 min. Images were obtained 30 min or 24 h after exposure to ATCh. A control sample was also tested in which the PVAm underlayer was not present. FIG. 5c shows images of the dipsticks under the different testing conditions, and clearly demonstrates that the PVAm is able to retain the yellow product while untreated paper causes the yellow color to disappear almost completely after only 24 h. Further testing revealed that the PVAm layer was capable of retaining the color for at least three weeks. Thus, the bioactive paper strips can be stored for future reference.

Neurotoxin Measurement Based on AChE Inactivation:

Neurotoxins such as paraoxon and aflatoxin B1 are well known inactivators of acetylcholinesterase.[27,36,37,38] The ability to detect these compound using the ink jet printed AChE-based paper sensor was investigated by using an over-spotting method wherein small volumes of reagents were added to the sensing area directly. In this case, as little as 10 µL of solutions containing various concentration of paraoxon or AfB1 could be tested by applying them onto the sensing area of the strip, incubating for 10 min at room temperature, adding 10 µL of a solution containing 300 µM ATCh and finally measuring the color intensity after 5 min using a digital camera and image processing software. FIG. 6a shows the dose-dependent inhibition effects of paraoxon, while FIG. 6b shows the semi-logarithmic plot of color intensity, corresponding to the same experiments, demonstrating an $IC_{50}$ in the range of 1 µM and a detection limit (S/N=3) of ca. 100 nM. FIG. 7a and FIG. 7b show the dose-dependent inhibition responses and a semi-logarithmic plot of color intensity, respectively, for AfB1, and show that the $IC_{50}$ in this case is ca 100 nM, with a LOD of ~30 nM. A comparison of the responses obtained at 100 nM of either paraoxon or AfB1 show that AfB1 is a more potent inhibitor (~45% inhibition vs. ~25% inhibition for paraoxon), in agreement with previous studies.[28,33,39]

Figure 6:
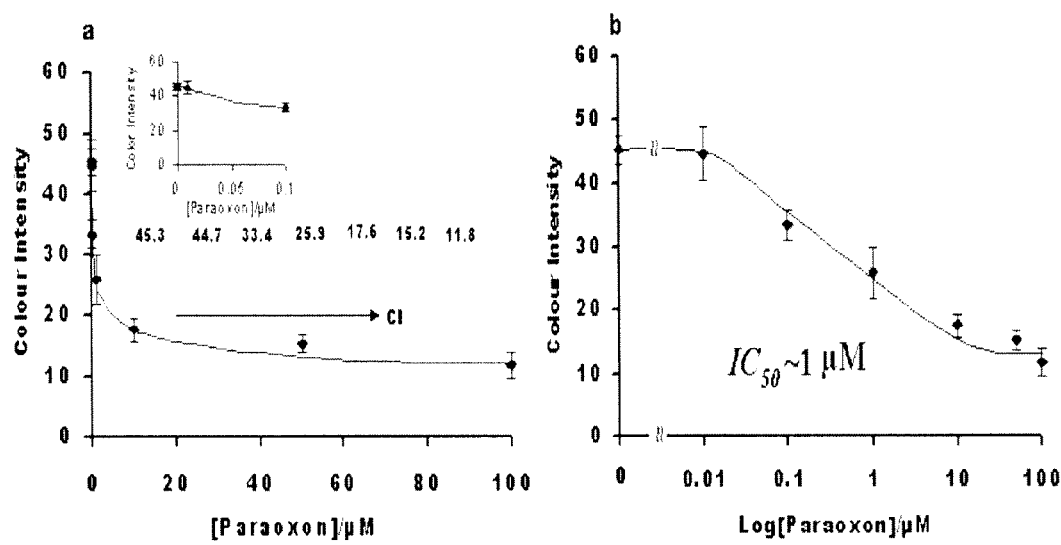
FIG. 6 demonstrates the dose-dependent inhibition of acetylcholinesterase (AChE) by various concentrations of paraoxon (a). Insets are the color intensity (CI) at each paraoxon concentration and dose-dependent inhibition responses with the lower levels of paraoxon. (b) Semi log plot of data in panel (a). PVAm and AChE (50 U/mL) and DTNB doped silica layers were printed on paper before conducting experiments. All points are means±s.d. of five measurements for each concentration.
Figure 7:
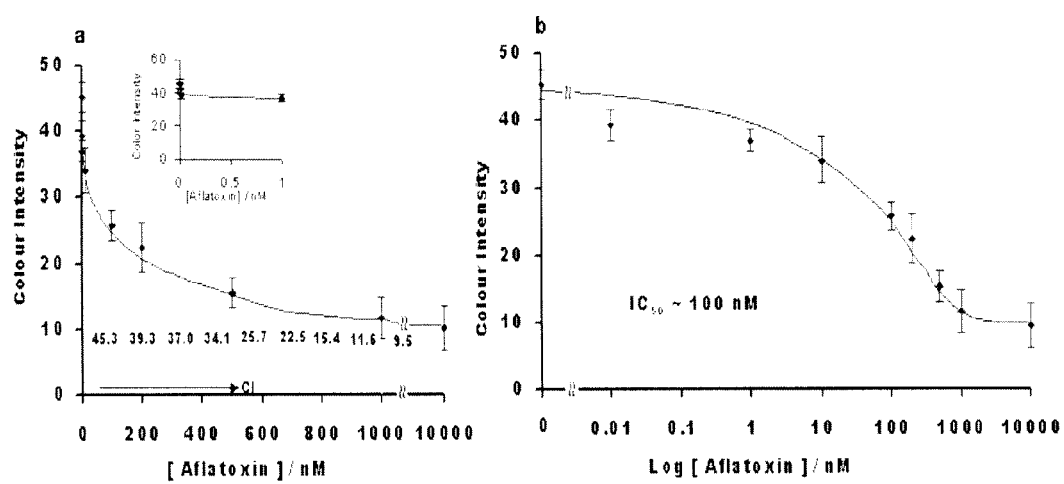
FIG. 7 shows: (a) Dose-dependent inhibition effects of aflatoxin B1 on AChE activity. Insets are the color intensity (CI) at each aflatoxin B1 concentration and dose-dependent inhibition responses with the lower levels of aflatoxin B1; (b) Semi log plot of the data shown in Panel (a). Data are means±s.d. of five independent measurements for each concentration.

The insets for FIGS. 6 and 7 show the images of the paper strips at each inhibitor concentration, and clearly demonstrate that detection of the inhibitors is possible using the naked eye. This is an advantageous aspect of the bioactive paper strips, as this permits the use of the test strips directly in the field and eliminates the need for sophisticated instrumentation. The presence of a simple colorimetric readout also enables rapid imaging and transmission to a central lab for further quantitative analysis using a simple cell phone camera combined with e-mail or MMS messaging.[3,5,7] Hence, rapid, on-site qualitative or quantitative analysis of organophosphates or aflatoxins should be possible using this bioactive paper platform.

Example 2

Reagentless Bioactive Paper-Based Lateral Flow Sensor for Detection of Pesticides Reagents:

All chemical from commercial sources were of analytical grade. Sodium silicate solution (~14% NaOH, ~27% $SiO_2$), dowex 50WX8-100 ion-exchange resin, acetylcholinesterase (AChE, from *electrophorus electricus*, EC 3.1.1.7), Triton X-100, the pesticides including both organophosphate (OP) (e.g., paraoxon and malathion), and carbamate (CM) (e.g., carbaryl and bendiocarb) were obtained from Sigma-Aldrich (Oakville, ON, Canada). The indophenyl acetate (IPA) was purchased from Pealtz & Bauer, Inc (USA). Polyvinylamine (PVAm; 1.5 MDa) was obtained from BASF (Mississauga, Canada), as a gift. Anhydrous glycerol was purchased from Fluka BioChemika Ultra (UK). Distilled deionized water was obtained from a Milli-Q Synthesis A10 water purification system.

Solutions Preparation:

Stock solutions of the IPA, bendiocarb, carbaryl, paraoxon and malathion were made up daily and were not used for more than 3 h after preparation to minimize the potential for hydrolysis. A mixture of Tris buffer (10 mM, pH 6.8) and 5% methanol (Sigma) was used for dissolving bendiocarb, carbaryl, malathion, and paraoxon while a mixture of Tris buffer (10 mM) with pH 8.0 and 5% methanol (Sigma) was used for dilution of IPA. These solvents not only aid in dissolution of the AChE inhibitors, but also enhance the affinity of pesticides for binding to AChE. Furthermore, this level of organic solvent has been shown not to affect the stability of AChE in any way. Note that experiments conducted without organic solvent present produced significantly lower detection limits for pesticides. Therefore, for practical applications, it is recommended that low levels of organic solvents be used not only for dissolution purposes but also to enhance sensitivity. Distilled deionized water ($ddH_2O$) was used to dissolve PVAm. All other solutions were prepared using Tris buffer (10 mM, pH 8) if not otherwise stated. CAUTION: Both carbamate (e.g., bendiocarb, carbaryl) and organophospate (e.g., paraoxon, malathion) pesticides are extremely toxic. These materials should be handled with gloves and used in a fumehood.

Sol-Gel Material Preparation:

A biocompatible sol-gel precursor, sodium silicate (SS) was used to prepare sols for both enzyme and IPA entrapment and printing onto paper. SS sols were prepared by mixing 10 mL of $ddH_2O$ with 2.59 g of sodium silicate solution (pH~13) followed by addition of 5 g of Dowex cation exchange resin to replace $Na^+$ with $H^+$. The mixture was stirred for 30 seconds to reach a final pH of ~4, and then vacuum filtered through a Büchner funnel. The filtrate was then further filtered through a 0.45 μm membrane syringe filter. These sols were used to formulate silica-containing inks as described below.

Fabrication of Reagentless Bioactive Paper-Based Lateral Flow Sensor:

A section of Whatman #1 paper was cut into small pieces (1×10 cm) in which enzyme, AChE and substrate, IPA were entrapped in the two different regions (e.g., sensing and substrate regions) following the sequences of PVAm (0.5 wt %)/silica/AChE (500 U/mL)/silica and silica/IPA (3 mM)/silica, respectively by using either ink jet printing (using a piezoelectric ink jet printer (DMP-2800), Fujifilm Dimatix, Inc, Japan) or over spotting, as shown in FIG. 8(b). However in the case of ink jet printing, all inks were modified with respect to viscosity and surface tension similarly as described in Example 1. The sensor was then allowed to air dry at room temperature. Two control experiments: (1) a buffer that did not contain AChE was entrapped between the silica layers in the sensing region, and (2) a buffer that did not contain IPA was entrapped between the silica layers in the substrate region. Other controls involved entrapment of AChE directly onto the PVAm underlayer without a silica coating, and entrapment of AChE onto PVAm/silica without printing a silica overlayer.

Optimization of Reagentless Paper-Based Lateral Flow Assay Platform:

The lateral flow assay format was optimized with regard to the PVAm levels, the pH level of Tris buffer (10 mM) that was used to dissolve the enzyme substrate, concentration of substrate, and the concentration of the enzyme.

In Example 1, a lateral flow-based paper chromatographic system was developed to investigate the effect of the PVAm underlayer on the solid phase sensor performance where the PVAm treated strips were immersed into a solution of 5-thio-2-nitrobenzoate ($TNB^-$, the colored product of the AChE catalyzed reaction), which was produced enzymatically from ATCh (final conc. 300 μM), DTNB (final conc. 500 μM), and AChE (final conc. 50 U/mL) with the sensing area above the liquid level. The retardation factor (Rf) was calculated based on the ratio of migration distance of the product ($TNB^-$) relative to the migration distance of solvent (Milli-Q water) from this lateral flow based platform. Therefore, the PVAm level was not optimized further to entrap as well as preserve the anionic dye (indophenoxide), hence, the previously optimized PVAm level was taken as an optimum value in this example.

The effect of pH of the Tris buffer on IPA stability was investigated in solution. For this, IPA (3 mM) was dissolved with Tris buffer having different levels of pH (4~9.5). 80 μL of IPA solution and 20 μL of AChE (final conc 500 U/mL) were then mixed into a 96-well plate and incubated for 5 min to allow color development. The absorbance at 640 nm was then measured using a TECAN Safire microwell plate reader.

Prior to monitoring AChE activity on paper, the activity of AChE as a function of enzyme concentration and chromogenic AChE substrate, IPA concentrations were optimized. Different concentrations of AChE (0~1500 U/mL) were entrapped in SS+30% glycerol in a 96 well plate (total volume of 80 μL). 20 μL of IPA (0~5 mM) was then added into each well and incubated for 5 min to allow color development. The absorbance at 640 nm was then measured using a TECAN plate reader.

The AChE activity on the bioactive paper strip was evaluated by measuring the color intensity produced by the enzymatic hydrolysis of IPA. The performance of the sensor under optimized conditions can be assessed in two ways: (1) directly (normal lateral flow-based chromatography) without incubating the contaminated sample, and (2) inverted lateral flow-based chromatography with incubation of the sample. For the latter case, after incubation 5 min at room temperature, the sensor was inverted again and immersed into $dH_2O$ for bringing up IPA by lateral flow action into sensing area of the strip above the liquid level.

The color intensity of the sensing areas was quantified by obtaining a digital image (Canon A630, 8.0 MegaPixel operated in automatic mode with no flash and with the macroimaging setting on) and using ImageJ™ software to analyze the jpeg images. ImageJ™ software uses a 256 bit color scale and for our image processing the images were inverted so that white corresponded to a color intensity of 256 and black corresponded to zero. Based on this, increases in the amount of blue color cause an increase in color intensity of our reagentless sensor strips. To account for variations in color intensity owing to differences in environmental illumination, a background subtraction (color intensity of the paper surface closest to the sensing area) was done for each data point.

Measurement of Pesticides Using Reagentless Paper-Based Lateral Flow Platform:

The inhibitory effects of carbamate (e.g., bendiocarb, carbaryl) and organophosphate (e.g., paraoxon, malathion) pesticides on the reagentless paper-based sensor were evaluated by measuring the decrease in the color intensity produced by enzymatic hydrolysis of IPA. The sensing area of the bioactive paper strip was first incubated with various concentrations of either carbamate or organophosphate solution for 5 min following the inverted lateral flow procedure as described above. The sensor was then inverted again and immersed into dH$_2$O to bring up IPA by lateral flow action into the sensing area of the strip above the liquid level. The color intensity was determined by analyzing a digital image with the ImageJ software as described above.

Matrix Effect in the Analysis of Paraoxon into Foods:

The matrix effects in the analysis of paraoxon in drinking milk (2%, pH 7.2) and apple juice (pH 3.6) samples were investigated. Several standard paraoxon solutions (0~10 μM) were mixed into both milk (10 mL) and apple juice (10 mL) samples. The developed reagentless sensor was immersed inversely into each paraoxon containing samples. The sensor was incubated for 5 min and the inhibition of AChE was tested following the inverted lateral flow procedure as described above. The pH of the apple juice was adjusted between 7~8 using a few drops of 1N NaOH before doing experiment.

Analysis of Paraoxon in Real-Life Samples:

Different concentrations of paraoxon solution (0~50 mM) was sprayed on apple and head lettuce. After air dry, the deposited paraoxon samples were collected using a cotton-swab and transferred into 2 mL dH$_2$O; this solution was tested following the inverted lateral flow procedure as described above with 5 min incubation using our developed reagentless sensor.

Storage Stability of the AChE- and IPA-Immobilized Strip:

The long-term stability of the enzyme and enzyme substrate, IPA entrapped on the paper strip was evaluated over a period of 12 weeks with the paper strip stored at 4° C. The performance of the stored sensor was also examined by assaying for paraoxon. The assay conditions were the same as those described above.

Result and Discussion

Figure 8:
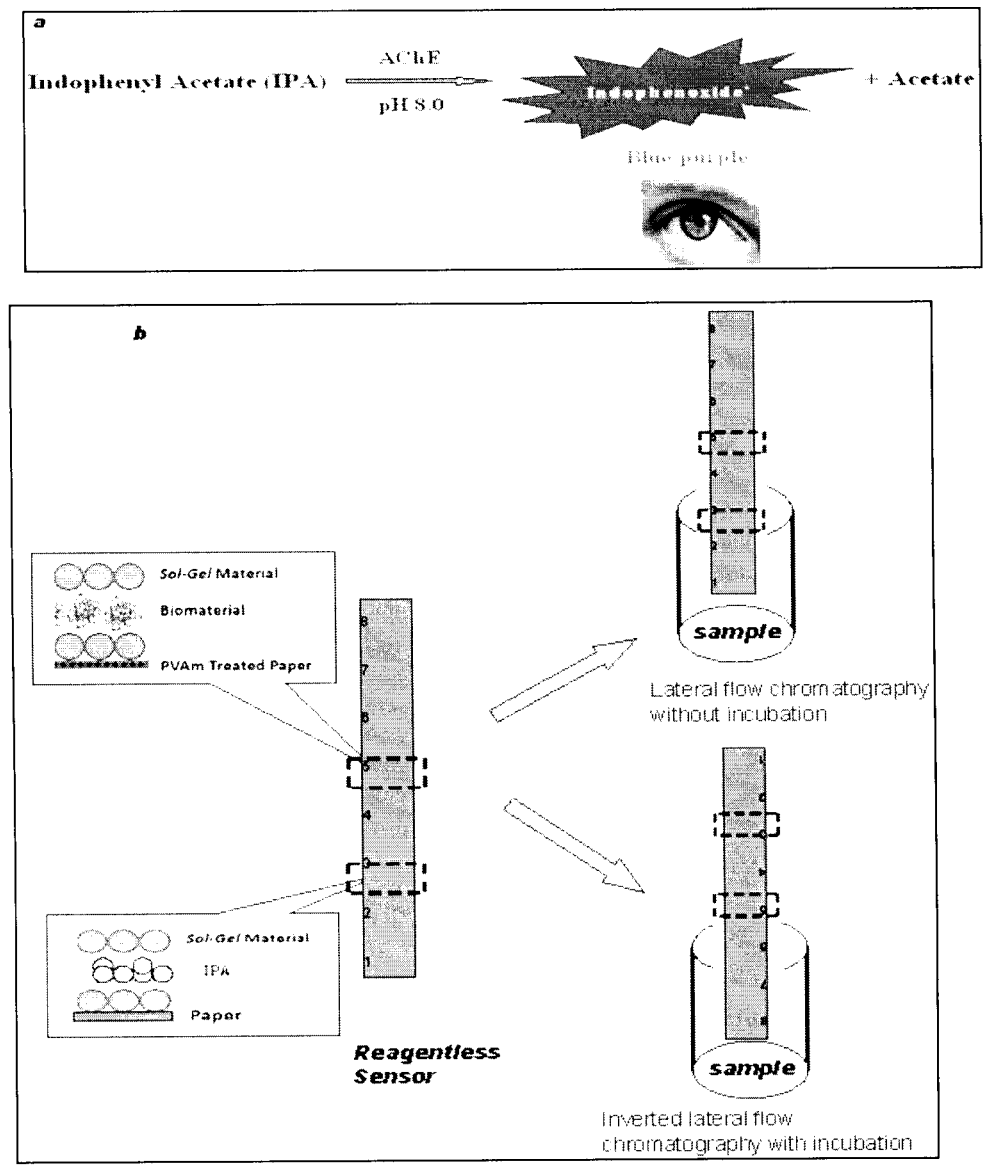
FIG. 8 shows a schematic diagram of the detection principle of the Indophenyl Acetate (IPA)-based colorimetric assay. Acetylcholinesterase (AChE) hydrolyzes the red-yellow colored substrate IPA at a basic condition (pH 8.0) and forms indophenoxide anion, which is blue-purple in color. (b) Schematic illustration for the development of the reagentless bioactive paper-based lateral flow sensor in which AChE and IPA were entrapped in the two dashed boxes regions of Whatman 1 paper strip (1×10 cm) following the sequences of PVAm/silica/AChE/silica and silica/IPA/silica, respectively by using either the ink jet printing or over spotting. The sensor then can be used two different ways: (1) directly (normal lateral flow-based chromatography) without incubating the contaminated sample, and (2) inverted lateral flow-based chromatography with incubation the sample.

Optimization of the Reagentless Lateral-Flow Assay Format:

The concept of the reagentless lateral flow assay is shown in FIG. 8. FIG. 8*a* shows the IPA reaction, which results in a color change from yellow to blue. FIG. 8*b* shows a schematic of the ink jet layers used in the assay, with AChE or IPA entrapped between two silica layers in distinct regions of the paper-based device. Flow of liquid moves the IPA up to the AChE region and produces a product that can be captured by a PVAm underlayer. The assay can be done directly or in an "inverted" format. In the first case an inhibitor is present in the test solution and is flowed through the IPA region to the AChE region. In the second case, the test solution is flowed from the opposite end of the device into the AChE region where it is incubated. After a set amount of time the other end is placed into the test solution and the IPA is moved into the AChE region. This allows compounds that are slow inhibitors of the enzyme to be detected.

Prior to developing an efficient reagentless lateral flow based paper sensor with high sensitivity and rapid response, all the parameters, such as PVAm levels, the pH of the buffer, concentration of substrate, and the concentration of the enzyme were optimized.

Figure 9:
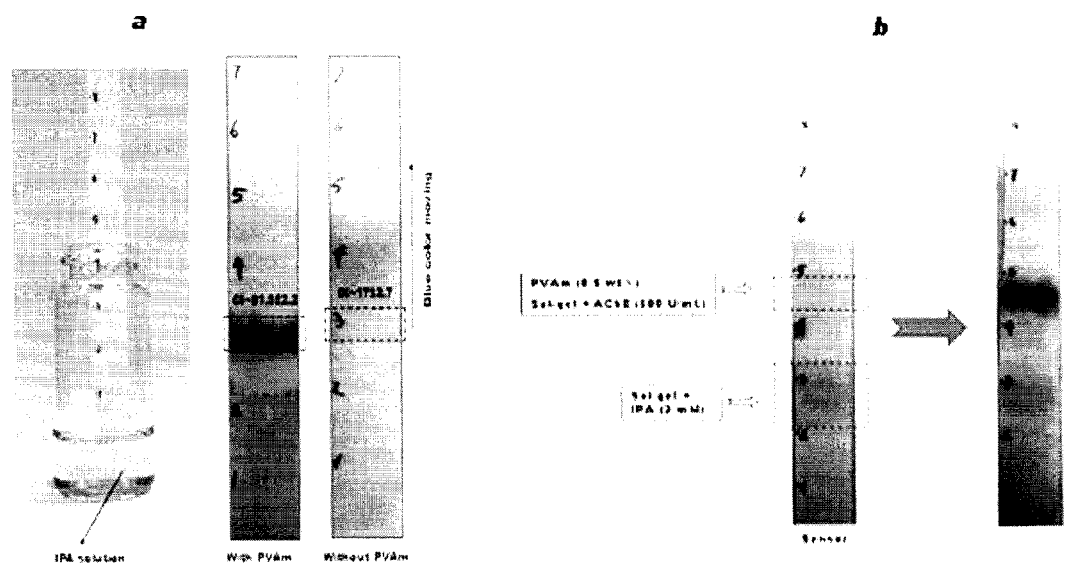
FIG. 9 shows the effects of cationic PVAm on entrapment of indophenoxide anion in lateral flow-based paper chromatographic system. Colour intensity (CI) due to elution of IPA (3 mM, final conc.) in the lateral flow based platform. The areas within the dashed boxes were printed/over spotted without (control) and with PVAm (0.5 wt. %) followed by printing/overspotting of AChE (50 U/mL). PVAm concentrates the reaction product, the blue indophenoxide anion, while in the control experiment; the blue indophenoxide anion is dispersed over a large area. (b) Proof of concept for the development of reagentless bioactive paper-based lateral flow platform, in which the sensor was dipped into dH₂O to bring up the IPA reagent into sensing region for the generation of blue color.

Trapping and preserving the color (that is produced during enzymatic hydrolysis of substrate) within a finite region of the sensor is advantageous to obtain the highest output signals and keep the signal stable over long periods of time. In Example 1, a lateral flow-based paper chromatographic system was developed to investigate the effect of the PVAm underlayer on the solid phase sensor performance where the PVAm (0~1 wt %) treated strips were immersed into a solution of 5-thio-2-nitrobenzoate (TNB$^-$, the colored product of the AChE catalyzed reaction), which was produced enzymatically from ATCh (final conc. 300 μM), DTNB (final conc. 500 μM), and AChE (final conc. 50 U/mL) with the sensing area above the liquid level. The retardation factor (Rf) was calculated based on the ratio of migration distance of the product (TNB$^-$) relative to the migration distance of solvent (Milli-Q water) from this lateral flow based platform. The capability of PVAm to preserve the TNB$^-$ product for an extended period of time was also investigated. Therefore, the PVAm level was not optimized further to entrap as well as preserve the anionic dye (indophenoxide) in this Example. Here, it was determined whether or not the previously optimized PVAm level (0.5 wt %) was enough to trap as well as concentrate the blue color product (indophenoxide$^-$). FIG. 9(*a*) shows the color intensity (CI) due to elution of IPA (3 mM, final conc.) in the lateral flow based platform. The areas within the dashed boxes were either treated or not treated (control) with 0.5 wt % PVAm, deposited via ink jet spraying/overspotting onto Whatman #1 paper, followed by printing/overspotting of the silica/AChE (500 U/mL)/silica layers over the same area. The data indicated that the 0.5 wt % PVAm level was able to trap and concentrate the indophenoxide$^-$ reaction product efficiently without diminishing the color intensity, while the unmodified paper (control) failed to trap the blue color. As a result, the intensity of the blue color was much higher when PVAm was present, which should produce a better detection limit when using the paper to sense AChE substrate or inhibitors. Based on these data, a reagentless lateral-flow based paper sensor was constructed. FIG. 9(*b*) represents a reagentless bioactive paper platform, in which AChE and IPA were entrapped into two different regions and then the sensor was dipped into dH$_2$O to bring up the IPA reagent by capillary action into sensing region for the generation of blue color due to enzymatic hydrolysis of substrate. This result indicates a proof of concept study for the development of reagentless bioactive lateral-flow paper based sensing platform.

Indophenyl acetate (IPA) is a well known pH-sensitive chromogenic substrate for AChE. Therefore, the pH of the buffer effects IPA stability as well as the effective enzymatic-substrate reaction.

AChE hydrolyzes the substrate IPA at pH 8.0 to produce a highly blue colored product. Preliminary studies on the effects of pH (4~9.5) of the Tris buffer (10 mM) on IPA stability in solution showed that at levels slightly lower than pH 8.0 gives considerably lower absorbance readings for the enzyme-substrate reaction product, while at slightly higher levels than pH 8.0, auto hydrolysis of IPA occurred even in the absence of AChE. In addition, the maximum absorbance of the reaction product was saturated at pH 8.0. Therefore, pH 8.0 was considered as an optimum value for the Tris buffer (10 mM), which was used to dissolve IPA in this study. The observed stability of IPA at buffer pH 8.0 is in agreement with previous reports.

Figure 10:
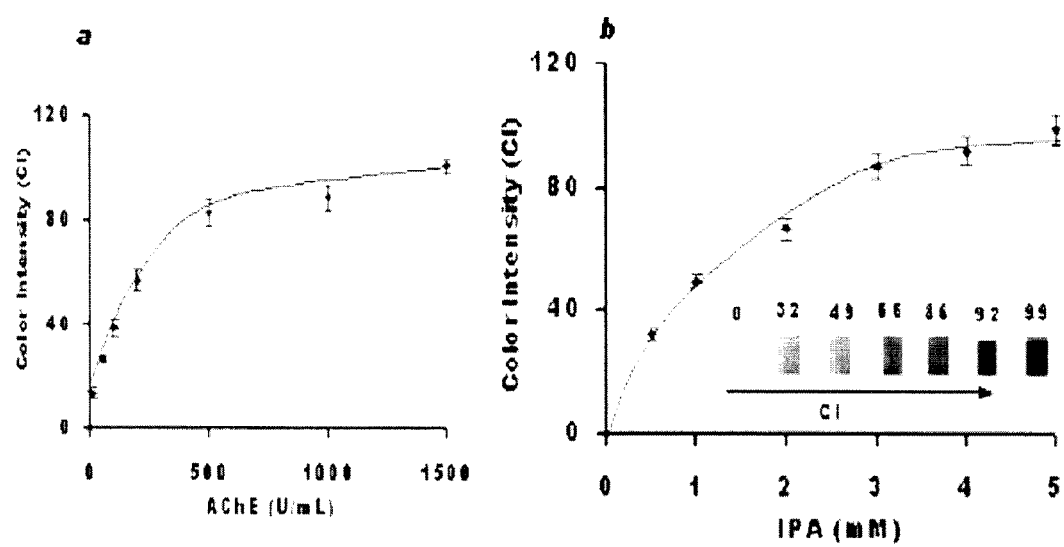
FIG. 10 shows the optimization of [AChE] for the development of paper-based lateral flow sensor. (a) Color intensity at different [AChE] in the presence of IPA (3 mM) on paper (b) Effects of [IPA] in the presence of AChE (500 U/mL) doped SS sol-gel matrix on paper. All points are means±s.d. of four measurements for each concentration

Prior to monitoring AChE activity on paper, both the activity of AChE as a function of enzyme concentration and chromogenic AChE substrate, IPA concentrations (0-5 mM) were optimized via the IPA-based colorimetric assay when entrapped in sol-gel derived monolithic silica prepared from SS with 30% glycerol in a 96-well plate. With increasing concentration of AChE solution (0-1500 U/mL), the signal, measured 5 min after addition of 3 mM IPA, increased linearly over the concentration range from 0-500 U·mL$^{-1}$ after which the signal showed negative deviation and reached a plateau at ~1500 U·mL$^{-1}$. Similarly, with increasing concentration of IPA (0~5 mM), the color intensity, measured after addition of 500 U/mL AChE, increased linearly over the concentration range from 0-3 mM. The concentrations of AChE and IPA were optimized further over the reagentless lateral flow based paper sensor. For this, a reagentless lateral-flow based paper sensor was constructed by entrapment of AChE and IPA in the two different regions (e.g., sensing and substrate regions) following the sequences of PVAm (0.5 wt %)/silica/AChE/silica and silica/IPA/silica, respectively by using either ink jet printing or over spotting. This resulted in a layered system as shown in FIG. 8(b). The effects of immobilization of different concentrations of AChE over the reagentless paper sensor are shown in FIG. 10(a) (a separate paper sensor is used for each AChE concentration). Almost similar responses were observed for both the cases (optimization of AChE in plate reader and on paper). Therefore, a value of 500 U/mL was chosen the best compromise between a low enzyme loading, a sufficiently high signal (>7-fold increase over background) and good long-term stability. The high activity of entrapped AChE is in agreement with previous reports showing that the enzyme is active and stable in sol-gel derived silica materials.[40] The effects of entrapment varying levels of IPA over the bioactive paper sensor are shown in FIG. 10(b) (a separate paper sensor is used for each IPA concentration). Here it is seen that as the concentration of IPA increases so too does the color intensity. The color intensity saturated at a level of ~3 mM IPA and suggested a $K_M$ of ca. 1.5 mM, which is similar to that of plate reader. Therefore, the most suitable concentration of enzyme substrate selected by compromise was 3 mM for IPA. Moreover, the observed $K_M$ value (1.5 mM) in sol-gel material for the present study is sufficiently higher than the literature value (~0.70 mM in solution). This high $K_M$ value is probably due to the diffusion limitation of IPA to come into contact with AChE, which is entrapped within sol-gel material (solid phase) instead of solution. The color intensity was about seven-fold higher than that of a negative control (absence of IPA but with AChE present).

To ascertain whether or not the supporting silica or PVAm materials degraded IPA, a similar experiment was conducted using the same inks as above but with AChE absent from the aqueous ink layer of the sensing region. The responses remained at the baseline signal upon addition of varying levels of IPA and were similar to signals obtained from control experiments performed in the absence of substrate. Thus, these results confirm that the change in the color intensity is due to the enzyme catalyzed hydrolysis of IPA to idophenoxide anion (blue color product). Furthermore, this result shows that both the AChE and IPA remain active when deposited between silica layers on a paper substrate.

Performance of Reagentless Lateral-Flow Assay System:

Both carbamate (e.g., bendiocarb, carbaryl) and organophosphate (e.g., paraoxon, malathion) pesticides are well known inactivators of acetylcholinesterase.[27,36,37,38] The ability as well as the performance to detect these compounds using the developed reagentless lateral-flow based paper sensor was investigated by two ways: a) by dipping the test strip directly into solutions containing various concentrations of pesticides without incubating at room temperature, and b) by immersion of the test strip inversely into solutions containing various concentrations of pesticides and allowing them to rise up into the sensing area. The sensor was incubated for 5 min and the inhibition of AChE was tested following the inverted lateral flow procedure as described in above. A decrease in color formation (due to enzymatic hydrolysis of IPA at pH 8.0 to produce a highly blue colored product) indicates the presence of an inhibitory substance. It was found that the detection limit of these pesticides was considerably lower for the first case in comparison with the second one. Therefore, inverted lateral flow system with incubation was used for all subsequent experiments to assess pesticide detection in this study.

Figure 11:
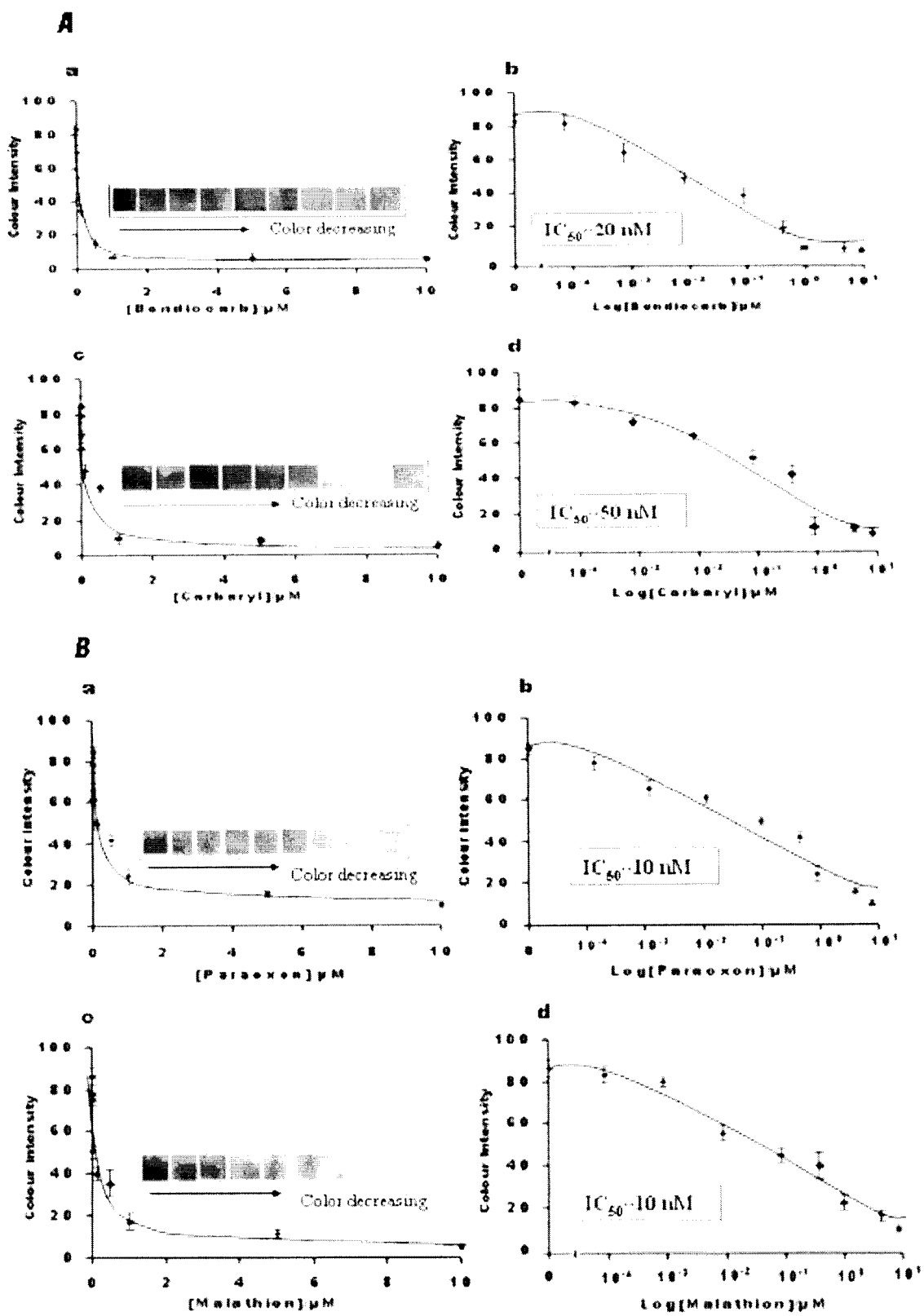
FIG. 11 shows the dose-dependent inhibition of acetylcholinesterase (AChE) by various concentrations of carbamate (A) and organophosphate (B) pesticides. A-(a) and A-(c) show the dose-dependent inhibition responses of bendiocarb and carbaryl, respectively. A-(b) and A(d) show the semi log plots of data in panels A-(a) and A-(c), respectively. B-(a) and B-(c) show the dose-dependent inhibition responses of paraoxon and malathion, respectively. B-(b) and B-(d) show the semi log plots of data in panels B-(a) and B-(c), respectively. All points are means±s.d. of four measurements for each concentration

FIGS. 11A-(a) and A-(c) show the dose-dependent inhibition responses of two carbamate pesticides such as bendiocarb and carbaryl, respectively, while FIGS. 11A-(b) and A(d) show the semi log plots of data in panels A-(a) and A-(c), respectively. The data suggest that increasing concentrations of both bendiocarb and carbaryl progressively inhibit the activity of AChE. The apparent saturated inhibition concentrations for bendiocarb and carbaryl were found to be around 1 μM and 5 μM, respectively. On the basis of these results, the calculated $IC_{50}$ values for bendiocarb and carbaryl to inhibit the activity of AChE were 20 nM and 50 nM, respectively. In addition, the detection limits (S/N=3) of bendiocarb and carbaryl were found to be ca. 10 and 100 nM, respectively. The results demonstrate that bendiocarb is a more potent pesticide for blocking AChE active sites than carbaryl. Our observations are in agreement with results of previous studies in which the same experiments except for the detection method were carried out. FIGS. 11 B-(a) and B-(c) show the dose-dependent inhibition effects of paraoxon and malathion, respectively. FIGS. 11 B-(b) and B-(d) represent the semi log plots of color intensity, corresponding to the same experiments in panels B-(a) and B-(c), respectively. The $IC_{50}$ values and LOD for both paraoxon and malathion were approximately 10 nM and 10 μM, respectively. The data are consistent with the results previously reported.

The insets for FIG. 11 shows the images of the paper strips at each inhibitor concentration, and clearly demonstrate that detection of the inhibitors is possible using the naked eye. This is an advantageous aspect of the bioactive paper strips, as this permits the use of the test strips directly in the field and eliminates the need for sophisticated instrumentation. The presence of a simple colorimetric readout also enables rapid imaging and transmission to a central lab for further quantitative analysis using a simple cell phone camera combined with e-mail or MMS messaging.[3,5,7] Hence, rapid, on-site qualitative or quantitative analysis of organophosphates or carbamates be possible using this reagentless lateral-flow bioactive paper platform.

Figure 12:
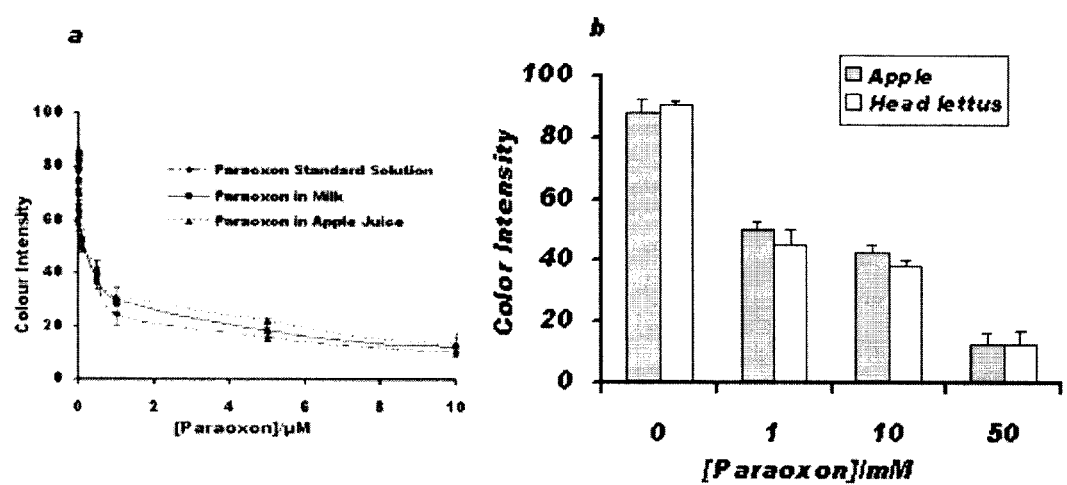
FIG. 12 shows: (a) Matrix effect in the analysis of paraoxon in milk and apple juice samples. Color intensity decreased with the increased standard paraoxon concentration in milk and apple juice; (b) Real life application of paraoxon, where different concentration of paraoxon solution was sprayed on apple and head lettuce, respectively. After air dry, the deposited paraoxon samples were collected and tested using our developed reagentless sensor.

Matrix Effect in the Analysis of Paraoxon in Food Samples:

The matrix effects in the analysis of paraoxon in drinking milk (2%, pH 7.2) and apple juice (pH 3.6) samples were investigated. For this, several standard paraoxon solutions (0~10 μM) were mixed into both milk and apple juice samples. In order to get optimum enzymatic reaction product (indophenoxide⁻) as well as the blue color, pH of the apple juice was adjusted to within the range of 7-8 using a few drops of NaOH (1N). FIG. 12(a) shows that the color intensity decreased almost similarly with the increased paraoxon concentration in both milk and apple juice samples. The detection limit for paraoxon was estimated to be ~10 nm for all the samples. The milk and apple juice samples show very small matrix effects, which would make the recovery determination of pesticide from these fortified samples possible.

It is well known that organic solvents (e.g., 5% methanol or cyclohexane) not only aid in dissolution of the AChE inhibitors, but also enhances the affinity for binding to AChE. However, in order to increase the possible practical application of this paper test, where most certainly 100% aqueous sample solutions would be applied, no organic cosolvent (cyclohexane or methanol) was used in either milk or apple juice samples except 5% organic solvent (e.g., methanol or cyclohexane) was used to make the stock solution of pesticides. The results obtained by using the reagentless paper sensor suggest that the optimized bioactive paper platform is very effective, sensitive and can play a very important role in both quantitative as well as qualitative measurement of pesticides.

Paraoxon Analysis in Real-Life Sample:

In order to investigate pesticide (e.g., paraoxon) effects in real life samples, different concentrations of paraoxon solution (0~50 mM) were sprayed on apple and head lettuce. After air drying, the deposited paraoxon samples were collected using a cotton-swab and tested using the reagentless lateral flow sensor strip. The results of the sensor strip assays are presented as a bar graph in FIG. 12(b), where ~50% inhibition was observed when 1 mM paraoxon was sprayed, while almost complete inhibition was observed when 50 mM paraoxon was sprayed. Beam and Hankinson reported that pesticides remain stable for at least eight days with negligible loss. Usually a highly concentrated pesticide (10M) is sprayed in the fields. Therefore it is dangerous to intake any vegetable or fruits directly from fields where pesticides have been sprayed. Thus the present system could be a good pivotal tool for assessment of low concentrations of class specific OP or CM pesticides, affecting both humans and animals.

Storage Stability of the Sensor Platform:

The long-term stability AChE and its substrate IPA within the layered coating on the paper substrate were investigated. Results demonstrated that the enzyme retained >95% of its initial activity over a period of at least two months when stored at 4° C., indicating that both the enzyme and the IPA reagent remained viable during storage. The observed stability of the enzyme when entrapped in silica is in agreement with previous reports[32] and shows that the reagentless bioactive paper sensor should have a sufficient shelf-life to allow storage and shipping.

Example 3

Development of a Bioactive Lab-on-Paper Sensor for the Detection of E. coli Based on β-glucuronidase Activity Chemicals and Solutions:

β-Glucuronidase (GUS, type VII-A, from *E. coli*, EC 3.2.1.31), indoxyl-β-D-glucuronide cyclohexylammonium salt (IBDG), 5-bromo-4-chloro-3-indolyl β-D-glucuronide sodium salt (X-Gluc), p-nitrophenyl-β-D-glucuronide (PNPG), sodium silicate solution (~14% NaOH, ~27% $SiO_2$), Dowex 50WX8-100 ion-exchange resin, methyltrimethoxysilane (MTMS), polyacrylic acid (PAA, MW~1.25 MDa), 2,3-dichloro-5,6-dicyanobenzoquainone (DDQ), m-chloroperbenzoic acid (MCPBA), 2-iodoxybenzoic acid (IBX), $H_2O_2$, $FeCl_3 \cdot 6H_2O$, Triton X-100, Tween-20, and B-lysing agent were purchased from Sigma-Aldrich. Polyvinylamine (PVAm; 1.5 MDa) was obtained from BASF (Mississauga, Canada), as a gift. B-PER Direct bacterial protein extraction reagent was obtained from Thermo Scientific. $Fe_2O_3$ beads and *E. coli* polyclonal antibody were purchased from BioClone Inc. and Abcam, respectively. Distilled deionized water ($ddH_2O$) was obtained from a Milli-Q Synthesis A10 water purification system. All other reagents were of analytical grade.

Stock solutions of enzyme, GUS and substrates (e.g., X-Gluc, PNPG, IBDG) were made up using phosphate buffer supplemented with 0.5 wt. % BSA (75 mM, pH 8). These solutions can be used up to three months under appropriate storage conditions (−20° C.). Both PVAm (0.5 wt. %) and PAA (0.025 wt. %) solutions were prepared by dissolving in distilled deionized $H_2O$. Methyltrimethoxysilane (MTMS) was hydrolyzed by mixing 98% MTMS with 0.1N HCl in a 5:1 volume ratio. This mixture was sonicated for 20 minutes on ice to promote ether hydrolysis. All other solutions were prepared using phosphate buffer (75 mM, pH 8) if not otherwise stated. CAUTION: All oxidizing agents are toxic. These materials should be handled with gloves and used in fumehood.

Organisms and Plate Counting:

Two non-pathogenic bacteria (*E. coli* BL21 and *B. Subtilis*) strains were used in this study. Standard LB media (total vol. 25 mL with ampicillin 100 µg/mL and chloramphenicol 33 µg/mL) was used for both *E. coli* BL21 and *B. Subtilis* culture. Tryptic soy broth (TSB, total vol. 5 mL) is used for *E. coli* 0157:H7 culture. The cultures were grown overnight at 37° C. with shaking at 125 rpm.

To count the numbers of CFU/mL in bacterial suspensions, cultures are serially diluted with sterile water, and 10 µL of selected dilution was spread evenly over the surface of the warm LB (for *E. coli* BL21 and *B. Subtilis*). TSB agar plates are used for *E. coli* 0157:H7. Plates were incubated at 37° C. for 24 h and count the colonies. Dilutions showing between 30 and 100 colonies were used for calculation of CFU/mL. [CAUTION: *E. coli* BL21 and *B. Subtilis* are non-pathogenic and should be handled following Level 1 biosafety procedures, while *E. coli* 0157:H7 is pathogenic and should be handled in a Level 2 biohazard hood using BSL-2 safety procedures].

Sol-Gel Material Preparation:

A biocompatible sol-gel precursor, sodium silicate (SS) was used to prepare sols for both substrates and oxidizing agents entrapment onto paper. SS sols were prepared by mixing 10 mL of $ddH_2O$ with 2.6 g of sodium silicate solution (pH~13) followed by addition of 5 g of Dowex cation exchange resin to replace $Na^+$ with $H^+$. The mixture was stirred for 30 seconds to reach a final pH of ~4, and then vacuum filtered through a Büchner funnel. The filtrate was then further filtered through a 0.45 µm membrane syringe filter. These sols were used to prepare silica-containing inks as described below.

Figure 13:
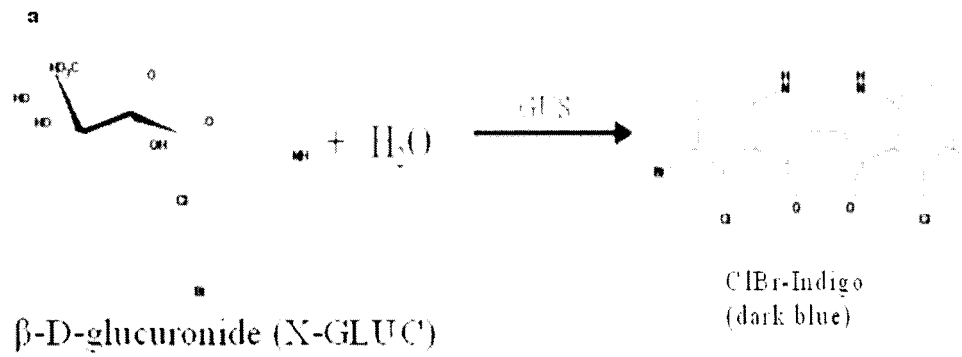
FIG. 13 shows (a) Schematic diagram of the detection principle of the β-D-glucuronide (X-Gluc)-based colorimetric assay. The chromogenic substrate, X-GLUC is hydrolyzed by GUS to form a dark blue indigo dye. (b) Schematic illustration for the development of the bioactive paper-based lateral flow E. coli sensor in which X-Gluc and FeCl₃ were entrapped in the two dashed boxes regions on a Whatman #1 paper strip (1×10 cm) following the sequences of PVAm/ silica/X-Gluc/silica and silica/FeCl₃/silica, respectively by using either the ink jet printing or over spotting. A hydrophobic barrier using either MTMS or wax was introduced over the top of the sensing zone to prevent leaching color and/or increase signal intensity. The sensor is then dipped into pre-lysed contaminated sample (cell lysate).
Figure 13:
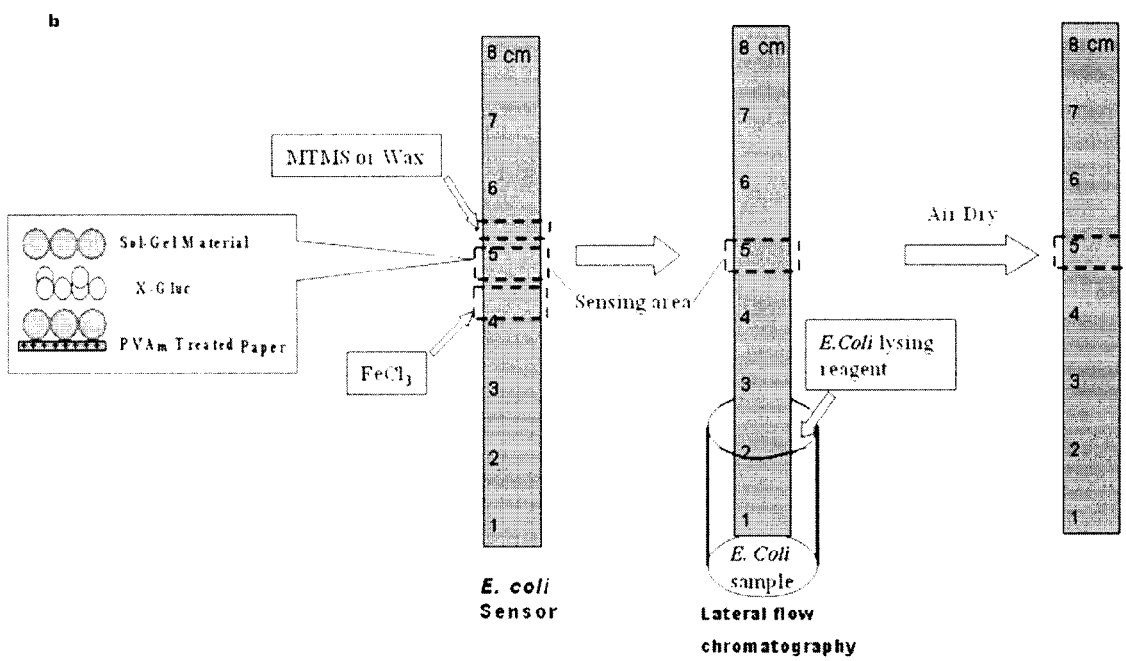

Construction of Bioactive Paper-Based Lateral Flow *E. coli* Test Strips:

A section of Whatman #1 paper was cut into small pieces (1×8 cm) on which substrate, X-GLUC and an oxidizing agent, $FeCl_3$ were entrapped using sol-gel derived silica inks in two different zones (e.g., substrate/sensing and oxidizing agent zones). To prevent leaching of the colored product, a hydrophobic barrier was also introduced on the top of sensing zone using either wax (by a wax printer) or MTMS (by a piezoelectric ink jet printer, DMP-2800, Fujifilm Dimatix, Inc, Japan). The sensing region was prepared by depositing PVAm (0.5 wt %)/silica/X-GLUC/silica layers in the order described, while the oxidizing agent region was prepared by depositing silica/$FeCl_3$/silica layers using either ink jet printing or deposition via micropipette (for proof-of-concept studies and assay optimization), as shown in FIG. 13b. In the case of ink jet printing, all inks were modified with respect to viscosity and surface tension, and printing was done as reported in Examples 1 and 2. After printing, the sensor was allowed to dry for at least 1 h in air at room temperature. For control experiments, a buffer that did not contain X-GLUC was entrapped between the silica layers in the sensing region.

Optimization of Paper-Based Later Flow Test Strips Assay System:

The test strips assay format was optimized with regard to the type and concentration of capture agents, pH, type and concentration of substrate, the kind and concentration of oxidizing agents, and the time for color development.

In order to monitor the capability of capture agents to capture and preserve the color produced from GUS catalyzed reaction when performed on paper, two potential capture agents including PAA (anionic polymer) and PVAm (cationic polymer) were used. In this case, Whatman #1 paper strips (1×10 cm) were treated with both PAA (0 or 0.025 wt. %), and PVAm (0 or 0.5 wt %) using either ink jet deposition or over spotting and were allowed to air dry for 15 min. The capture agents treated strips were then immersed into a solution of blue ClBr-indigo dye (which is produced via reaction of GUS, 5 U/mL and X-Gluc, 4 mM) and allowing the dye to move-up via lateral flow for 10 min. Following the assay the resulting color intensity remaining on the paper strip was monitored once a week for up to 8 weeks.

The effect of pH on enzyme assay was initially investigated in solution. For this, X-Gluc was dissolved with potassium phosphate buffer (75 mM) with 0.5% BSA having different pH values (6-9). 80 µL of X-Gluc (Final concentration of 3 mM) solution and 20 µL of GUS (final concentration of 1 U/mL) were mixed into a 96-well plate. A kinetic study at 610 nm was then performed using a TECAN Safire microwell plate reader for up to 60 min. The effect of pH on enzyme assay with different incubation time on paper was also studied. For this, PVAm/Silica/X-Gluc/Silica layers were printed or over spotted at a width of 0.5 cm across the Whatman #1 filter paper 5 cm from the bottom of the paper (X-Gluc concentration of 3 mM), while silica/$FeCl_3$/silica layers were printed or over spotted in a 0.5 cm wide area across the paper strip 4 cm from the bottom of the paper ($FeCl_3$ concentration of 2 mM) (same as FIG. 13b). The sensor was then immersed into GUS solution (final concentration of 1 U/mL) having different pH values (6-8.5) and was removed as soon as the solution has reached to the sensing region via lateral flow. GUS hydrolyzes the chromogenic substrate X-Gluc to produce a transition from a colorless substrate to deep blue colored product. The color intensity was then monitored with different incubation time (5, 30, and 60 min).

The chromogenic substrates (e.g., X-Gluc, PNPG, and IBDG) were tested initially in silica monoliths present in 96 well plates and later on paper. For this, all of these substrates were dissolved separately with sodium phosphate buffer (75 mM, pH 8). Different concentrations (final concentration of 0-10 mM) of each of them were entrapped in SS+30% glycerol in a 96 well plate (total volume of 80 µL). 20 µL of GUS (final concentration of 1 U/mL) was then added into each well and incubated for 30 min to allow color development. The absorbance at 610, 400, and 380 nm was then measured using a TECAN M1000 plate reader. A digital camera was also used to take a photograph of the plate. Within these three substrates, only the concentration of X-Gluc was further optimized on paper assay due to formation of relatively high visual color intensity produced via enzymatic hydrolysis of X-Gluc. For this, different concentration of X-Gluc (0-10 mM), and $FeCl_3$ (2 mM) were entrapped on paper as described previous section (FIG. 13b). The sensor was then immersed into GUS solution (1 U/mL) and removed as soon as the Gus solution has reached the sensing region through $FeCl_3$ zone followed by a certain incubation time (5, 30, and 60 min) at room temperature. Note that the speed of reaction between GUS and X-Gluc is somewhat slow (about 1 hr), while the reaction in the presence of the oxidizing agent, $FeCl_3$ is far more rapid, leading to color formation in 5 min.

Five different oxidizing agents including, 2,3-dichloro-5,6-dicyanobenzoquainone (DDQ), m-chloroperbenzoic acid (MCPBA), 2-iodoxybenzoic acid (IBX), $H_2O_2$, $FeCl_3$ were used to determine the most effective oxidizing agent to speed up the enzyme (GUS)-substrate (X-Gluc) reaction. Experiments were conducted firstly in 96-well plate, in which GUS (final concentration of 1 U/mL) was entrapped in silica gel. The substrate, X-Gluc (4 mM) and oxidizing agents (1 mM each) were then added to each well (designated for the individual oxidizing agent), and incubated for 30 min. The concentration gradient (0-30 mM) of $FeCl_3$ was also observed in 96-well plate. The absorbance at 610 was measured using a TECAN M1000 plate reader for each experiment. A digital camera was also used to take a photograph of the plate. The effect of $FeCl_3$ activity was then optimized on the bioactive paper strip by measuring the color intensity produced by the enzymatic hydrolysis of X-Gluc. Various concentrations of $FeCl_3$ (0-10 mM), and X-Gluc (3 mM) were entrapped on paper using biocompatible silica material in order to make the sensor strips, as described in the previous section. The performance of the sensor was then assayed by dipping it into the GUS solution (1 U/mL) to allow the enzyme solution to reach the sensing zone through $FeCl_3$ zone via lateral flow. The color development times tested were 5, 30, and 60 min.

The detection as well as the color intensity of the sensing areas was monitored by naked eye, by obtaining a digital image (Canon A630, 8.0 MegaPixel camera operated in automatic mode with no flash and with the macroimaging setting on) or office scanner, and using ImageJ™ software to analyze the jpeg images as described in Examples 1 and 2.

Performance of *E. coli* Test Strips:

Different concentrations of bacteria cells (e.g., *E. coli* BL21 or *B. Subtilis*) suspensions ranging from 0-1×10$^7$ CFU/mL were made for this study. Three different set of experiments were conducted for each of the bacterial strains. 2 mL of bacterial cell suspension was mixed with 200 µL of B-PER DIRECT bacteria lysing reagent by pipetting up and down and incubated for 15 min at room temperature. The bacteria sample or lysate was then assayed using the paper sensor via lateral flow technique as outlined above. When the lysate reached to the sensing zone of the sensor, lateral flow was stopped and the sensor was allowed to dry in air. A colorless-to-deep blue color change could be observed within a few min due to enzymatic hydrolysis of substrate, X-Gluc. The level of *E. coli* in samples was detected by measuring the color intensity with incubation time at 5, 30, or 60 min. The color intensity was determined by analyzing a digital image with the ImageJ™ software as described above.

Preparation of Antibody-Conjugated Magnetic Beads (MBs) for *E. coli* Capture:

Conjugation of antibody (goat pAb to *E. coli*, Abcam) to MBs (hydrazide modified, 1 µm, 1.7×10$^8$ beads/mg, Bioclone Inc.) was conducted according to the instructions provided by the manufacturer. Briefly, the conjugation protocol could be performed in two steps: 1) Oxidation of Antibody. A measured amount of pAb was added to 1 mL of sodium acetate buffer (0.1 M, pH 5.6). A mild oxidizing agent, sodium metaperiodate ($NaIO_4$, final concentration of 10 mM) was added into pAb solution and incubated the sample in the dark room at room temperature for at least 30 min with gentle rotation. The unreacted $NaIO_4$ was then removed using a Nanosep Centrifugal Device (consists of a sample reservoir with encapsulated membrane with pore size, 30K and a filtrate receiver) followed by centrifugation at 14 000 g for 5 min, and the oxidized pAb was then dissolved with 500 µL sodium acetate buffer (0.1 M, pH 5.6). 2) Coupling of Antibody to Magbeads. A solution of completely suspended MBs (100 uL, 4-8×10$^8$ beads/mL) was transferred to a microcentrifuge tube and placed into a magnetic separator for 2-3 min. The supernatant was discarded and the bead pellet was redispersed in 500 μL of sodium acetate buffer (0.1 M, pH 5.6) after washing with the same buffer 3 times. This MBs solution was then mixed with 500 μL of oxidized antibody (from step 1). The mixture was then allowed to keep shaking for at least 6 h at room temperature. The loading of pAb onto MBs was determined by measuring fluorescence intensities of the supernatant (intrinsic tryptophan fluorescence measurements at Ex 284 nm and Em 342 nm using TECAN Infinite M1000) every 2 h followed by magnetic separation. Various amounts of pAbs were added to 500 μL of washed Magbeads (same as above) to optimize the Ab loading on MBs. The equation (1) was used for a rough quantitative measurement of how much pAb was bound to the beads.

$$\%Ab\ bound = [1-(Fl_a/Fl_b)]*100 \qquad (1)$$

where,
$Fl_b$=Fluorescence intensity of Ab solution before its binding to beads, and
$Fl_a$=Fluorescence intensity of Ab solution (supernatant) after its binding to beads After successful binding, antibody conjugated MBs were washed with sodium acetate buffer (0.1 M, pH 5.6) 3 times and then with PBS buffer (pH 7.4) 5 times followed by a magnetic separation. The antibody conjugated MBs were resuspended with 1 mL PBS (10 mM, pH 7.4), which could be stored at 4° C. for more than 1 month.

Preconcentration of *E. coli* Using MB-Ab:

MB-Ab (200 μL, 1.4-2.4×10$^8$ beads) was dispersed in 10 mL of *E. coli* containing PBS solution (10$^2$-10$^6$ CFU/mL). The mixture was incubated at room temperature under shaking (220 rpm) for 1 h. After incubation, the MB-Ab-*E. coli* complex was collected using a magnetic separator and the supernatant was transferred into a new tube for quantification of captured *E. coli* by the plate counting method. A capture efficiency of MB-Ab system was estimated by counting colonies after addition of MB-Ab in sample tubes containing various numbers of *E. coli*. The amount of MB-Ab was also optimized by varying the volume of MB-Ab (20-500 μL) with constant cell number (10$^4$ CFU/mL). MB-Ab-*E. coli* complex was washed 5 times in 10 mM PBS (pH 7.4) and then resuspended in 1.8 mL of phosphate buffer (pH 8). 200 μL of B-PER DIRECT bacteria lysing reagent was mixed and incubated for 15 min at room temperature. Finally, the sensor strips was immersed into the cell lysate solution and the level of *E. coli* in samples was detected by measuring the color intensity through image analysis as described above.

Detection of *E. coli* in Food, Beverage, and Environmental Samples:

Apple juice, milk (1%), and water samples were used for this study. All samples (10 mL each) were contaminated artificially with a known number of *E. coli* cells (10$^4$ CFU/mL). Prior to analysis, the pH of the apple juice was adjusted to between 7 and 8 by adding a few drops of 1 N NaOH. Milk and water samples were tested with no additional processing. Cells were pre-concentrated using MB-Ab as described above and resuspending them with 2 mL fresh juice, milk or water instead of phosphate buffer (pH 8) in order to make the sensor more applicable for testing the real life samples. The samples were then tested using the sensor strips as outlined above. The color intensity was determined by analyzing a digital image with the ImageJ software. Uninoculated apple juice, milk, and water were used as controls and also analyzed to determine the presence of *E. coli* using the sensor strips.

Interference and Specificity Test:

Though bacteria with no GUS activities do not interfere with the signal, interference by non-target bacteria with high GUS activities cannot be neglected. To demonstrate the interference study (only with GUS negative bacterial strain), *E. coli* BL21 and *B. Subtilis* were grown individually. 2 mL of *E. coli* suspension (10$^6$ CFU/mL), 2 mL of *B. Subtilis* (10$^6$ CFU/mL), and a mixture of both bacterial suspensions (1 mL each, 10$^6$ CFU/mL each) were lysed using B-PER DIRECT bacteria lysing agent separately. The sensor was used to test the GUS activities followed by lysis the cells as outlined in the previous section and the color intensities produced (from individual and mixture cells lysate) were compared.

To test the specificity of non-pathogenic bacteria, goat pAb (specific to *E. coli*) was used in the immunomagnetic separation of *E. coli* (in the same manner as described above) from a mixture of *E. coli* and *B. Subtilis*. In the case of pathogenic bacteria, anti-*E. coli* O157:H7 antibody-coated MBs (purchased from Invitrogen) is used for separation of *E. coli* O157:H7 specifically from a mixture of cells. To determine the detection limit, triplicate analysis of controls/blanks were performed for all the experiments.

Storage Stability of the Test Strips:

The long-term stability of the test strips (at room temperature) was examined every week up to 8 weeks by immersing the test strip into *E. coli* (10$^5$ CFU/mL) lysate solution. The assay conditions were the same as those described above.

Results and Discussion

Optimization of Paper-Based Later Flow Test Strips Assay Format:

Assay time, sensitivity, selectivity and reproducibility are factors to consider for rapid detection of *E. coli* in food, medical, environmental or other samples. Therefore, in order to develop an efficient paper-based *E. coli* sensor, parameters such as capture agents (type and concentration), substrate (type and concentration), pH of the buffer, oxidizing agents (kind and concentration), and the time for color development were optimized.

It was assumed that the dark blue color product, ClBr-indigo dye (which is produced via GUS catalyzed hydrolysis of X-Gluc) is a neutral material. Therefore, in order to monitor the capability of capture agents to capture and preserve the color product on paper, two potential capture agents including anionic (Polyacrylic acid, PAA) and cationic (Polyvinylamine, PVAm) polymers were used in a lateral flow-based paper chromatographic system. The results indicated that a 0.5 wt % PVAm level was able to trap and concentrate the indigo dye efficiently, while the PAA treated and unmodified paper (control) failed to trap the blue color product indicating that the ClBr-indigo dye is anionic. This level of PVAm also preserved the blue color product after storage for more than two months. Thus this level of PVAm was used in all further paper-based assays in this Example.

To develop an efficient *E. coli* test trip assay platform, it is desirable that a GUS chromogenic substrate suitable for visual detection is used. Initially the substrate was selected from three different chromogenic substrates, such as indoxyle-β-D-glucuronide (IBDG), para-nitro-β-D-glucuronide (PNPG) and 5-bromo-4-chloro-3-indolyl β-D-glucuronide (X-Gluc) based on their capability for visual color formation via GUS catalyzed hydrolysis of these substrates in solution for 30 min. Results showed that IBDG and PNPG produced a relatively faint color (blue and yellow, respectively), while X-Gluc produced a distinct deep blue color. Therefore, the X-Gluc was selected as the most suitable substrate and the concentration of X-Gluc was further optimized on paper for the development of the colorimetric paper-based *E. coli* assay platform. For this, an ideal lateral-flow paper based *E. coli* sensor was constructed following the procedure as described above. The effects of [X-Gluc] on signal levels with different drying time at room temperature are shown in FIG. 14*a* (a separate paper sensor is used for each X-Gluc concentration). Here it is seen that with increasing concentration of X-Gluc, the color intensity increased with saturation at [X-Gluc]~4 mM. Based on this, 4 mM X-Gluc was chosen as the optimal substrate concentration. Using the paper-based assay, the $K_M$ for X-Gluc was found to be ~0.7 mM, which is in good agreement previous literature reports. For the prescribed times tested for color development, increasing time caused an increase of the color intensity. The most suitable time for color development was around 1 h though color can be detected at an earlier time.

It is well known that the rates of oxidation of indoxyls (intermediate product produced due to GUS catalyzed hydrolysis of X-Gluc) to indigo dyes are relatively slow at room temperature.[41] The rate of indoxyl oxidation is also known to be pH and oxidizing agent-dependent and therefore, optimization of pH and oxidizing agent are the other parameters for increasing the sensor performance as well as reducing the assay time. Therefore the absorbance of the GUS catalyzed hydrolysis of X-Gluc was determined as a function of time and pH in solution. It was found that the absorbance (due to rate of oxidation of indoxyle) increased with increasing pH (over the range ph 6.0 to 8.0) and time. A slight variation from pH 8.0 gives considerably lower absorbance readings. The most suitable time for color development was around 1 h. The data also suggested that pH values above pH 8.5 were not compatible with maintenance of GUS activity, while maximum signal was obtained at pH 8 with 1 h incubation time when measuring absorbance at 610 nm. The effect of variation of pH and time for color development were further optimized in paper-based assays. For this, substrate, X-Gluc and an oxidizing agent, $FeCl_3$ were entrapped at two different zones (e.g., lower $FeCl_3$ region and upper X-Gluc region) of the paper-based sensor strip (FIG. 13*b*). The sensor was then immersed into GUS solution (final concentration of 1 U/mL) having different pH values (6-8.5) and was removed as soon as the solution had reached to the sensing region via lateral flow. The produced blue color intensity was then measured with different drying time (5, 30, and 60 min). FIG. 14*b* shows that the color intensity increases with pH over the range pH 6.0 to 8.0 and above pH 8.5, color intensity is decreased owing to possibility of degradation of enzyme at this higher pH level. The data also demonstrated that color intensity increases with time and 5 min was the minimum length of time to allow measurement of color. The maximum signal was obtained at pH 8 (similar to that of solution assay) with 1 h drying time therefore, pH 8 and 1 h drying time was used for all further paper-based assays.

A 96-well format was used to select the appropriate oxidizing agent for oxidation of indoxyl to blue color product, ClBr-indigo dye rapidly. A comparison of the blue color development (visual detection) in silica monoliths was performed for 30 min using five different oxidizing agents (e.g., $FeCl_3$, DDQ, MCPBA, IBX, and $H_2O_2$). Among these oxidizing agents tested, $FeCl_3$ was selected as the most suitable one based on the strongest visual color intensity produced. The poorest performance for blue color development was observed in the presence of DDQ. The effect of adding varying levels of $FeCl_3$ over the bioactive paper strip are shown in FIG. 14*c* (a separate paper sensor is used for each $FeCl_3$ concentration). Prior to this, the paper-based *E. coli* sensor was made following the protocol mentioned above. Here it is seen that as the concentration of $FeCl_3$ increases so too does the color intensity, recorded 5, 30 and 60 min after reaching the GUS solution (1 U/mL) over the substrate area via lateral flow chromatographic technique. The color intensity saturated at a level of ~1 mM $FeCl_3$. The color intensity was about four-fold higher (after 5 min drying time) than that of a negative control (absence of $FeCl_3$).

Also assessed was whether or not the supporting silica material, paper substrate or PVAm layers degraded X-Gluc, therefore similar experiments were conducted to those described above with no GUS present in the solution. The signals remained at the baseline level upon addition of varying levels of X-Gluc and were similar to signals obtained from control experiments performed in the absence of substrate. Thus, the present results confirm that the change in the color intensity is due to the enzyme catalyzed hydrolysis of X-Gluc to ClBr-Indigo dye (blue color product). Furthermore, this result shows that both the X-Gluc and $FeCl_3$ remain stable when deposited between silica layers on a paper substrate.

Analytical Performance of *E. coli* Test Strips:

To evaluate the analytical performance of the developed paper-based *E. coli* test strips, different known concentrations of bacteria cell (over the range $0-9\times10^6$ CFU/mL) suspensions were lyzed using B-PER direct bacteria lysing reagent in order to release the intracellular GUS enzyme into solution. The cell lysate was then tested by dipping the test strip directly into it. Colorless-to-deep blue color changes could be observed within a few minutes due to GUS catalyzed hydrolysis of substrate, X-Gluc. The developed blue color intensity corresponds to the level of *E. coli* in samples. In parts a and b of FIG. 15 represent the semi-log plot of blue color intensity (due to different *E. coli* concentrations) obtained using an office scanner and a digital camera, respectively, and through digital image analysis of the same data. An increase in blue color intensity was observed with increasing concentration of *E. coli* BL21. However, color intensity was relatively low in FIG. 15*b* compared to FIG. 15*a*. The reason for this is that environmental illumination interferes with the signal when the pictures were taken using a camera. The visual results indicated that the sensor is able to detect *E. coli* at a level of ca. $1\times10^6$ and ca. $9\times10^3$ CFU/mL within 5 min and after a 1 h drying time, respectively. This is because the produced enzyme concentration is limited from the lower number of cells. The limit of detection was defined as the cell concentration producing a signal equal to or higher than the average signal produced by the blank plus three standard deviations was $9\times10^3$ CFU/mL. The cell sensing system proved to be precise, with in-assay coefficients of variation less than 5%.

Prior to performing the cell lysis experiment, an appropriate bacteria lysis reagent was selected from 4 different lysis reagents such as Tween™ 20, Triton X100, CellLytic™ B.cell lysis reagent, and B-PER direct protein extraction reagent. For this, *E. coli* BL21 cell suspension ($1\times10^6$ cfu/mL in 75 mM phosphate buffer, pH 8) was mixed separately with all of these lysis reagents for 15 min at room temperature. X-Gluc (final concentration, 4 mM) and $FeCl_3$ (1 mM) were then added and incubated 60 min for color development. The visual results indicated that B-PER direct protein extraction reagent is more efficient to lyse the cell and had less inhibitory effects on GUS enzyme in comparison to that of other lysis reagents. Therefore, B-PER lysis reagent was used for all subsequent paper-based assays.

It was also shown that patterned paper can concentrate the color to a narrow zone/band, which in turn increases the sensor sensitivity. For this, two different patterns (e.g., open or closed microfluidic channel type) were created using Microsoft PowerPoint™ with black lines at 2 pt thickness. The patterns were printed on Whatman 1 paper using wax ink and then placed in an oven at 100° C. for 5 min to melt the wax and impregnate the fibers. The paper was then treated with 0.5 wt % PVAm and entrapped X-GLUC and $FeCl_3$ in the indicated regions using sol-gel derived silica matrix. Both patterns were dipped in GUS solution (1 U/mL) to test their utility. Results showed that the microfludic closed channel based patterned paper provided a total intensity that was 1.7-fold higher than the others. Therefore, this patterned paper sensor was used for the *E. coli* assay, which is shown in FIG. 15c, where color intensity increases with *E. coli* concentration (separate paper sensor was used for each concentration). The results demonstrated that the paper strip biosensor was able to detect low *E. coli* concentration (LOD) down to $4.2 \times 10^3$ CFU/mL upon color development for 60 min indicating that the pattern paper sensor is more sensitive and has a better LOD (>2 fold) for *E. coli* ($4.2 \times 10^3$ CFU/mL) than for the non-patterned paper sensor (LOD=$8.9 \times 10^3$ CFU/mL), likely due to the ability to concentrate the color into a narrow area. Overall, the data clearly show that the detection of the *E. coli* is possible with the naked eye, thereby avoiding the need for expensive and sophisticated instruments or electric power. Such a platform also makes it possible to perform remote sensing as qualitative estimations can be made on-site or images can be sent via camera phone to a central laboratory for quantitative assessment though image analysis.

Interferences on Assay Performance:

In order to demonstrate the interferences on signal by other non-producing GUS cells, initially *E. coli* BL21 and *B. Subtilis* ($4.1 \times 10^6$ CFU/mL each) were mixed, lyzed, and tested in solution. In the case of *B. subtilis* alone, no color was observed, while for the mixed-culture, deep blue color was observed (FIG. 16a). After the solution assay, the paper sensor was then used to test the GUS activities for different concentrations of mixed cell lysates following the protocol as outlined in the previous section. FIG. 16b shows that there was a negligible effect on the general shape of the response vs. concentration or the limit of detection, with the detection limit for *E. coli* being $4.1 \times 10^3$ CFU/mL after a 1 hr drying time. While it is true that other GUS producing cells would be expected to interfere, it is likely that more than 95% of *E. coli* strains are able to produce GUS and *E. coli* is a common indicator of fecal contamination and pollution (e.g., coliforms and fecal coliform etc). At the very least, the sensor is able to detect any GUS producing cells but does not provide identification of the specific cell strain that is detected.

*E. coli* Assay in Beverage Samples:

Milk (1%) and orange juice were artificially contaminated with *E. coli* (ca. $4 \times 10^5$ CFU/mL) to assess the effect of such sample matrices on assay performance and detection limits. Prior to the assay, the pH of the samples was adjusted to the range of 7-8, which retained the activity of the GUS enzyme in the samples. As shown in FIG. 17, the signal variation (for both milk and orange juice samples) is almost similar to that typically obtained (see FIG. 15c), which indicates that the food samples matrices had a negligible effect on the limit of detection. The above findings clearly show that the proposed assay platform can be used for rapid and convenient visual monitoring of beverage and environmental samples, thus providing to be a valuable portable tool for on-site analysis.

Storage Stability of the Sensor:

The long-term stability of the sensor strips was also investigated. The results demonstrated that the strips could be stored for more than two months at room temperature without noticeable decrease in the sensing GUS activity. It is important to note that no biomolecules are required for constructing the novel *E. coli* sensor of the present application.

Example 4

Test Kit Based on Magnetic Preconcentration and Bioactive Paper Strips

A test kit that combines magnetic preconcentration and bioactive paper strips should allow selective detection of pathogenic bacteria in food and water with no need for culturing or instrumentation, making it suitable for remote and resource limited locations that may lack electricity. The test strip is printed with a chromogenic substrate region and a capture/preconcentration region to allow ultrasensitive detection of bacteria based on the ability of specific bacterial enzymes to convert the colorless substrate to a highly colored product (like that described in Example 3).

An advantage of the above approach is the ability to provide a cost-effective, portable, easy-to-use test strip that can either be observed directly by eye or recorded by a digital camera. The combination of magnetic preconcentration and amplified detection of bacteria should allow detection of as little as 10-20 CFU/mL of pathogenic bacteria with no need for culturing, and can be produced as a simple kit, permitting the test to be run even by untrained personnel. Thus, this example will provide a new test strip platform technology that directly addresses the need for low-cost diagnostics that can protect against infectious disease.

The assay kit is designed to perform three intricately linked chemical and biochemical processes: 1) specific preconcentration of one or multiple pathogenic organisms using magnetic preconcentration, 2) lysing of cells to release intracellular β-glucuronidase (β-gus) or 3-galactosidase (β-gal) enzymes, and 3) a paper-based multi-pathogen detection assay utilizing a chromogenic substrate for β-gus or β-gal, along with a strong oxidizing agent to accelerate product formation and a capture zone to concentrate the product into a narrow band for highly sensitive detection. Together, this combination of processes has the potential to provide rapid (<5 min) and ultralow detection limits (~10 CFU/mL) for a variety of pathogenic bacteria.

More specifically, the assay utilizes antibody-derivatized magnetic beads to selectively concentrate one or more pathogenic bacteria from an initial volume of ~50 mL to a final volume of ~0.5 mL, which results in a 50-100 fold concentration enhancement depending on capture efficiency of the cells by the magnetic particles. To the 0.5 mL of sample is added 0.5 mL of a lysing buffer, which releases either β-gus (endogenous to *E. coli* BL21 and K12, as well as *salmonella*) or β-gal (endogenous to *E. coli* H7:O157) in an active form. A paper strip is then introduced to the solution to allow lateral flow of the sample up the paper. The paper contains several lanes which contain either: 1) a suitable chromogenic substrate for β-gus; 2) a chromogenic substrate for β-gal; 3) a chromogenic substrate for a common bacterial enzyme as a positive control; or 4) no substrate (negative control). In addition, each lane contains a strong oxidizing agent, which accelerates the rate of product formation, and a capture zone (cationic polymer coated region) that concentrates the anionic product within a narrow zone. All reagent zones are printed by an ink-jet method using a special sol-gel derived ink. After a suitable reaction time (ca. 5 min), the developed color is used to quantify the amount of a selected pathogen initially present in the test sample.

The results in Example 3 have demonstrated the ability to 1) form multi-channel fluidic devices on paper using wax printing; 2) print all reagent zones onto the paper strips using an ink-jet method and a sol-gel based ink, 3) detect β-gus enzymes liberated from lysed *E. coli* K12 cells using the paper strip. Using this format, E. coli has been successfully detected with a detection limit of 10³ CFU/mL. Preliminary data has also been obtained on the use of magnetic preconcentration, with preconcentration levels being ~50-fold for E. coli K12, and detection limits being on the order of 20 CFU/mL (starting with a sample volume of 50 mL).

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

[9] No, H.-Y.; Kim, Y. A.; Lee, Y. T.; Lee, H.-S. *Anal. Chim. Acta* 2007, 594, 37-43
[10] Jordan, J. D.; Dunbar, R. A.; Bright, F. V. *Anal. Chem. Acta* 1996, 332, 83-91
[11] Katagiri, K.; Hasegawa, K.; Matsuda, A.; Tatsumisago, M.; Minami, T. *J. Am. Ceram. Soc.* 1998, 81(9), 2501-2503.
[12] Van der Biest, O. O.; Vandeperre, L. T. *Annu. Rev. Mater. Sci.* 1999, 29, 327-352.
[13] Goring, G. L. G.; Brennan, J. D. *J. Mater. Chem.* 2002, 12, 3400-3406.
[14] Harrell, T. M.; Hosticka, B.; Power, M. E.; Cemke, L.; Hull, R.; Norris, P. M. *J. Sol-gel Sci. Technol.* 2004, 31, 349-352.
[15] Sabina Di Risio and Ning Yan. *Macromol. Rapid Comm.* 2007, 28 (18-19), 1934-1940.
[16] Wang, J.; Pamidi, P. V. A.; Park, D. S. *Anal. Chem.* 1996, 68, 2705-2708.
[17] Xu, T.; Jin, J.; Gregory, C.; Hickman, J. J. *Biomaterials* 2005, 26, 93-99.
[18] Ilkhanizadeh, S.; Teixeira, A. I.; Hermanson, O. *Biomaterials* 2007, 28, 3936-3943.
[19] Bietsch, A.; Hegner, M.; Lang, H. P.; Gerber, C. *Langmuir* 2004, 20, 5119-5122.

TABLE 1

| Bioink Formulation (with 0.1 wt. % Triton X-100) | AChE Activity | Viscosity (cp) | Surface Tension (mN/m) | Jetting Conditions | Bioink Jettability | Movies of Drop Formation |
|---|---|---|---|---|---|---|
| Bioinks for AChE | | | ↑ | ↑ | | ↑ |
| Tris buffer (100 mM, pH 8) | + | 1.01 ± 0.02 | | | None | |
| 1% (v/v) Glycerol + Tris buffer | + | 1.06 ± 0.03 | | | None | |
| 10% (v/v) Glycerol + Tris buffer | + | 1.35 ± 0.08 | | | Sporadic | |
| 20% (v/v) Glycerol + Tris buffer | + | 1.91 ± 0.11 | | Firing voltage: 40 v | Good | |
| 30% (v/v) Glycerol + Tris buffer | + | 2.80 ± 0.13 | | Wave form: | Excellent | |
| 40% (v/v) Glycerol + Tris buffer | + | 4.21 ± 0.09 | | Single pulse. | Excellent | |
| 50% (v/v) Glycerol + Tris buffer | + | 6.85 ± 0.21 | | Fall in | Excellent | See |
| Bioinks for SS sol-gel material | | | 30~38 | two steps | | supplementary |
| Sodium silicate (SS) | + | 1.33 ± 0.04 | | Pulse width: | None | movies |
| 1% (v/v) Glycerol + SS | + | 1.44 ± 0.07 | | 70 μs | Poor | |
| 10% (v/v) Glycerol + SS | + | 1.67 ± 0.10 | | Meniscus vacuum: | Sporadic | |
| 20% (v/v) Glycerol + SS | + | 2.00 ± 0.13 | | 4.0-4.5 inches H₂O | Good | |
| 30% (v/v) Glycerol + SS | + | 2.67 ± 0.16 | | Firing frequency: | Excellent | |
| 40% (v/v) Glycerol + SS | + | 3.67 ± 0.19 | | 5 kHz | Excellent | |
| 50% (v/v) Glycerol + SS | + | 6.00 ± 0.23 | | | Excellent | |
| Bioink for PVAm | | | | | | |
| PVAm (0.5 wt. %) | ** | 3.08 ± 0.14 | ↓ | ↓ | Excellent | ↓ |

Note:
+, the AChE retains activity (>95%);
**, not applicable

FULL CITATIONS FOR DOCUMENTS REFERRED TO IN THE SPECIFICATION

[1] Li, X.; Tian, J.; Nguyen, T.; Shen, W. *Anal. Chem.* 2008, 80 (23), 9131-9134.
[2] Abe, K.; Suzuki, K.; Citterio, D. *Anal. Chem.* 2008, 80 (18), 6928-6934.
[3] Martinez, A. W.; Phillips, S. T.; Butte, M. J.; Whitesides, G. M. *Angew. Chem., Int. Ed.* 2007, 46, 1318-1320.
[4] Zhao, W.; Ali, M. M.; Aguirre, S. D.; Brook, M. A.; Li, Y. *Anal. Chem.* 2008, 80(22), 8431-8437.
[5] Bruzewicz, D. A.; Reches, M.; Whitesides, G. M. *Anal. Chem.* 2008, 80(9), 3387-3392.
[6] Su, S.; Ali, M. M.; Filipe, C. D. M.; Li, Y.; Pelton, R. *Biomacromolecules* 2008, 9(3), 935-941.
[7] Martinez, A. W.; Phillips, S. T.; Whitesides, G. M. *Proc. Natl. Acad. Sci. USA* 2008, 105(50), 19606-19611.
[8] Liu, J.; Mazumdar, D.; Lu, Y. *Angew. Chem. Int. Ed.* 2006, 45, 7955-7959.
[20] Marrs, T. C. *Pharmacol. Ther.* 1993, 58(1), 51-66.
[21] Rosenfeld C. A.; Sultatos, L. G. *Toxicol. Sci.* 2006, 90(2), 460-469.
[22] Ellman, G. L.; Courtney, K. D.; Andres, V.; Featherstone, R. M. *Biochem. Pharmacol.* 1961, 7, 88-95.
[23] Besanger, T. R.; Hodgson, R. J.; Green, J. R. A.; Brennan. J. D. *Anal. Chim. Acta* 2006, 564, 106-115.
[24] (a) Gluconamides: (i) DePasquale, R. J.; Wilson, M. E. U.S. Pat. No. 4,591,652 (to SCM Corp., USA), 1986. (ii) Haupt, M.; Knaus, S.; Rohr, T.; Gruber, H. Carbohydrate modified polydimethylsiloxanes part 1. Synthesis and characterization of carbohydrate silane and siloxane building blocks *J. Macromol. Sci., Part A: Pure Appl. Chem.* 2000, A37, 323-341. (b) A related compound, the maltopentaose-modified silane: Enomoto, N.; Furukawa, S.; Ogasawara, Y.; Akano, H.; Kawamura, Y.; Yashima, E.; Okamoto, Y. Preparation of Silica Gel-Bonded Amylose through Enzyme-Catalyzed Polymerization and Chiral Recognition Ability of Its Phenylcarbamate Derivative in HPLC. *Anal. Chem.* 1996, 68, 2798-2804.

[25] Martinez, A. W.; Phillips, S. T.; Butte, M. J.; Whitesides, G. M. *Agnew. Chem. Int. Ed.* 2007, 46, 1318-1320.

[26] Brook, M. A.; Chen, Y.; Guo, K.; Zhang, Z.; Brennan, J. D. *J. Mat. Chem.* 2004, 14, 1469-1479.

[27] Zhang, C.; Malhotra, S. V. *Talanta* 2005, 67, 560-563.

[28] Arduini, F.; Errico, I.; Amine, A.; Micheli, L.; Palleschi, G.; Moscone, D. *Anal. chem.* 2007, 79, 3409-3415.

[29] Goring, G. L. G.; Brennan, J. D. *Chem. Mat.* 2007, 19, 5336-5346.

[30] Hodgson, R.; Chen, Y.; Zhang, Z.; Tleugabulova, D.; Long, H.; Zhao, X.; Organ, M. G.; Brook, M. A.; Brennan, J. D. *Anal. Chem.* 2004, 76, 2780-2790.

[31] Besanger, T. R.; Brennan, J. D. *J. Sol-gel Sci. Technol.* 2006, 40, 209-225.

[32] Pandey, P. C.; Upadhyay, S.; Pathak, H. C.; Panday, C. M. D.; Tiwari, I. *Sens. Act. B* 2000, 62, 109-116.

[33] Pavlov, V.; Xiao, Y.; Willner, I. *Nano Lett.* 2005, 5(4), 649-653.

[34] Koruso, K; Pelton, R. *J. Pulp Paper Sci.* 2004, 30, 228-232.

[35] Sharma, J.; Tleugabulova, D.; Czardybon, W.; Brennan, J. D. *J. Am. Chem. Soc.* 2006, 128, 5496-5505.

[36] Marrs, T. C. *Pharmacol. Ther.* 1993, 58(1), 51-66.

[37] Rosenfeld C. A.; Sultatos, L. G. *Toxicol. Sci.* 2006, 90(2), 460-469.

[38] Arduini, F.; Errico, I.; Amine, A.; Micheli, L.; Palleschi, G.; Moscone, D. *Anal. chem.* 2007, 79, 3409-3415.

[39] Lin, T.-J.; Huang, K.-T.; Liu, C.-Y. *Biosens. Bioelectron.* 2006, 22, 513-518.

[40] Pandey, P. C.; Upadhyay, S.; Pathak, H. C.; Panday, C. M. D.; Tiwari, I. *Sens. Act. B* 2000, 62, 109-116.

[41] Cotson, S.; Holt, S. T. *Proceedings of the royal Society of London. Series B, Biological sciences*, 1958, 148 (933), 506-519.

What is claimed is:

1. A biosensor for the detection of an intrinsic or recombinant β-glucuronidase or β-galactosidase enzyme comprising:
   (a) a substrate having a first and second end;
   (b) a reaction zone immobilized on the substrate comprising layers that are printed on the substrate using inkjet printing and are arranged in order beginning adjacent to the substrate of: (i) a first biomolecule compatible sol gel layer; (ii) a chromogenic substrate for the enzyme; and (iii) a second biomolecule compatible sol gel layer;
wherein immersion of the first end of the substrate in a solution comprising or suspected of comprising the enzymes, results in lateral flow of the solution from the first end of the substrate to the second end of the substrate by capillary action, the flow passes through the reaction zone where the enzymes, if present, react with the chromogenic substrate, the chromogenic substrate is one that, when reacted with the enzyme produces a colored product that is detected, and detection of the coloured product indicates that the solution comprised the enzymes; or
wherein overspotting a solution comprising or suspected of comprising the enzymes on to the reaction zone results in the enzymes, if present, reacting with the chromogenic substrate, the chromogenic substrate is one that, when reacted with the enzyme produces a colored product that is detected, and detection of the coloured product indicates that the solution comprised the enzymes; or
wherein dipping the biosensor into a solution comprising or suspected of comprising the enzymes results in the enzymes, if present, reacting with the chromogenic substrate, the chromogenic substrate is one that, when reacted with the enzyme produces a colored product that is detected, and detection of the coloured product indicates that the solution comprised the enzymes.

2. The biosensor of claim 1, wherein the substrate is made from paper or paper-based material.

3. The biosensor of claim 1, wherein the biomolecule compatible sol gel is prepared from a sodium silicate precursor solution.

4. The biosensor of claim 1, wherein the first and second biomolecule compatible sol gel layers are immobilized on the substrate using ink jet printing of solutions comprising precursors for formation of the sol gel.

5. The biosensor of claim 4, wherein the ink jet printing is piezoelectric ink jet printing.

6. The biosensor of claim 4, wherein the chromogenic substrate for the enzyme is immobilized on the substrate using injet printing of a solution comprising the chromogenic substrate.

7. The biosensor of claim 6, wherein the ink jet printing is piezoelectric ink jet printing.

8. The biosensor of claim 1, wherein the chromogenic substrate for β-glucuronidase is 5-bromo-4-chloro-3-indolyl-β-D-glucuronide (X-GLUC).

9. The biosensor of claim 1, wherein the chromogenic substrate for β-galactosidase is selected from bromo-chloro-indolyl-galactopyranoside (X-GAL), 5-bromo-3-indolyl β-D-galactopyranoside (Bluo-Gla), 5-bromo-6-chloro-3-indolyl β-D-galactopryaniside (Magenta-Gal), 6-chloro-3-indolyl β-D-galactopyranoside (Salmon-Gal), 2-nitrophenyl β-D-galactopyranoside (ONPG) and 4-nitro β-D-galactopyranoside (PNPG).

10. The biosensor claim 9, wherein the chromogenic substrate for β-galactosidase is bromo-chloro-indolyl-galactopyranoside (X-GAL).

11. The biosensor of claim 1, wherein the reaction zone further comprises an oxidizing agent.

12. The biosensor of claim 11, wherein the oxidizing agent is $FeCl_3$.

13. The biosensor of claim 1, further comprising an additional reaction zone immobilized on the substrate wherein the additional reaction zone comprises layers that are arranged in order beginning adjacent to the substrate of: (i) a first biomolecule compatible sol gel layer; (ii) an oxidizing agent layer; and (iii) a second biomolecule compatible sol gel layer;
wherein immersion of the first end of the substrate in a solution comprising or suspected of comprising the enzymes, results in lateral flow of the solution from the first end of the substrate to the second end of the substrate by capillary action, the flow passing through the additional reaction zone prior to passing through the reaction zone, the chromogenic substrate for the enzymes is one that, when reacted with the enzyme produces a product that is oxidized by the oxidizing agent to a colored product that is detected, and detection of the colored product indicates that the solution comprised the enzymes.

14. The biosensor of claim 13, wherein the oxidizing agent is $FeCl_3$.

15. The biosensor of claim 1, wherein the microorganism is selected from one or more of *E. coli* and *salmonella*.

16. The biosensor of claim 1, wherein the reaction zone further comprises a capture means selected from one or more of a chemical agent having affinity for the chromogenic substrate and a physical barrier surrounding the reaction zone.

17. The biosensor of claim 16, wherein the capture means is a chemical agent having affinity for the chromogenic substrate and the chemical agent is comprised in a layer below the first biomolecule compatible sol gel layer.

18. A kit comprising a biosensor of claim 1.

19. A kit comprising a biosensor of claim 13.

20. The biosensor of claim 1, wherein the solution comprising or suspected of comprising the enzymes comprises microorganisms from an environmental, manufactured or synthetic source, and the solution has been treated to lyse the microorganisms.

21. The biosensor of claim 20, wherein the environmental source is a water or soil source.

22. The biosensor of claim 20, wherein the manufactured source is a food or drink source.

* * * * *